United States Patent
Klaveness et al.

(10) Patent No.: US 6,331,289 B1
(45) Date of Patent: Dec. 18, 2001

(54) TARGETED DIAGNOSTIC/THERAPEUTIC AGENTS HAVING MORE THAN ONE DIFFERENT VECTORS

(75) Inventors: Jo Klaveness; Pål Rongved; Anders Høgset; Helge Tolleshaug; Alan Cuthbertson; Lars Hoff; Klaus Bryn; Halldis Hellebust; Magne Solbakken, all of Olso (NO)

(73) Assignee: Nycomed Imaging AS, Oslo (NO)

( * ) Notice: Subject to any disclaimer, the term of this patent is extended or adjusted under 35 U.S.C. 154(b) by 0 days.

(21) Appl. No.: 08/959,206

(22) Filed: Oct. 28, 1997

Related U.S. Application Data

(60) Provisional application No. 60/049,263, filed on Jun. 7, 1997, provisional application No. 60/049,264, filed on Jun. 6, 1997, and provisional application No. 60/049,266, filed on Jun. 7, 1997.

(30) Foreign Application Priority Data

| Oct. 28, 1996 | (GB) | 9622366 |
| Oct. 28, 1996 | (GB) | 9622369 |
| Feb. 4, 1997 | (GB) | 9702195 |
| Apr. 24, 1997 | (GB) | 9708265 |
| Jun. 6, 1997 | (GB) | 9711837 |
| Jun. 6, 1997 | (GB) | 9711839 |

(51) Int. Cl.$^7$ ............ A61B 8/00; A61K 51/00; A61K 9/127
(52) U.S. Cl. .......... 424/9.52; 424/1.21; 424/9.4; 424/9.6; 424/450
(58) Field of Search ............ 424/9.52, 9.51, 424/9.5, 450, 489, 498, 499, 502, 1.21, 9.4, 9.6, 9.1; 530/300, 324, 326, 327; 514/14

(56) References Cited

U.S. PATENT DOCUMENTS

| 4,927,916 | 5/1990 | Matsueda | 530/387 |
| 5,013,556 | 5/1991 | Woodle et al. | 424/450 |
| 5,154,924 | 10/1992 | Friden | 424/85.91 |
| 5,198,424 | 3/1993 | McEver | 514/13 |
| 5,356,633 | 10/1994 | Woodle et al. | 424/450 |
| 5,362,478 | 11/1994 | Desai et al. | 424/9 |
| 5,498,421 | * 3/1996 | Grinstaff et al. | 424/450 |
| 5,505,932 | 4/1996 | Grinstaff et al. | 424/9.3 |
| 5,534,241 | 7/1996 | Torchilin et al. | 424/9.321 |
| 5,612,057 | 3/1997 | Lanza et al. | 424/450 |
| 5,632,986 | 5/1997 | Tait et al. | 424/94.64 |
| 5,643,553 | 7/1997 | Schneider et al. | 424/9.52 |
| 5,650,156 | 7/1997 | Grinstaff et al. | 424/400 |
| 5,656,211 | 8/1997 | Unger et al. | 264/4.1 |
| 5,665,383 | 9/1997 | Grinstaff et al. | 424/450 |
| 5,690,907 | 11/1997 | Lanza et al. | 424/9.5 |
| 5,716,594 | 2/1998 | Elmaleh et al. | 424/1.41 |
| 5,733,572 | 3/1998 | Unger et al. | 424/450 |
| 5,780,010 | 7/1998 | Lanza et al. | 424/9.32 |
| 5,846,517 | 12/1998 | Unger | 424/9.52 |
| 5,849,727 | 12/1998 | Porter et al. | 514/156 |
| 5,910,300 | * 6/1999 | Tournier et al. | 424/9.34 |
| 6,245,318 | 6/2001 | Klibanov et al. | 424/9.52 |

FOREIGN PATENT DOCUMENTS

| 2 145 505 | 4/1994 | (CA) . |
| 1 9 626 530 | 7/1996 | (DE) . |
| 0 727 225 | 8/1996 | (EP) . |
| WO 93/20802 | 10/1993 | (WO) . |
| WO 94/07539 | 4/1994 | (WO) . |
| WO 94/28873 | 12/1994 | (WO) . |
| WO 94/28874 | 12/1994 | (WO) . |
| WO 95/03356 | 2/1995 | (WO) . |
| WO 95/03357 | 2/1995 | (WO) . |
| WO 95/07072 | 3/1995 | (WO) . |
| WO 95/15118 | 6/1995 | (WO) . |
| WO 96/39149 | 12/1996 | (WO) . |
| WO 96/40277 | 12/1996 | (WO) . |
| WO 96/40285 | 12/1996 | (WO) . |
| WO 96/41647 | 12/1996 | (WO) . |
| WO 97/23855 | 7/1997 | (WO) . |
| WO 97/33474 | 9/1997 | (WO) . |
| WO 97/41898 | 11/1997 | (WO) . |
| WO 98/00172 | 1/1998 | (WO) . |
| WO 98/04293 | 2/1998 | (WO) . |
| WO 98/19705 | 5/1998 | (WO) . |
| WO 98/20856 | 5/1998 | (WO) . |
| WO 98/42384 | 10/1998 | (WO) . |

OTHER PUBLICATIONS

Worthington Enzyme Manual, Worthington Biochemical Corporation, 1972.
U.S. application No. 08/640,464, Unger, filed May 1, 1996.
U.S. application No. 08/660,032, Unger, filed Jun. 6, 1996.
U.S. application No. 08/712,173, Unger, filed Sep. 11, 1996.
Medline database extract No. XP–002063692, 1997.
Biosis database extract No. XP–002063693, Nov. 1997.
Medline database extract No. KP–002064110, 1997.
Muzykantov et al., J. Nuclear Medicine, 35(8): 1358–1365 (1994).
Klibanov et al., Acta Radiologica, 38(Supp 412):113–120 (1997).

* cited by examiner

*Primary Examiner*—Michael G. Hartley
(74) *Attorney, Agent, or Firm*—Bacon & Thomas

(57) ABSTRACT

Targetable diagnostic and/or therapeutically active agents, e.g. ultrasound contrast agents, comprising a suspension in an aqueous carrier liquid of a reporter comprising gas-containing or gas-generating material, said agent being capable of forming at least two types of binding pairs with a target.

22 Claims, 1 Drawing Sheet

TARGETED DIAGNOSTIC/THERAPEUTIC AGENTS HAVING MORE THAN ONE DIFFERENT VECTORS

This application claims benefit of the filing dates under 35 USC 119(e) of U.S. provisional applications 60/049,263 and 049,264 filed on Jun. 6, 1997 and 60/049,266 filed on Jun. 7, 1997.

It is well known that ultrasonic imaging comprises a potentially valuable diagnostic tool, for example in studies of the vascular system, particularly in cardiography, and of tissue microvasculature. A variety of contrast agents has been proposed to enhance the acoustic images so obtained, including suspensions of solid particles, emulsified liquid droplets, gas bubbles and encapsulated gases or liquids. It is generally accepted that low density contrast agents which are easily compressible are particularly efficient in terms of the acoustic backscatter they generate, and considerable interest has therefore been shown in the preparation of gas-containing and gas-generating systems.

Gas-containing contrast media are also known to be effective in magnetic resonance (MR) imaging, e.g. as susceptibility contrast agents which will act to reduce MR signal intensity. Oxygen-containing contrast media also represent potentially useful paramagnetic MR contrast agents.

Furthermore, in the field of x-ray imaging it has been observed that gases such as carbon dioxide may be used as negative oral contrast agents or intravascular contrast agents.

The use of radioactive gases, e.g. radioactive isotopes of inert gases such as xenon, has also been proposed in scintigraphy, for example for blood pool imaging.

Targeted ultrasound contrast agents may be regarded as comprising (i) a reporter moiety capable of interacting with ultrasound irradiation to generate a detectable signal; (ii) one or more vectors having affinity for particular target sites and/or structures within the body, e.g. for specific cells or areas of pathology; and (iii) one or more linkers connecting said reporter and vector(s), in the event that these are not directly joined.

The molecules and/or structure to which the contrast agent is intended to bind will hereinafter be referred to as the target. In order to obtain specific imaging of a selected region/structure in the body the target must be present and available in this region/structure. Ideally it will be expressed only in the region of interest, but usually will also be present at other locations in the body, creating possible background problems. The target may either be a defined molecular species (i.e. a target molecule) or an unknown molecule or more complex structure (i.e. a target structure) which is present in the area to be imaged, and is able to bind specifically or selectively to a given vector molecule.

The vector is attached to the reporter moiety in order to bind these moieties to the region/structure to be imaged. The vector may bind specifically to a chosen target, or it may bind only selectively, having affinty also for a limited number of other molecules/structures, again creating possible background problems.

There is a limited body of prior art relating to targeted ultrasound contrast agents. Thus, for example, US-A-5531980 is directed to systems in which the reporter comprises an aqueous suspension of air or gas microbubbles stabilised by one or more film-forming surfactants present at least partially in lamellar or laminar form, said surfactant(s) being bound to one or more vectors comprising "bioactive species designed for specific targeting purposes". It is stated that the microbubbles are not directly encapsulated by surfactant material but rather that this is incorporated in liquid-filled liposomes which stabilise the microbubbles. It will be appreciated that lamellar or laminar surfactant material such as phospholipids present in such liposomes will inevitably be present in the form of one or more lipid bilayers with the lipophilic tails "back-to-back" and the hydrophilic heads both inside and outside (see e.g. Schneider, M. on "Liposomes as drug carriers: 10 years of research" in *Drug targeting*, Nyon, Switzerland, 3–5 October 1984, Buri, P. and Gumma, A. (Ed), Elsevier, Amsterdam 1984).

EP-A-0727225 describes targeted ultrasound contrast agents in which the reporter comprises a chemical having a sufficient vapour pressure such that a proportion of it is a gas at the body temperature of the subject. This chemical is associated with a surfactant or albumin carrier which includes a protein-, peptide- or carbohydrate-based cell adhesion molecule ligand as vector. The receptor moieties in such contrast agents correspond to the phase shift colloid systems described in WO-A-9416739; it is now recognised that administration of such phase shift colloids may lead to generation of microbubbles which grow uncontrollably, possibly to the extent where they cause potentially dangerous embolisation of, for example, the myocardial vasculature and brain (see e.g. Schwarz, *Advances in Echo-Contrast* [1994(3)], pp 48–49).

WO-A-9320802 proposes that tissue-specific ultrasonic image enhancement may be achieved using acoustically reflective oligolamellar liposomes conjugated to tissue-specific ligands such as antibodies, peptides, lectins etc. The liposomes are deliberately chosen to be devoid of gas and so will not have the advantageous echogenic properties of gas-based ultrasound contrast agents. Further references to this technology, e.g. in targeting to fibrin, thrombi and atherosclerotic areas are found in publications by Alkanonyuksel, H. et al. in *J. Pharm. Sci.* (1996) 85(5), 486–490; *J. Am. Coll. Cardiol.* (1996) 27(2) Suppl A, 298A; and *Circulation*, 68 *Sci. Sessions*, Anaheim 13–16 November 1995.

There is also a number of publications concerning ultrasound contrast agents which refer in passing to possible use of monoclonal antibodies as vectors without giving significant practical detail and/or to reporters comprising materials which may be taken up by the reticuloendothelial system and thereby permit image enhancement of organs such as the liver—see, for example WO-A-9300933, WO-A-9401140, WO-A-9408627, WO-A-9428874, U.S. Pat. No. 5,088,499, U.S. Pat. No. 5,348,016 and U.S. Pat. No. 5,469,854. In general these prior art targeted contrast agents are intended to enhance contrast at specific sites in the body, for example tumour cells, by using one vector to bind strongly to one target, in order to achieve concentration at the target cells. In contrast to this principle of using one vector to bind with high affinity to one target, the present invention is based in part on the finding that diagnostic and/or therapeutically active agents with more favourable properties may be obtained by use of multiple kinds of vector-target interactions (e.g. involving agents associated with a plurality of different vectors and/or with one or more vectors having affinity for different targets on the same or different cell types). In this way, binding of gas-containing and gas-generating diagnostic and/or therapeutic agents may, for example, be obtained by forming multiple binding pairs between one vector with specificity for more than one receptor or between more than one vector with affinity for one or more types of target, with either low or high affinities. Such multiple binding of the vector-conjugated agent to one or more target molecules/structures may result in advantageous targeting properties, for example by enhancing target specificity and/or by distinguishing interactions at a desired target area from background interactions with lower levels of molecules/structures similar to target expressed elsewhere in the body.

It is well known to use one vector binding with high affinity to one target. The present invention, however, is based on the finding that the desired binding of gas-containing and gas-generating diagnostic and/or therapeutic agents may be obtained by forming multiple binding pairs with low affinity between one type of vector and one type of target, or by forming multiple binding pairs between one or more types of vectors and one or more types of target, with either low or high affinities. Thus multiple binding of the vector conjugated agent to one or more target molecules/structures may have advantageous targeting properties, for example in enhancing target specificity and/or in distinguishing interactions at a desired target area from background interactions with lower levels of molecules/structures similar to target expressed elsewhere in the body.

Thus according to one aspect of the present invention there is provided a targetable diagnostic and/or therapeutically active agent, e.g. an ultrasound contrast agent, comprising a suspension in an aqueous carrier liquid, e.g. an injectable carrier liquid, of a reporter comprising gas-containing or gas-generating material characterised in that said agent is capable of forming at least two types of binding pairs, e.g. being conjugated to at least two vectors or to one vector capable of binding to at least two binding sites.

One advantageous embodiment of the invention is based on the additional finding that limited adhesion to targets is a highly useful property of diagnostic and/or therapeutically active agents, which property may be achieved using vectors giving temporary retention rather than fixed adhesion to a target. Thus such agents, rather than being fixedly retained at specific sites, may for example effectively exhibit a form of retarded flow along the vascular endothelium by virtue of their transient interactions with endothelial cells. Such agents may thus become concentrated on the walls of blood vessels, in the case of ultrasound contrast agents providing enhanced echogenicity thereof relative to the bulk of the bloodstream, which is devoid of anatomical features. They therefore may permit enhanced imaging of the capillary system, including the microvasculature, and so may facilitate distinction between normal and inadequately perfused tissue, e.g. in the heart, and may also be useful in visualising structures such as Kupffer cells, thrombi and atherosclerotic lesions or for visualising neo-vascularized and inflamed tissue areas. The present invention is well suited to imaging changes occurring in normal blood vessels which are situated in areas of tissue necrosis.

It will be appreciated that binding affinities are dependent on numbers of interactions as well as their strength. The density of vector molecules at the surface of the reporter units may therefore be selected so as appropriately to adjust the degree of interactions between particular agents and targets.

The term multiple-specificity is also used to describe an injectable carrier liquid, of gas-containing or gas-generating material composed of one or more vectors with a specificity for one or more cellular surface receptors while at the same time comprising a second element with specificity for a substrate or receptor system binding to which induces a therapeutic response. Thus included within the scope of the present invention are multiple-specific imaging agents comprising a targeting vector, such as the anti-fibrin antibody described by Lanza et al. (*Circulation*, (1996) 94 (12),pp 3334), annexin V atherosclerotic plaque binding peptides such as YRALVDTLK, or any other vector known to associate with fibrin clots, in combination with a drug or enzyme with fibrinolytic activity such as streptokinase, plasminogen activator (tPA), urokinase (uPA) or prourokinase (scuPA) resulting in a localised therapeutic antithrombotic effect. This invention is also extended to include vectors with increased specificity for tumour cells in combination with vectors or drug molecules functioning as chemotherapeutic agents capable of inhibiting tumour growth.

It is well known that many, if not all, target molecules are not expressed exclusively at target sites; a common situation is that such molecules are over-expressed by target cells or at a target structure but are also expressed at lower levels elsewhere in the body. The use of reporters carrying a multiplicity of vectors with relatively low affinity for the target may be advantageous in this situation, since the reporter will then tend to concentrate in regions of high target density which permit multiple (and therefore strong) binding to the reporter (e.g. a gas-containing agent incorporating the vectors folic acid and glutathione for multiple-specific binding to folic acid receptors and glutathione-S-trasferase receptors respectively which are over-expressed as tumour cells). Areas of low target density, on the other hand, will not provide sufficient interaction with such low affinity vectors to bind the target. In such embodiments of the invention, low affinity vectors may be regarded as having an association constant $K_a$ for interaction with a target molecule or structure of less than $10^8$ $M^{-1}$, e.g. less than $10^7$ $M^{-1}$, preferably less than $10^6$ $M^{-1}$. A further embodiment of this invention is thus based on the finding that the desired binding of gas-containing and gas-generating diagnostic and/or therapeutic agents may be obtained by forming binding pairs with low affinity between more than one type of vector and one or more type of target. Multiple vectors may therfore be used to increase specificity, so that the reporter will bind only to target cells or structures expressing a particular combination of target molecules.

It may also be useful to select a plurality of vectors which bind to different parts, e.g. epitopes, of a target structure in order to give increased binding strength. This may be particularly advantageous when the target density is low.

Products comprising two or more vectors with different specificities, i.e. which bind to different target molecules on different cells, may advantageously be used as "general purpose" agents for detection of a range of diseases, e.g. different forms of cancer. Thus, for example, the use of such agents may enable detection of metastases, which are often heterogeneous with respect to expression of target molecules (i.e. antigens).

Within the context of the present invention, the reporter unit will usually remain attached to the vectors. In another type of targeting procedure, sometimes called pre-targeting, the vector (often, a monoclonal antibody) is administered alone; subsequently, the reporter is administered, coupled to a moiety which is capable of specifically binding the vector molecule (when the vector is an antibody, the reporter may be coupled to an immunoglobulin-binding molecule, such as protein A or an anti-immunoglobulin antibody). An advantage of this protocol is that time may be allowed for elimination of the vector molecules that do not bind their targets, substantially reducing the background problems that are connected with the presence of an excess of reporter-vector conjugate. Within the context of the present invention, pre-targeting with one specific vector might be envisaged, followed by reporter units that are coupled to another vector and a moiety which binds the first vector.

Within the context of the present invention, in some cases and in particular for the assessment of blood perfusion rates in defined areas, for example in myocardium, it is of interest to measure the rate at which ultrasound contrast agents bound to the target are displaced or released from the target. This can be achieved in a controlled fashion by subsequent administration of a vector or other agent able to displace or release the contrast agent from the target.

Figure 1:
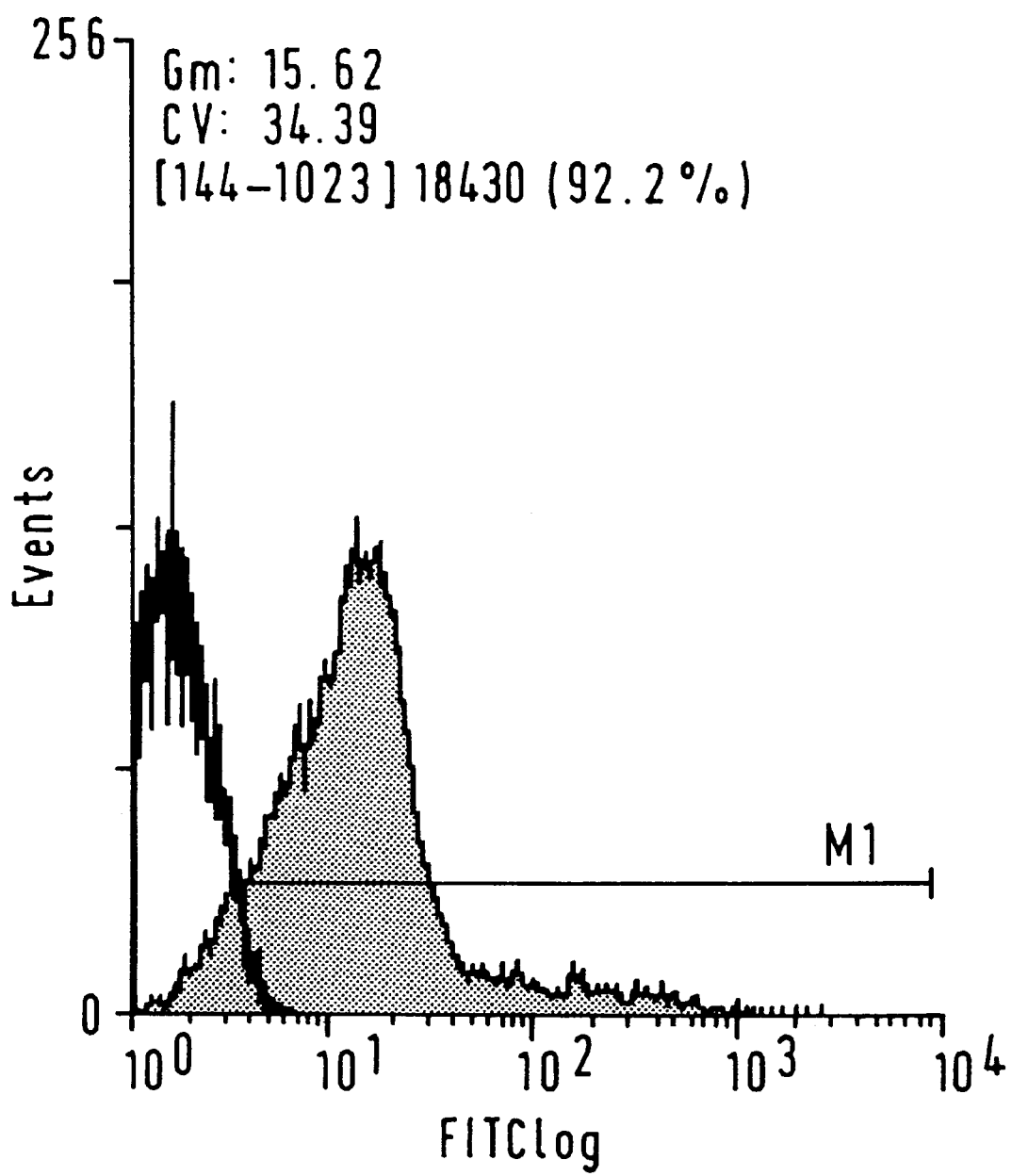
FIG. 1 Flow cytometric comparison of negative control microbubbles of DSPS (left curve) with bubbles conjugated with CD71 FITC-labelled anti-transferrin antibody (filled curve, right) showing that 92% of the population fluoresce.

Vectors useful in accordance with the invention include ligands for cell adhesion proteins, as well as cell adhesion proteins themselves where these have corresponding ligands on endothelial cell surfaces. Examples of cell adhesion proteins include integrins, most of which bind the Arg-Gly-Asp (RGD) amino acid sequence. If desired, the vector may be targeted to specific cell adhesion proteins expressed mainly on activated endothelial cells such as are found at or close to sites of inflammation or other pathological responses. Other vectors which may be used include proteins and peptides that bind to cell-surface proteoglycans, which are complexes of proteins and sulphated polysaccarides found on most cells, including endothelial cells. Such proteoglycans contribute to the negative surface charge of all nucleated cells from vertebrate animals; this charge may also be exploited in accordance with the invention by using positively charged vectors, e.g. comprising cationic lipids, which will interact electrostatically with the endothelial surface.

A further aspect of the present invention is for example where a vector or vectors is attached to the reporter or included non-covalently into the reporter in a manner where the said vector or vectors is not readily exposed to the targets or receptors. Increased tissue specificity may therefore be achieved by applying an additional process to expose the vectors, e.g. the agent is exposed after administration to external ultrasound to change the diffusibility of the moieties containing the vectors.

The reporter may be in any convenient form, for example being any appropriate gas-containing or gas-generating ultrasound contrast agent formulation. Representative examples of such formulations include microbubbles of gas stabilised (e.g. at least partially encapsulated) by a coalescence-resistant surface membrane (for example gelatin, e.g. as described in WO-A-8002365), a filmogenic protein (for example an albumin such as human serum albumin, e.g. as described in U.S. Pat. No. 4,718,433, U.S. Pat. No. 4,774,958, U.S. Pat. No. 4,844,882, EP-A-0359246, WO-A-9112823, WO-A-9205806, WO-A-9217213, WO-A-9406477 or WO-A-9501187), a polymer material (for example a synthetic biodegradable polymer as described in EP-A-0398935, an elastic interfacial synthetic polymer membrane as described in EP-A-0458745, a microparticulate biodegradable polyaldehyde as described in EP-A-0441468, a microparticulate N-dicarboxylic acid derivative of a polyamino acid—polycyclic imide as described in EP-A-0458079, or a biodegradable polymer as described in WO-A-9317718 or WO-A-9607434), a non-polymeric and non-polymerisable wall-forming material (for example as described in WO-A-9521631), or a surfactant (for example a polyoxyethylene-polyoxypropylene block copolymer surfactant such as a Pluronic, a polymer surfactant as described in WO-A-9506518, or a film-forming surfactant such as a phospholipid, e.g. as described in WO-A-9211873, WO-A-9217212, WO-A-9222247, WO-A-9428780 or WO-A-9503835).

Other useful gas-containing contrast agent formulations include gas-containing solid systems, for example microparticles (especially aggregates of microparticles) having gas contained therewithin or otherwise associated therewith (for example being adsorbed on the surface thereof and/or contained within voids, cavities or pores therein, e.g. as described in EP-A-0122624, EP-A-0123235, EP-A-0365467, WO-A-9221382, WO-A-9300930, WO-A-9313802, WO-A-9313808 or WO-A-9313809). It will be appreciated that the echogenicity of such microparticulate contrast agents may derive directly from the contained/associated gas and/or from gas (e.g. microbubbles) liberated from the solid material (e.g. upon dissolution of the microparticulate structure).

The disclosures of all of the above-described documents relating to gas-containing contrast agent formulations are incorporated herein by reference.

Gas microbubbles and other gas-containing materials such as microparticles preferably have an initial average size not exceeding 10 $\mu$m (e.g. of 7 $\mu$m or less) in order to permit their free passage through the pulmonary system following administration, e.g. by intravenous injection.

Where phospholipid-containing compositions are employed in accordance with the invention, e.g. in the form of phospholipid-stabilised gas microbubbles, representative examples of useful phospholipids include lecithins (i.e. phosphatidylcholines), for example natural lecithins such as egg yolk lecithin or soya bean lecithin and synthetic or semisynthetic lecithins such as dimyristoylphosphatidylcholine, dipalmitoylphosphatidylcholine or distearoylphosphatidylcholine; phosphatidic acids; phosphatidylethanolamines; phosphatidylserines; phosphatidylglycerols; phosphatidylinositols; cardiolipins; sphingomyelins; fluorinated analogues of any of the foregoing; mixtures of any of the foregoing and mixtures with other lipids such as cholesterol. The use of phospholipids predominantly (e.g. at least 75%) comprising molecules individually bearing net overall charge, e.g. negative charge, for example as in naturally occurring (e.g. soya bean or egg yolk derived), semisynthetic (e.g. partially or fully hydrogenated) and synthetic phosphatidylserines, phosphatidylglycerols, phosphatidylinositols, phosphatidic acids and/or cardiolipins, may be particularly advantageous.

Other exemplary lipids which may be used to prepare gas-containing contrast agents include fatty acids, stearic acid, palmitic acid, 2-n-hexadecylstearic acid, oleic acid and other acid containing lipid structures. These lipid structures are considered particularly interesting when coupled by amide bond formation to amino acids containing one or more amino groups. The resulting lipid modified amino acids (e.g. dipalmitoyllysine, distearoyl-2,3-diaminopropionic acid) are considered useful precursors for the attachment of functionalised spacer elements featuring coupling sites for conjugation of one or more vector molecules.

A further extension of this invention relates to the synthesis of lipopeptide structures comprising a lipid reporter attached to a linker portion (e.g. PEG, polyamino acid, alkylhalide etc) the said linker being suitably functionalised for coupling to one or more vector molecules. A particular preference is the inclusion of a positively charged linker element (eg. two or more lysine residues) for anchoring of the reporter element in the microbubble through electrostatic interaction with the negatively charged membrane. Multiple-specific targeting is achievable by mixing and 'doping' of phospholipid gas-containing structures with one or more targeted lipopeptide sequences. Multiple-specificity can also be achieved by assembling more than one vector on a branched lysine core structure such as those described by Tam et. al. (Proc. Natl. Acad. Sci. USA, 1989, 86, 9084) or by incorporating multiple vectors in a linear sequence. Multiple-specificity can also be achieved using lipopeptides or phospholipids comprising combinatorial libraries synthesised by chemical synthesis as described by Lowe (Combinatorial Chemistry, Chemical Society Reviews, 1995, 309–317).

Also within the scope of this invention are functionalised microbubbles carrying one or more reactive groups for non-specific reaction with receptor molecules located on cell surfaces. Microbubbles comprising a thiol moiety, for example, can bind to cell surface receptors via disulphide exchange reactions. The reversible nature of this covalent bond means that bubble flow can be controlled by altering the redox environment. Similarly 'activated' microbubbles of membranes comprising active esters such as N-hydroxysuccinimide esters can be used to modify amino groups found on a multiplicity of cell surface molecules.

Representative examples of gas-containing microparticulate materials which may be useful in accordance with the invention include carbohydrates (for example hexoses such as glucose, fructose or galactose; disaccharides such as sucrose, lactose or maltose; pentoses such as arabinose, xylose or ribose; α-, β- and γ-cyclodextrins; polysaccharides such as starch, hydroxyethyl starch, amylose, amylopectin, glycogen, inulin, pulullan, dextran, carboxymethyl dextran, dextran phosphate, ketodextran, aminoethyldextran, alginates, chitin, chitosan, hyaluronic acid or heparin; and sugar alcohols, including alditols such as mannitol or sorbitol), inorganic salts (e.g. sodium chloride), organic salts (e.g. sodium citrate, sodium acetate or sodium tartrate), X-ray contrast agents (e.g. any of the commercially available carboxylic acid and non-ionic amide contrast agents typically containing at least one 2,4,6-triiodophenyl group having substituents such as carboxyl, carbamoyl, N-alkylcarbamoyl, N-hydroxyalkylcarbamoyl, acylamino, N-alkylacylamino or acylaminomethyl at the 3- and/or 5-positions, as in metrizoic acid, diatrizoic acid, iothalamic acid, ioxaglic acid, iohexol, iopentol, iopamidol, iodixanol, iopromide, metrizamide, iodipamide, meglumine iodipamide, meglumine acetrizoate and meglumine diatrizoate), and polypeptides and proteins (e.g. gelatin or albumin such as human serum albumin).

Any biocompatible gas may be present in the reporter of contrast agents according to the invention, the term "gas" as used herein including any substances (including mixtures) substantially or completely in gaseous (including vapour) form at the normal human body temperature of 37° C. The gas may thus, for example, comprise air; nitrogen; oxygen; carbon dioxide; hydrogen; an inert gas such as helium, argon, xenon or krypton; a sulphur fluoride such as sulphur hexafluoride, disulphur decafluoride or trifluoromethylsulphur pentafluoride; selenium hexafluoride; an optionally halogenated silane such as methylsilane or dimethylsilane; a low molecular weight hydrocarbon (e.g. containing up to 7 carbon atoms), for example an alkane such as methane, ethane, a propane, a butane or a pentane, a cycloalkane such as cyclopropane, cyclobutane or cyclopentane, an alkene such as ethylene, propene, propadiene or a butene, or an alkyne such as acetylene or propyne; an ether such as dimethyl ether; a ketone; an ester; a halogenated low molecular weight hydrocarbon (e.g. containing up to 7 carbon atoms); or a mixture of any of the foregoing. Advantageously at least some of the halogen atoms in halogenated gases are fluorine atoms; thus biocompatible halogenated hydrocarbon gases may, for example, be selected from bromochlorodifluoromethane, chlorodifluoromethane, dichlorodifluoromethane, bromotrifluoromethane, chlorotrifluoromethane, chloropentafluoroethane, dichlorotetrafluoroethane, chlorotrifluoroethylene, fluoroethylene, ethylfluoride, 1,1-difluoroethane and perfluorocarbons, e.g. perfluoroalkanes such as perfluoromethane, perfluoroethane, perfluoropropanes, perfluorobutanes (e.g. perfluoro-n-butane, optionally in admixture with other isomers such as perfluoro-iso-butane), perfluoropentanes, perfluorohexanes and perfluoroheptanes; perfluoroalkenes such as perfluoropropene, perfluorobutenes (e.g. perfluorobut-2-ene) and perfluorobutadiene; perfluoroalkynes such as perfluorobut-2-yne; and perfluorocycloalkanes such as perfluorocyclobutane, perfluoromethylcyclobutane, perfluorodimethylcyclobutanes, perfluorotrimethylcyclobutanes, perfluorocyclopentane, perfluoromethylcyclopentane, perfluorodimethylcyclopentanes, perfluorocyclohexane, perfluoromethylcyclohexane and perfluorocycloheptane. Other halogenated gases include methyl chloride, fluorinated (e.g. perfluorinated) ketones such as perfluoroacetone and fluorinated (e.g. perfluorinated) ethers such as perfluorodiethyl ether. The use of perfluorinated gases, for example sulphur hexafluoride and perfluorocarbons such as perfluoropropane, perfluorobutanes and perfluoropentanes, may be particularly advantageous in view of the recognised high stability in the bloodstream of microbubbles containing such gases.

The reporter may be made by any convenient process, for example by making gas-containing or gas-generating formulations. Representative examples include the preparation of a suspension of gas microbubbles by contacting a surfactant with gas and mixing them in the presence of an aqueous carrier, as described in WO 9115244; or by atomising a solution or dispersion of a wall-forming material in the presence of a gas in order to obtain hollow microcapsules, as described in EP 512693A1; preparation of solid microspheres by a double emulsion process, as described in U.S. Pat. No. 5,648,095; or a process for forming hollow microcapsules by spray-drying as described in EP 681843A2; or preparing gas-filled liposomes by shaking an aqueous solution comprising a lipid in the presence of a gas as described in U.S. Pat. No. 5,469,854.

A suitable process for attachment of the desired vector to the reporter comprises a surface modification of the preformed reporter with a suitable linker employing reactive groups on the surface of both the reporter and vector. It may be particularly advantageous physically to mix the reporter material with the vector-containing substance at any step of the process. Such a process will result in incorporation or an attachment of the vector to the reporter. An optional process step may remove the excess of vector not bound to the reporter by washing the gas-containing particles following separation, by for example, floatation. A preferred aspect is the use of lipopeptide structures incorporating functional groups such as thiol, maleimide biotin etc. which can be premixed if desired with other reporter molecules before formation of gas-containing agents. The attachment of vector molecules may be carried out using the linker reagents listed below.

Linking of a reporter unit to the desired vectors may be achieved by covalent or non-covalent means, usually involving interaction with one or more functional groups located on the reporter and/or vectors. Examples of chemically reactive functional groups which may be employed for this purpose include amino, hydroxyl, sulfhydryl, carboxyl, and carbonyl groups, as well as carbohydrate groups, vicinal diols, thioethers, 2-aminoalcohols, 2-aminothiols, guanidinyl, imidazolyl and phenolic groups.

Covalent coupling of reporter and vectors may therefore be effected using linking agents containing reactive moieties capable of reaction with such functional groups. Examples of reactive moieties capable of reaction with sulfhydryl groups include α-haloacetyl compounds of the type X—$CH_2$CO— (where X=Br, Cl or I), which show particular reactivity for sulfhydryl groups but which can also be used to modify imidazolyl, thioether, phenol and amino groups as described by Gurd, F. R. N. in *Methods Enzymol.* (1967) 11, 532. N-Maleimide derivatives are also considered selective towards sulfhydryl groups, but may additionaly be useful in coupling to amino groups under certain conditions. N-maleimides may be incorporated into linking systems for reporter-vector conjugation as described by Kitagawa, T. et al. in *Chem. Pharm. Bull.* (1981) 29, 1130 or used as polymer crosslinkers for bubble stabilisation as described by Kovacic, P. et al. in *J. Am. Chem. Soc.* (1959) 81, 1887. Reagents such as 2-iminothiolane, e.g. as described by Traut, R. et al. in *Biochemistry* (1973) 12, 3266, which introduce a thiol group through conversion of an amino group, may be considered as sulfhydryl reagents if linking occurs through the formation of disulphide bridges. Thus reagents which introduce reactive disulphide bonds into either the reporter or the vectors may be useful, since linking may be brought about by disulphide exchange between the vector and reporter; examples of such reagents include Ellman's reagent (DTNB), 4,4'-dithiodipyridine, methyl-3-nitro-2-pyridyl disulphide and methyl-2-pyridyl disulphide (described by Kimura, T. et al. in *Analyt. Biochem.* (1982) 122, 271).

Examples of reactive moieties capable of reaction with amino groups include alkylating and acylating agents. Representative alkylating agents include:

i) α-haloacetyl compounds, which show specificity towards amino groups in the absence of reactive thiol groups and are of the type X—$CH_2$CO— (where X=Cl, Br or I), e.g. as described by Wong, Y-H.H. in *Biochemistry* (1979) 24, 5337;

ii) N-maleimide derivatives, which may react with amino groups either through a Michael type reaction or through acylation by addition to the ring carbonyl group as described by Smyth, D. G. et al. in *J. Am. Chem. Soc.* (1960) 82, 4600 and *Biochem. J.* (1964) 91, 589;

iii) aryl halides such as reactive nitrohaloaromatic compounds;

iv) alkyl halides as described by McKenzie, J. A. et al. in *J. Protein Chem.* (1988) 7, 581;

v) aldehydes and ketones capable of Schiff's base formation with amino groups, the adducts formed usually being stabilised through reduction to give a stable amine;

vi) epoxide derivatives such as epichlorohydrin and bisoxiranes,which may react with amino, sulfhydryl or phenolic hydroxyl groups;

vii) chlorine-containing derivatives of s-triazines, which are very reactive towards nucleophiles such as amino, sufhydryl and hydroxy groups;

viii) aziridines based on s-triazine compounds detailed above, e.g. as described by Ross, W. C. J. in *Adv. Cancer Res.* (1954) 2, 1, which react with nucleophiles such as amino groups by ring opening;

ix) squaric acid diethyl esters as described by Tietze, L. F. in *Chem. Ber.* (1991) 124, 1215; and x) α-haloalkyl ethers, which are more reactive alkylating agents than normal alkyl halides because of the activation caused by the ether oxygen atom, e.g. as described by Benneche, T. et al. in *Eur. J. Med. Chem.* (1993) 28, 463.

Representative amino-reactive acylating agents include:

i) isocyanates and isothiocyanates, particularly aromatic derivatives, Which form stable urea and thiourea derivatives respectively and have been used for protein crosslinking as described by Schick, A. F. et al. in *J. Biol. Chem.* (1961) 236, 2477;

ii) sulfonyl chlorides, which have been described by Herzig, D. J. et al. in *Biopolymers* (1964) 2, 349 and which may be useful for the introduction of a fluorescent reporter group into the linker;

iii) Acid halides;

iv) Active esters such as nitrophenylesters or N-hydroxysuccinimidyl esters;

v) acid anhydrides such as mixed, symmetrical or N-carboxyanhydrides;

vi) other useful reagents for amide bond formation as described by Bodansky, M. et al. in *'Principles of Peptide Synthesis'* (1984) Springer-Verlag;

vii) acylazides, e.g. wherein the azide group is generated from a preformed hydrazide derivative using sodium nitrite, e.g. as described by Wetz, K. et al. in *Anal. Biochem.* (1974) 58, 347;

viii) azlactones attached to polymers such as bis-acrylamide, e.g. as described by Rasmussen, J. K. in *Reactive Polymers* (1991) 16, 199; and ix) Imidoesters , which form stable amidines on reaction with amino groups, e.g. as described by Hunter, M. J. and Ludwig, M. L. in *J. Am. Chem. Soc.* (1962) 84, 3491.

Carbonyl groups such as aldehyde functions may be reacted with weak protein bases at a pH such that nucleophilic protein side-chain functions are protonated. Weak bases include 1,2-aminothiols such as those found in N-terminal cysteine residues, which selectively form stable 5-membered thiazolidine rings with aldehyde groups, e.g. as described by Ratner, S. et al. in *J. Am. Chem. Soc.* (1937) 59, 200. Other weak bases such as phenyl hydrazones may be used, e.g. as described by Heitzman, H. et al. in *Proc. Natl. Acad. Sci. USA* (1974) 71, 3537.

Aldehydes and ketones may also be reacted with amines to form Schiff's bases, which may advantageously be stabilised through reductive amination. Alkoxylamino moieties readily react with ketones and aldehydes to produce stable alkoxamines, e.g. as described by Webb, R. et al. in *Bioconjugate Chem.* (1990) 1, 96.

Examples of reactive moieties capable of reaction with carboxyl groups include diazo compounds such as diazoacetate esters and diazoacetamides, which react with high specificity to generate ester groups, e.g. as described by Herriot R. M. in *Adv. Protein Chem.* (1947) 3, 169. Carboxylic acid modifying reagents such as carbodiimides, which react through O-acylurea formation followed by amide bond formation, may also usefully be employed; linking may be facilitated through addition of an amine or may result in direct vector-receptor coupling. Useful water soluble carbodiimides include 1-cyclohexyl-3-(2-morpholinyl-4-ethyl)carbodiimide (CMC) and 1-ethyl-3-(3-dimethylaminopropyl)carbodiimide (EDC), e.g. as described by Zot, H. G. and Puett, D. in *J. Biol. Chem.* (1989) 264, 15552. Other useful carboxylic acid modifying reagents include isoxazolium derivatives such as Woodwards reagent K; chloroformates such as p-nitrophenylchloroformate; carbonyldiimidazoles such as 1,1'-carbonyldiimidazole; and N-carbalkoxydihydroquinolines such as N-(ethoxycarbonyl)-2-ethoxy-1,2-dihydroquinoline.

Other potentially useful reactive moieties include vicinal diones such as p-phenylenediglyoxal, which may be used to react with guanidinyl groups, e.g. as described by Wagner et al. in *Nucleic acid Res.* (1978) 5, 4065; and diazonium salts, which may undergo electrophilic substitution reactions, e.g. as described by Ishizaka, K. and Ishizaka T. in *J. Immunol.* (1960) 85, 163. Bis-diazonium compounds are readily prepared by treatment of aryl diamines with sodium nitrite in acidic solutions. It will be appreciated that functional groups in the reporter and/or vector may if desired be converted to other functional groups prior to reaction, e.g. to confer additional reactivity or selectivity. Examples of methods useful for this purpose include conversion of amines to carboxylic acids using reagents such as dicarboxylic anhydrides; conversion of amines to thiols using reagents such as N-acetylhomocysteine thiolactone, S-acetylmercaptosuccinic anhydride, 2-iminothiolane or thiol-containing succinimidyl derivatives; conversion of thiols to carboxylic acids using reagents such as a-haloacetates; conversion of thiols to amines using reagents such as ethylenimine or 2-bromoethylamine; conversion of carboxylic acids to amines using reagents such as carbodiimides followed by diamines; and conversion of alcohols to thiols using reagents such as tosyl chloride followed by transesterification with thioacetate and hydrolysis to the thiol with sodium acetate.

Vector-receptor coupling may also be effected using enzymes as zero-length crosslinking agents; thus, for example, transglutaminase, peroxidase and xanthine oxidase have been used to produce crosslinked products. Reverse proteolysis may also be used for crosslinking through amide bond formation.

Non-covalent vector-receptor coupling may, for example, be effected by electrostatic charge interactions e.g. between a polylysinyl-functionalised reporter and a polyglutamyl-functionalised vector, through chelation in the form of stable metal complexes or through high affinity binding interaction such as avidin/biotin binding. Polylysine, coated non-covalently to the negatively charged membrane surface can also increase non-specifically the affinity of a microbubble for a cell through charge interactions.

Alternatively, vectors may be coupled to a protein or peptide sequence known to bind phospholipids. In many instances, a single molecule of phospholipid may attach to a protein such as a translocase, while other proteins may attach to surfaces consisting mainly of phospholipid head groups and so may be used to attach vectors to phospholipid microspheres; one example of such a protein is β2-glycoprotein I (Chonn, A., Semple, S. C. and Cullis, P. R., *Journal of Biological Chemistry* (1995) 270, 25845–25849). Phosphatidylserine-binding proteins have been described, e.g. by Igarashi, K. et al. in *Journal of Biological Chemistry* 270(49), 29075–29078. Annexins are a class of phospholipid-binding proteins, many of which bind particularly avidly to phosphatidyl-serine (reviewed in Raynal, P. and H. B. Pollard. Annexins: the problem of assessing the biological role for a gene family of multifunctional calcium- and phospholipid-binding proteins". Biochim. Biophys. Acta 1197: 63–93). A conjugate of a vector with such a phosphatidylserine-binding protein may therefore be used to attach the vector to phosphatidylserine-encapsulated microbubbles. When the amino acid sequence of a binding protein is known, the phospholipid-binding portion may be synthesised or isolated and used for conjugation with a vector, thus avoiding the biological activity which may be located elsewhere in the molecule.

It is also possible to obtain molecules that bind specifically to the surface (or in the "membrane") of microspheres by direct screening of molecular libraries for microsphere-binding molecules. For example, phage libraries displaying small peptides could be used for such selection. The selection may be made by simply mixing the microspheres and the phage display library and eluting the phages binding to the floating microspheres. If desired, the selection can be done under "physiological conditions" (e.g. in blood) to eliminate peptides which cross-react with blood components. An advantage of this type of selection procedure is that only binding molecules that do not destabilize the microspheres should be selected, since only binding molecules attached to intact floating microspheres will rise to the top. It may also be possible to introduce some kind of "stress" during the selection procedure (e.g. pressure) to ensure that destabilizing binding moieties are not selected. Furthermore the selection could be done under shear conditions e.g. by first letting the phages react with the microspheres and then letting the microspheres pass through a surface coated with anti-phage antibodies under flow conditions. In this way it may be possible to select binders which may resist shear conditions present in vivo. Binding moieties identified in this way may be coupled (chemically via peptide synthesis, or at the DNA-level using recombinant vectors) to a vector molecule, constituting a general tool for attaching any vector molecule to the microspheres.

A vector which comprises or is coupled to a peptide or lipopeptide linker which contains a element capable of mediating membrane insertion may also be useful. One example is described by Leenhouts, J. M. et al. in *Febs Letters* (1995) 370(3), 189–192. Non-bioactive molecules consisting of known membrane insertion anchor/signal groups may also be used as vectors for certain applications, an example being the H1 hydrophobic segment from the Na, K-ATPase α-subunit described by Xie, Y. and Morimoto, T. in *J. Biol. Chem.* (1995) 270(20), 11985–11991. The anchor group may also be fatty acid(s) or cholesterol.

Coupling may also be effected using avidin or streptavidin, which have four high affinity binding sites for biotin. Avidin may therefore be used to conjugate vector to reporter if both vector and reporter are biotinylated. Examples are described by Bayer, E. A. and Wilchek, M. in *Methods Biochem. Anal.* (1980) 26, 1.

This method may also be extended to include linking of reporter to reporter, a process which may encourage bubble association and consequent potentially increased echogenicity.

Non-covalent coupling may also utilise the bifunctional nature of bispecific immunoglobulins. These molecules can specifically bind two antigens, thus linking them. For example, either bispecific IgG or chemically engineered bispecific F(ab)'2 fragments may be used as linking agents. Heterobifunctional bispecific antibodies have also been reported for linking two different antigens, e.g. as described by Bode, C. et al. in *J. Biol. Chem.* (1989) 264, 944 and by Staerz, U. D. et al. in *Proc. Natl. Acad. Sci. USA* (1986) 83, 1453. Similarly, any reporter and/or vector containing two or more antigenic determinants (e.g. as described by Chen, Aa et al. in *Am. J. Pathol.* (1988) 130, 216) may crosslink antibody molecules and lead to formation of multi-bubble cross-linked assemblies of potentially increased echogenicity.

So-called zero-length linking agents, which induce direct covalent joining of two reactive chemical groups without introducing additional linking material (e.g. as in amide bond formation induced using carbodiimides or enzymatically) may, if desired, be used, as may agents such as biotin/avidin systems which induce non-covalent reporter-vector linking and agents which induce hydrophobic or electrostatic interactions.

Most commonly, however, the linking agent will comprise two or more reactive moieties, e.g. as described above, connected by a spacer element. The presence of such a spacer permits bifunctional linkers to react with specific functional groups within a molecule or between two different molecules, resulting in a bond between these two components and introducing extrinsic linker-derived material into the reporter-vector conjugate. The reactive moieties in a linking agent may be the same (homobifunctional agents) or different (heterobifunctional agents or, where several dissimilar reactive moieties are present, heteromultifunctional agents), providing a diversity of potential reagents that may bring about covalent bonding between any chemical species, either intramolecularly or intermolecularly.

The nature of extrinsic material introduced by the linking agent may have a critical bearing on the targeting ability and general stability of the ultimate product. Thus it may be desirable to introduce labile linkages, e.g. containing spacer arms which are biodegradable or chemically sensitive or which incorporate enzymatic cleavage sites. Alternatively the spacer may include polymeric components, e.g. to act as surfactants and enhance bubble stability. The spacer may also contain reactive moieties, e.g. as described above to enhance surface crosslinking, or it may contain a tracer element such as a fluorescent probe, spin label or radioactive material.

Spacer elements may typically consist of aliphatic chains which effectively separate the reactive moieties of the linker by distances of between 5 and 30 Å. They may also comprise macromolecular structures such as poly(ethylene glycols). Such polymeric structures, hereinafter referred to as PEGs, are simple, neutral polyethers which have been given much attention in biotechnical and biomedical applications (see e.g. Milton Harris, J. (ed) "*Poly(ethylene glycol) chemistry, biotechnical and biomedical applications*" Plenum Press, New York, 1992). PEGs are soluble in most solvents, including water, and are highly hydrated in aqueous environments, with two or three water molecules bound to each ethylene glycol segment; this has the effect of preventing adsorption either of other polymers or of proteins onto PEG-modified surfaces. PEGs are known to be nontoxic and not to harm active proteins or cells, whilst covalently linked PEGs are known to be non-immunogenic and non-antigenic. Furthermore, PEGs may readily be modified and bound to other molecules with only little effect on their chemistry. Their advantageous solubility and biological properties are apparent from the many possible uses of PEGs and copolymers thereof, including block copolymers such as PEG-polyurethanes and PEG-polypropylenes.

Appropriate molecular weights for PEG spacers used in accordance with the invention may, for example, be between 120 Daltons and 20 kDaltons.

The major mechanism for uptake of particles by the cells of the reticuloendothelial system (RES) is opsonisation by plasma proteins in blood; these mark foreign particles which are then taken up by the RES. The biological properties of PEG spacer elements used in accordance with the invention may serve to increase contrast agent circulation time in a similar manner to that observed for PEGylated liposomes (see e.g. Klibanov, A. L. et al. in *FEBS Letters* (1990) 268, 235–237 and Blume, G. and Cevc, G. in *Biochim. Biophys. Acta* (1990) 1029, 91–97).

Other potentially useful protein modifications which can be made to vectors include partial or complete deglycosidation by neuraminidase, endoglycosydases or periodate, since deglycosidation often results in less uptake by liver, spleen, macrophages etc., whereas neo-glycosylation of proteins often results in increased uptake by the liver and macrophages); preparation of truncated forms by proteolytic cleavage, leading to reduced size and shorter half life in circulation; and cationisation, e.g. as described by Kumagi et al. in *J. Biol. Chem.* (1987) 262, 15214–15219; Triguero et al. in *Proc. Natl. Acad. Sci. USA* (1989) 86, 4761–4765; Pardridge et al. in *J. Pharmacol. Exp. Therap.* (1989) 251, 821–826 and Pardridge and Boado, *Febs Lett.* (1991) 288, 30–32.

Increased coupling efficiency to areas of interest may also be achieved using antibodies bound to the terminii of PEG spacers (see e.g. Maruyama, K. et al. in *Biochim. Biophys. Acta* (1995) 1234, 74–80 and Hansen, C. B. et al. in *Biochim. Biophys. Acta* (1995) 1239, 133–144).

In some instances it is considered advantageous to include a PEG component as a stabiliser in conjunction with a vector or vectors or directly to the reporter in the same molecule where the PEG does not serve as a spacer.

Other representative spacer elements include structural-type polysaccharides such as polygalacturonic acid, glycosaminoglycans, heparinoids, cellulose and marine polysaccharides such as alginates, chitosans and carrageenans; storage-type polysaccharides such as starch, glycogen, dextran and aminodextrans; polyamino acids and methyl and ethyl esters thereof, as in homo-and co-polymers of lysine, glutamic acid and aspartic acid; and polypeptides, oligonucleotides and oligosaccharides, which may or may not contain enzyme cleavage sites.

In general, spacer elements may contain cleavable groups such as vicinal glycol, azo, sulfone, ester, thioester or disulphide groups. Spacers containing biodegradable methylene diester or diamide groups of formula

$$-(Z)_m\text{-}Y.X.C(R^1R^2).X.Y.(Z)_n-$$

[where X and Z are selected from —O—, —S—, and —NR—(where R is hydrogen or an organic group); each Y is a carbonyl, thiocarbonyl, sulphonyl, phosphoryl or similar acid-forming group: m and n are each zero or 1; and $R^1$ and $R^2$ are each hydrogen, an organic group or a group —X.Y.$(Z)m_m$—, or together form a divalent organic group] may also be useful; as discussed in, for example, WO-A-9217436 such groups are readily biodegraded in the presence of esterases, e.g. in vivo, but are stable in the absence of such enzymes. They may therefore advantageously be linked to therapeutic agents to permit slow release thereof.

Poly[N-(2-hydroxyethyl)methacrylamides] are potentially useful spacer materials by virtue of their low degree of interaction with cells and tissues (see e.g. Volfová, I., Ríhová, B. and V. R. and Vetvicka, P. in *J. Bioact. Comp. Polymers* (1992) 7, 175–190). Work on a similar polymer consisting mainly of the closely related 2-hydroxypropyl derivative showed that it was endocytosed by the mononuclear phagocyte system only to a rather low extent (see Goddard, P., Williamson, I., Bron, J., Hutchkinson, L. E., Nicholls, J. and Petrak, K. in *J. Bioct. Compat. Polym.* (1991) 6, 4–24.).

Other potentially useful poymeric spacer materials include:

i) copolymers of methyl methacrylate with methacrylic acid; these may be erodible (see Lee, P. I. in *Pharm. Res.* (1993) 10, 980) and the carboxylate substituents may cause a higher degree of swelling than with neutral polymers;

ii) block copolymers of polymethacrylates with biodegradable polyesters (see e.g. San Roman, J. and Guillen-Garcia, P. in *Biomaterials* (1991) 12, 236–241);

iii) cyanoacrylates, i.e. polymers of esters of 2-cyanoacrylic acid—these are biodegradable and have been used in the form of nanoparticles for selective drug delivery (see Forestier, F., Gerrier, P., Chaumard, C., Quero, A. M., Couvreur, P. and Labarre, C. in *J. Antimicrob. Chemoter.* (1992) 30, 173–179);

iv) polyvinyl alcohols, which are water-soluble and generally regarded as biocompatible (see e.g. Langer, R. in *J. Control. Release* (1991) 16, 53–60);

v) copolymers of vinyl methyl ether with maleic anhydride, which have been stated to be bioerodible (see Finne, U., Hannus, M. and Urtti, A. in *Int. J. Pharm.* (1992) 78. 237–241);

vi) polyvinylpyrrolidones, e.g. with molecular weight less than about 25,000, which are rapidly filtered by the kidneys (see Hespe, W., Meier, A. M. and Blankwater, Y. M. in *Arzeim.-Forsch./Drug Res.* (1977) 27, 1158–1162);

vii) polymers and copolymers of short-chain aliphatic hydroxyacids such as glycolic, lactic, butyric, valeric and caproic acids (see e.g. Carli, F. in *Chim. Ind.* (Milan) (1993) 75, 494–9), including copolymers which incorporate aromatic hydroxyacids in order to increase their degradation rate (see Imasaki, K., Yoshida, M., Fukuzaki, H., Asano, M., Kumakura, M., Mashimo, T., Yamanaka, H. and Nagai. T. in *Int. J. Pharm.* (1992) 81, 31–38);

viii) polyesters consisting of alternating units of ethylene glycol and terephthalic acid, e.g. Dacron$^R$, which are non-degradable but highly biocompatible;

ix) block copolymers comprising biodegradable segments of aliphatic hydroxyacid polymers (see e.g. Younes, H., Nataf, P. R., Cohn, D., Appelbaum, Y. J., Pizov, G. and Uretzky, G. in *Biomater. Artif. Cells Artif. Organs* (1988) 16, 705–719), for instance in conjunction with polyurethanes (see Kobayashi, H., Hyon, S. H. and Ikada, Y. in "Water-curable and biodegradable prepolymers"—*J. Biomed. Mater. Res.* (1991) 25, 1481–1494);

x) polyurethanes, which are known to be well-tolerated in implants, and which may be combined with flexible "soft" segments, e.g. comprising poly(tetra methylene glycol), poly(propylene glycol) or poly(ethylene glycol)) and aromatic "hard" segments, e.g. comprising 4,4'-methylenebis(phenylene isocyanate) (see e.g. Ratner, B. D., Johnston, A. B. and Lenk, T. J. in *J. Biomed. Mater. Res: Applied Biomaterials* (1987) 21, 59–90; Sa Da Costa, V. et al. in *J. Coll. Interface Sci.* (1981) 80, 445–452 and Affrossman, S. et al. in *Clinical Materials* (1991) 8, 25–31);

xi) poly(1,4-dioxan-2-ones), which may be regarded as biodegradable esters in view of their hydrolysable ester linkages (see e.g. Song, C. X., Cui, X. M. and Schindler, A. in *Med. Biol. Eng. Comput.* (1993) 31, S147–150), and which may include glycolide units to improve their absorbability (see Bezwada, R. S., Shalaby, S. W. and Newman, H. D. J. in *Agricultural and synthetic polymers: Biodegradability and utilization* (1990) (ed Glass, J. E. and Swift, G.), 167–174—ACS symposium Series, #433, Washington D.C., U.S.A.—American Chemical Society);

xii) polyanhydrides such as copolymers of sebacic acid (octanedioic acid) with bis(4-carboxy-phenoxy)propane, which have been shown in rabbit studies (see Brem, H., Kader, A., Epstein, J. I., Tamargo, R. J., Domb, A., Langer, R. and Leong, K. W. in *Sel. Cancer Ther.* (1989) 5, 55–65) and rat studies (see Tamargo, R. J., Epstein, J. I., Reinhard, C. S., Chasin, M. and Brem, H. in *J. Biomed. Mater. Res.* (1989) 23, 253–266) to be useful for controlled release of drugs in the brain without evident toxic effects;

xiii) biodegradable polymers containing ortho-ester groups, which have been employed for controlled release in vivo (see Maa, Y. F. and Heller, J. in *J. Control. Release* (1990) 14, 21–28); and xiv) polyphosphazenes, which are inorganic polymers consisting of alternate phosphorus and nitrogen atoms (see Crommen, J. H., Vandorpe, J. and Schacht, E. H. in *J. Control. Release* (1993) 24, 167–180).

The following tables list linking agents and agents for protein modification which may be useful in preparing targetable contrast agents in accordance with the invention.

| Heterobifunctional linking agents | | | |
|---|---|---|---|
| Linking agent | Reactivity 1 | Reactivity 2 | Comments |
| ABH | carbohydrate | photoreactive | |
| ANB-NOS | —NH$_2$ | photoreactive | |
| APDP (1) | —SH | photoreactive | iodinable disulphide linker |
| APG | —NH$_2$ | photoreactive | reacts selectively with Arg at pH 7–8 |
| ASIB (1) | —SH | photoreactive | iodinable |
| ASBA (1) | —COOH | photoreactive | iodinable |
| EDC | —NH$_2$ | —COOH | zero-length linker |
| GMBS | —NH$_2$ | —SH | |
| sulfo-GMBS | —NH$_2$ | —SH | water-soluble |
| HSAB | —NH$_2$ | photoreactive | |
| sulfo-HSAB | —NH$_2$ | photoreactive | water-soluble |
| MBS | —NH$_2$ | —SH | |
| sulfo-MBS | —NH$_2$ | —SH | water-soluble |
| M$_2$C$_2$H | carbohydrate | —SH | |
| MPBH | carbohydrate | —SH | |
| NHS-ASA (1) | —NH$_2$ | photoreactive | iodinable |
| sulfo-NHS-ASA (1) | —NH$_2$ | photoreactive | water-soluble, iodinable |
| sulfo-NHS-LC-ASA (1) | —NH$_2$ | photoreactive | water-soluble, iodinable |
| PDPH | carbohydrate | —SH | disulphide linker |
| PNP-DTP | —NH$_2$ | photoreactive | |
| SADP | —NH$_2$ | photoreactive | disulphide linker |
| sulfo-SADP | —NH$_2$ | photoreactive | water-soluble disulphide linker |
| SAED | —NH$_2$ | photoreactive | disulphide linker |
| SAND | —NH$_2$ | photoreactive | water-soluble disulphide linker |
| SANPAH | —NH$_2$ | photoreactive | |
| sulfo-SANPAH | —NH$_2$ | photoreactive | water-soluble |
| SASD (1) | —NH$_2$ | photoreactive | water-soluble iodinable disulphide linker |
| SIAB | —NH$_2$ | —SH | |

-continued

Heterobifunctional linking agents

| Linking agent | Reactivity 1 | Reactivity 2 | Comments |
|---|---|---|---|
| sulfo-SIAB | —$NH_2$ | —SH | water-soluble |
| SMCC | —$NH_2$ | —SH | |
| sulfo-SMCC | —$NH_2$ | —SH | water-soluble |
| SMPB | —$NH_2$ | —SH | |
| sulfo-SMPB | —$NH_2$ | —SH | water-soluble |
| SMPT | —$NH_2$ | —SH | |
| sulfo-LC-SMPT | —$NH_2$ | —SH | water-soluble |
| SPDP | —$NH_2$ | —SH | |
| sulfo-SPDP | —$NH_2$ | —SH | water-soluble |
| sulfo-LC-SPDP | —$NH_2$ | —SH | water-soluble |
| sulfo-SAMCA (2) | —$NH_2$ | photoreactive | |
| sulfo-SAPB | —$NH_2$ | photoreactive | water-soluble |

Notes:
(1) = iodinable;
(2) = fluorescent

Homobifunctional linking agents

| Linking agent | Reactivity | Comments |
|---|---|---|
| O | —$NH_2$ | |
| BMH | —SH | |
| BASED (1) | photoreactive | iodinable disulphide linker |
| BSCOES | —$NH_2$ | |
| sulfo-BSCOES | —$NH_2$ | water-soluble |
| DFDNB | —$NH_2$ | |
| DMA | —$NH_2$ | |
| DMP | —$NH_2$ | |
| DMS | —$NH_2$ | |
| DPDPB | —SH | disulphide linker |
| DSG | —$NH_2$ | |
| DSP | —$NH_2$ | disulphide linker |
| DSS | —$NH_2$ | |
| DST | —$NH_2$ | |
| sulfo-DST | —$NH_2$ | water-soluble |
| DTBP | —$NH_2$ | disulphide linker |
| DTSSP | —$NH_2$ | disulphide linker |
| EGS | —$NH_2$ | |
| sulfo-EGS | —$NH_2$ | water-soluble |
| SPBP | —$NH_2$ | |

Biotinylation agents

| Agent | Reactivity | Comments |
|---|---|---|
| biotin-BMCC | —SH | |
| biotin-DPPE* | | preparation of biotinylated liposomes |
| biotin-LC-DPPE* | | preparation of biotinylated liposomes |
| biotin-HPDP | —SH | disulphide linker |
| biotin-hydrazide | carbohydrate | |
| biotin-LC-hydrazide | carbohydrate | |
| iodoacetyl-LC-biotin | —$NH_2$ | |
| NHS-iminobiotin | —$NH_2$ | reduced affinity for avidin |
| NHS-SS-biotin | —$NH_2$ | disulphide linker |
| photoactivatable biotin | nucleic acids | |
| sulfo-NHS-biotin | —$NH_2$ | water-soluble |
| sulfo-NHS-LC-biotin | —$NH_2$ | |

Notes:
DPPE = dipalmitoylphosphatidylethanolamine;
LC = long chain

Agents for protein modification

| Agent | Reactivity | Function |
|---|---|---|
| Ellman's reagent | —SH | quantifies/detects/protects |
| DTT | —S.S— | reduction |
| 2-mercaptoethanol | —S.S— | reduction |
| 2-mercaptylamine | —S.S— | reduction |
| Traut's reagent | —$NH_2$ | introduces —SH |
| SATA | —$NH_2$ | introduces protected —SH |
| AMCA—NHS | —$NH_2$ | fluorescent labelling |
| AMCA-hydrazide | carbohydrate | fluorescent labelling |
| AMCA-HPDP | —S.S— | fluorescent labelling |
| SBF-chloride | —S.S— | fluorescent detection of —SH |
| N-ethylmaleimide | —S.S— | blocks —SH |
| NHS-acetate | —$NH_2$ | blocks and acetylates —$NH_2$ |
| citraconic anhydride | —$NH_2$ | reversibly blocks and introduces negative charges |
| DTPA | —$NH_2$ | introduces chelator |
| BNPS-skatole | tryptophan | cleaves tryptophan residue |
| Bolton-Hunter | —$NH_2$ | introduces iodinable group |

Linking agents used in accordance with the invention will in general bring about linking of vector to reporter or reporter to reporter with some degree of specificity, and may also be used to attach one or more therapeutically active agents.

Ultrasound imaging modalities which may be used in accordance with the invention include two- and three-dimensional imaging techniques such as B-mode imaging (for example using the time-varying amplitude of the signal envelope generated from the fundamental frequency of the emitted ultrasound pulse, from sub-harmonics or higher harmonics thereof or from sum or difference frequencies derived from the emitted pulse and such harmonics, images generated from the fundamental frequency or the second harmonic thereof being preferred), colour Doppler imaging and Doppler amplitude imaging, and combinations of the two latter with any of the modalities (techniques) above. Surprisingly, the second harmonic signals from the targeted monolayer microspheres were found to be excellent when used in accordance with the present invention. To reduce the effects of movement, successive images of tissues such as the heart or kidney may be collected with the aid of suitable synchronisation techniques (e.g. gating to the ECG or respiratory movement of the subject). Measurement of changes in resonance frequency or frequency absorption which accompany arrested or retarded microbubbles may also usefully be made to detect the contrast agent.

The present invention provides a tool for therapeutic drug delivery in combination with vector-mediated direction of the product to the desired site. By "therapeutic" or "drug" is meant an agent having a beneficial effect on a specific disease in a living human or non-human animal. Whilst combinations of drugs and ultrasound contrast agents have been proposed in, for example, WO-A-9428873 and WO-A-9507072, these products lack vectors having affinity for particular sites and thereby show comparitively poor specific retention at desired sites prior to or during drug release.

Therapeutic compounds used in accordance with the present invention may be encapsulated in the interior of the microbubbles or attached to or incorporated in the encapsulating walls. Thus, the therapeutic compound may be linked to a part of the wall, for example through covalent or ionic bonds, or may be physically mixed into the encapsulating material, particularly if the drug has similar polarity or solubility to the membrane material, so as to prevent it from leaking out of the product before it is intended to act in the body. The release of the drug may be initiated merely by wetting contact with blood following administration or as a consequence of other internal or external influences, e.g. dissolution processes catalyzed by enzymes or the use of of ultrasound. The destruction of gas-containing microparticles using external ultrasound is a well known phenomenon in respect of ultrasound contrast agents, e.g. as described in WO-A-9325241; the rate of release may be varied depending on the type of therapeutic application, using a specific amount of ultrasound energy from the transducer.

The therapeutic agent may be covalently linked to the encapsulating membrane surface using a suitable linking agent, e.g. as described herein. Thus, for example, one may initially prepare a phospholipid or lipopeptide derivative to which the drug is bonded through a biodegradable or selectively cleavable linker followed by incorporation of the material into the microbubble. Alternatively lipidated drug molecules which do not require processing to liberate an active drug are incorporated directly into the membrane. The active lipidated-drug can be released by increasing the strength of the ultrasound beam.

Exemplary drug delivery systems suitable for use in the present compositions include any known therapeutic drugs or active analogues thereof containing thiol groups which are coupled to thiol containing microbubbles under oxidative conditions yielding disulphide bridges. In combination with a vector or vectors the drug/vector modified microbubbles are allowed to accumulate in the target tissue. Administration of a reducing agent such as reduced glutathione then liberates the drug molecule from the targeted microbubble in the vicinity of the target cell increasing the local concentration of the drug and enhancing therapeutic effect. The product may also be prepared without the therapeutic if desired. The drug may then be coupled to or coated on the microbubbles prior to use. Thus, for example, a therapeutic could be added to a suspension of microbubbles in aqueous media and shaken in order to attach or adhere the therapeutic to the microbubbles.

Other drug delivery systems include vector modified phospholipid membranes doped with lipopeptide structures comprising a poly-L-lysine or poly-D-lysine chain in combination with a targeting vector. Applied to gene therapy/antisense technologies with particular emphasis on receptor-mediated drug delivery the microbubble carrier is condensed with DNA or RNA via elecrostatic interaction with the polycation. This method has the advantage that the vector or vectors used for targeted delivery are not directly attached to the polysine carrier moiety. The polylysine chain is also anchored more tightly in the microbubble membrane due to the presence of the lipid chains. The use of ultrasound to increase the effectiveness of delivery is also considered useful.

Alternatively free polylysine chains are firstly modified with drug or vector molecules then condensed onto the negative surface of targeted microbubbles.

Representative and non-limiting examples of drugs useful in accordance with the invention include antineoplastic agents such as vincristine, vinblastine, vindesine, busulfan, chlorambucil, spiroplatin, cisplatin, carboplatin, methotrexate, adriamycin, mitomycin, bleomycin, cytosine arabinoside, arabinosyl adenine, mercaptopurine, mitotane, procarbazine, dactinomycin (antinomycin D), daunorubicin, doxorubicin hydrochloride, taxol, plicamycin, aminoglutethimide, estramustine, flutamide, leuprolide, megestrol acetate, tamoxifen, testolactone, trilostane, amsacrine (m-AMSA), asparaginase (L-asparaginase), etoposide, interferon a-2a and 2b, blood products such as hematoporphyrins or derivatives of the foregoing; biological response modifiers such as muramylpeptides; antifungal agents such as ketoconazole, nystatin, griseofulvin, flucytosine, miconazole or amphotericin B; hormones or hormone analogues such as growth hormone, melanocyte stimulating hormone, estradiol, beclomethasone dipropionate, betamethasone, cortisone acetate, dexamethasone, flunisolide, hydrocortisone, methylprednisolone, paramethasone acetate, prednisolone, prednisone, triamcinolone or fludrocortisone acetate; vitamins such as cyanocobalamin or retinoids; enzymes such as alkaline phosphatase or manganese superoxide dismutase; antiallergic agents such as amelexanox; inhibitors of tissue factor such as monoclonal antibodies and Fab fragments thereof, synthetic peptides, nonpeptides and compounds down-regulating tissue factor expression; inhibitors of platelets such as, GPIa, GPIb and GPIIb-IIIa, ADP receptors, thrombin receptors, von Willebrand factor, prostaglandins, aspirin, ticlopidin, clopigogrel and reopro; inhibitors of coagulation protein targets such as: FIIa FVa, FVIIa, FVIIIA, FIXa, tissue factor, hepatins, hirudin, hirulog, argatroban, DEGR-rFVIIa and annexin V; inhibitors of fibrin formation and promoters of fibrinolysis such as t-PA, urokinase, Plamin, Streptokinase, rt-Plasminogen Activator and rStaphylokinase; antiangiogenic factors such as medroxyprogesteron, pentosan polysulphate, suramin, taxol, thalidomide, angiostatin, interferon-alpha, metalloproteinase inhibitors, platelet factor 4, somatostatin, thromobospondin; circulatory drugs such as propranolol; metabolic potentiators such as glutathione; antituberculars such as p-aminosalicylic acid, isoniazid, capreomycin sulfate, cyclosexine, ethambutol, ethionamide, pyrazinamide, rifampin or streptomycin sulphate; antivirals such as acyclovir, amantadine, azidothymidine, ribavirin or vidarabine; blood vessel dilating agents such as diltiazem, nifedipine, verapamil, erythritol tetranitrate, isosorbide dinitrate, nitroglycerin or pentaerythritol tetranitrate; antibiotics such as dapsone, chloramphenicol, neomycin, cefaclor, cefadroxil, cephalexin, cephradine, erythromycin, clindamycin, lincomycin, amoxicillin, ampicillin, bacampicillin, carbenicillin, dicloxacillin, cyclacillin, picloxacillin, hetacillin, methicillin, nafcillin, penicillin, polymyxin or tetracycline; antiinflammatories such as diflunisal, ibuprofen, indomethacin, meclefenamate, mefenamic acid, naproxen, phenylbutazone, piroxicam, tolmetin, aspirin or salicylates; antiprotozoans such as chloroquine, metronidazole, quinine or meglumine antimonate; antirheumatics such as penicillamine; narcotics such as paregoric; opiates such as codeine, morphine or opium; cardiac glycosides such as deslaneside, digitoxin, digoxin, digitalin or digitalis; neuromuscular blockers such as atracurium mesylate, gallamine triethiodide, hexafluorenium bromide, metocurine iodide, pancuronium bromide, succinylcholine chloride, tubocurarine chloride or vecuronium bromide; sedatives such as amobarbital, amobarbital sodium, apropbarbital, butabarbital sodium, chloral hydrate, ethchlorvynol, ethinamate, flurazepam hydrochloride, glutethimide, methotrimeprazine hydrochloride, methyprylon, midazolam hydrochloride, paraldehyde, pentobarbital, secobarbital sodium, talbutal, temazepam or triazolam;

local anaesthetics such as bupivacaine, chloroprocaine, etidocaine, lidocaine, mepivacaine, procaine or tetracaine; general anaesthetics such as droperidol, etomidate, fentanyl citrate with droperidol, ketamine hydrochloride, methohexital sodium or thiopental and pharmaceutically acceptable salts (e.g. acid addition salts such as the hydrochloride or hydrobromide or base salts such as sodium, calcium or magnesium salts) or derivatives (e.g. acetates) thereof. Other examples of therapeutics include genetic material such as nucleic acids, RNA, and DNA of natural or synthetic origin, including recombinant RNA and DNA. DNA encoding certain proteins may be used in the treatment of many different types of diseases. For example, tumor necrosis factor or interleukin-2 genes may be provided to treat advanced cancers; thymidine kinase genes may be provided to treat ovarian cancer or brain tumors; interleukin-2 genes may be provided to treat neuroblastoma, malignant melanoma or kidney cancer; and interleukin-4 genes may be provided to treat cancer.

Lipophilic derivatives of drugs linked to the microbubble wall through hydrophobic interactions may exhibit therapeutic effects as part of the microbubble or after release from the microbubble, e.g. by use of ultrasound. If the drug does not possess the desired physical properties, a lipophilic group may be introduced for anchoring the drug to the membrane. Preferably the lipophilic group should be introduced in a way that does not influence the in vivo potency of the molecule, or the lipophilic group may be cleaved releasing the active drug. Lipophilic groups may be introduced by various chemical means depending on functional groups available in the drug molecule. Covalent coupling may be effected using functional groups in the drug molecule capable of reacting with appropriately functionalised lipophilic compounds. Examples of lipophilic moieties include branched and unbranched alkyl chains, cyclic compounds, aromatic residues and fused aromatic and non-aromatic cyclic systems. In some instances the lipophilic moiety will consist of a suitably functionalised steroid, like cholesterol and related compounds. Examples of functional groups particularly suitable for derivatisation include nucleophilic groups like amino, hydroxy and sulfhydryl groups. Suitable processes for lipophilic derivatisation of any drug containing a sulfhydryl group, like captopril, may include direct alkylation, e.g. reaction with an alkyl halide under basic conditions and thiol ester formation by reaction with an activated carboxylic acid. Representative examples of derivatisation of any drug having carboxylic functions, like atenolol and chlorambucil, include amide and ester formation by coupling of amines and alcohols, respectively, possesing requested physical properties. A preferred aspect is attachment of cholesterol to a therapeutic compound by forming a degradable ester bond.

A preferred application of the present invention relates to angiogenesis, which is the formation of new blood vessels by branching from existing vessels. The primary stimulus for this process may be inadequate supply of nutrients and oxygen (hypoxia) to cells in a tissue. The cells may respond by secreting angiogenetic factors, of which there are many; one example is vascular endothelial growth factor. These factors initiate the secretion of proteolytic enzymes which break down the proteins of the basement membrane, as well as inhibitors which limit the action of these potentially harmful enzymes. The combined effect of loss of attachment and signals from the receptors for angiogenetic factors is to cause the endothelial cells to move, multiply, and rearrange themselves, and finally to synthetise a basement membrane around the new vessels.

Tumors must initiate angiogenesis when they reach millimeter size in order to keep up their rate of growth. As angiogenesis is accompanied by characteristic changes in the endothelial cells and their environment, this process is a promising target for therapeutic intervention. The transformations accompanying angiogenesis are also very promising for diagnosis, a preferred example being malignant disease, but the concept also shows great promise in inflammation and a variety of inflammation-related diseases. These factors are also involved in re-vascularisation of infarcted parts of the myocardium, which occurs if a stenosis is released within a short time.

A number of known receptors/targets associated with angiogenesis are given in subsequent tables. Using the targeting principles described in the present disclosure, angiogenesis mav be detected by the majority of the imaging modalities in use in medicine. Contrast-enhanced ultrasound may possess additional advantages, the contrast medium being microspheres which are restricted to the interior of blood vessels. Even if the target antigens are found on many cell types, the microspheres will attach exclusively to endothelial cells.

So-called prodrugs may also be used in agents according to the invention. Thus drugs may be derivatised to alter their physicochemical properties and to adapt them for inclusion into the reporter; such derivatised drugs may be regarded as prodrugs and are usually inactive until cleavage of the derivatising group regenerates the active form of the drug.

By targeting a gas-filled microbubble containing a prodrug-activating enzyme to areas of pathology one may image targeting of the enzyme, making it possible to visualise when the micobubbles are targeted properly to the area of pathology and at the same time have disappeared from non-target areas. In this way one can determine the optimal time for injection of prodrug into individual patients.

Another alternative is to incorporate the prodrug, the prodrug-activating enzyme and the vector in the same microbubble in a system where the prodrug will only be activated after some external stimulus. Such a stimulus may, for example, be a tumour-specific protease as described above, or bursting of the bubbles by external ultrasound after the desired targeting has been achieved.

Therapeutics may easily be delivered in accordance with the invention to diseased or necrotic areas including the heart and vasculature in general, and to the liver, spleen and kidneys and other regions such as the lymph system, body cavities or gastrointestinal system.

Products according to the present invention may be used for targeted therapeutic delivery either in vivo or in vitro. In the latter context the products may be useful in in vitro systems such as kits for diagnosis of different diseases or characterisation of different components in blood or tissue samples. Similar techniques to those used to attach certain blood components or cells to polymer particles(e.g. mono-disperse magnetic particles) in vitro to separate them from a sample may be used in the present invention, using the low density of the reporter units in agents of the present invention to effect separation of the gas-containing material by floatation and repeated washing.

Vectors which may be usefully employed in generating multiple-specific targetable contrast agents according to the invention include the following:
  i) Antibodies, which can be used as vectors for a very wide range of targets, and which have advantageous properties such as very high specificity, high affinity (if desired), the possiblity of modifying affinity according to need etc. Whether or not antibodies will be bioactive will depend on the specific vector/target combination. Both conventional and genetically engineered antibodies may be employed, the latter permitting engineering of antibodies to particular needs, e.g. as regards affinity and specificity. The use of human antibodies may be preferred to avoid possible immune reactions against the vector molecule. A further useful class of antibodies comprises so-called bispecific antibodies, i.e. antibodies having specificity for two different target molecules in one antibody molecule. Such antibodies may, for example, be useful in promoting formation of bubble clusters and may also be used for various therapeutic purposes, e.g. for carrying toxic moieties to the target. Various aspects of bispecific antibodies are described by McGuinness, B. T. et al. in *Nat. Biotechnol.* (1996) 14, 1149–1154; by George, A. J. et al. in *J. Immunol.* (1994) 152, 1802–1811; by Bonardi et al. in *Cancer Res.* (1993) 53, 3015–3021; and by French, R. R. et al. in *Cancer Res.* (1991) 51, 2353–2361.

ii) Cell adhesion molecules, their receptors, cytokines, growth factors, peptide hormones and pieces thereof. Such vectors rely on normal biological protein-protein interactions with target molecule receptors, and so in many cases will generate a biological response on binding with the targets and thus be bioactive; this may be a relatively insignificant concern with vectors which target proteoglycans.

iii) Non-peptide agonists/antagonists or non-bioactive binders of receptors for cell adhesion molecules, cytokines, growth factors and peptide hormones. This category may include non-bioactive vectors which will be neither agonists nor antagonist but which may nonetheless exhibit valuable targeting ability.

iv) Oligonucleotides and modified oligonucleotides which bind DNA or RNA through Watson-Crick or other types of base-pairing. DNA is usually only present in extracelluar space as a consequence of cell damage, so that such oligonucleotides, which will usually be non-bioactive, may be useful in, for example, targeting of necrotic regions, which are associated with many different pathological conditions. Oligonucleotides may also be designed to bind to specific DNA- or RNA-binding proteins, for example transcription factors which are very often highly overexpressed or activated in tumour cells or in activated immune or endothelial cells. Combinatorial libraries may be used to select oligonucleotides which bind specifically to possible target molecules (from proteins to caffeine) and which therefore may be employed as vectors for targeting.

v) DNA-binding drugs may behave similarly to oligonuclotides, but may exhibit biological acitvity and/or toxic effects if taken up by cells.

vi) Various small molecules, including bioactive compounds known to bind to biological receptors of various kinds. Such vectors or their targets may be used to generate non-bioactive compounds binding to the same targets.

vii) Vector molecules may be selected from combinatorial libraries without necessarily knowing the exact molecular target, by functionally selecting (in vitro, ex vivo or in vivo) for molecules binding to the region/structure to be imaged.

viii) Various small molecules, including bioactive compounds known to bind to biological receptors of various kinds. Such vectors or their targets may be used for generate non-bioactive compounds binding to the same targets.

ix) Proteins or peptides which bind to glucosaminoglycan side chains e.g. haparan sulphate, including glucosoaminoglycan-binding portions of larger molecules, since binding to such glucosoaminoglycans side chains does not result in a biological response. Proteoglycans are not found on red blood cells, thus eliminating undesirable adsorption to these cells.

Other peptide vectors and lipopeptides thereof of particular interest for targeted ultrasound imaging are listed below: Atherosclerotic plaque binding peptides such as YRALVDTLK (SEQ ID NO:22), YAKFRETLEDTRDRMY (SEQ ID NO:23) and RALVDTEFKVKQEAGAK (SEQ ID NO:24); Thrombus binding peptides such as NDGDFEEIPEEYLQ (SEQ ID NO:25) and GPRG (SEQ ID NO:26); Platelet binding peptides such as PLYKKIIKKLLES (SEQ ID NO:27); and cholecystokinin, α-melanocyte-stimulating hormone, heat stable enterotoxin 1, vasoactive intestinal peptide, synthetic alpha-M2 peptide from the third heavy chain complementarity-determining region and analogues thereof for tumor targeting.

The following tables identify various receptors which may be targeted by particular types of vectors and consequent areas of use for targetable ultrasound contrast agents according to the invention which contain such vectors.

| | Protein and peptide vectors - antibodies | | |
|---|---|---|---|
| Vector type | Receptor | Comments/areas of use | Ref |
| antibodies (general) | CD34 | vascular diseases in general, normal vessel wall (e.g myocardium), activated endothelium, immune cells | |
| " | ICAM-1 | vascular diseases in general, normal vessel wall (e.g myocardium), activated endothelium, immune cells | |
| " | ICAM-2 | vascular diseases in general, normal vessel wall (e.g myocardium), activated endothelium, immune cells | |
| " | ICAM-3 | vascular diseases in general, normal vessel wall (e.g | |

-continued

Protein and peptide vectors - antibodies

| Vector type | Receptor | Comments/areas of use | Ref |
|---|---|---|---|
| " | E-selectin | myocardium), activated endothelium, immune cells vascular diseases in general, normal vessel wall (e.g myocardium), activated endothelium, immune cells | |
| " | P-selectin | vascular diseases in general, normal vessel wall (e.g myocardium), activated endothelium, immune cells | |
| " | PECAM | vascular diseases in general, normal vessel wall (e.g myocardium), activated endothelium, immune cells | |
| " | Integrins, e.g. VLA-1, VLA-2, VLA-3 VLA-4, VLA-5, VLA-6, $\beta_1\alpha_7$, $\beta_1\alpha_8$, $\beta_1\alpha_v$, LFA-1, Mac-1, CD41a, etc. | vascular diseases in general, normal vessel wall (e.g myocardium), activated endothelium, immune cells | |
| " | GlyCAM | Vessel wall in lymph nodes (quite specific for lymph nodes) | |
| " | MadCam 1 | Vessel wall in lymph nodes (quite specific for lymph nodes) | |
| " | fibrin | Thrombi | |
| " | Tissue Factor | Activated endothelium, tumours | |
| " | Myosin | Necrosis, myocardial infaction | |
| " | CEA (carcinoem bryonal antigen) | Tumours | |
| " | Mucins | Tumours | |
| " | Multiple drug resistance protein | Tumours | |
| | Prostate specific antigen | Prostate cancer | |
| " | Cathepsin B | Tumours (proteases of various kinds are often more or less specifically overexpressed in a variety of tumours - Cathepsin B is such a protease) | |
| " | Transferrin receptor | Tumors, vessel wall | |
| MoAb 9.2.27 | | Tumours Antigen upregulated on cell growth | |
| | VAP-1 | Adhesion molecule | |
| | Band 3 protein | Upregulated during phagocytic activity | |
| | CD44 | tumor cells | |
| | $\beta_2$-microglobulin | general | |
| | MHC class I | general | |
| antibody | integrin $\alpha v\beta 3$ | tumors, angiogenisis | c |
| antibodies | CD44 | tumour cells | a |
| antibodies | $\beta_2$-microglobulin | general | b |
| antibodies | MHC class I | general | b | a.) Heider, K. H., M. Sproll, S. Susani, E. Patzelt, P. Beaumier, E. Ostermann, H. Ahorn, and G. R. Adolf. 1996. "Characterization of a high-affinity monoclonal antibody specific for CD44v6 as candidate for immunotherapy of squamous cell carcinomas". *Cancer Immunology Immunotherapy* 43: 245–253.

b). I. Roitt, J. Brostoff, and D. Male. 1985. *Immunology*, London: Gower Medical Publishing, p. 4.7 c.) Stromblad, S., and D. A. Cheresh. 1996. "Integrins, angiogenesis and vascular cell survival". *Chemistry & Biology* 3: 881–885.

| Protein and peptide vectors - cell adhesion molecules etc. | | | |
|---|---|---|---|
| Vector type | Receptor | Comments/areas of use | Ref |
| L-selectin | CD34 MadCAM1 GlyCam 1 | vascular diseases in general, normal vessel wall (e.g myocardium), activated endothelium, Lymph nodes | |
| Other selectins | carbohydrate ligands (sialyl Lewis x) heparan sulfate | vascular diseases in general, normal vessel wall (e.g myocardium), activated endothelium | |
| RGD-peptides | integrins | angiogenisis | |
| PECAM | PECAM, and other | Endothelium, Cells in immune system | |
| Integrins, e.g. VLA-1, VLA-2, VLA-3, VLA-4, VLA-5, VLA-6, $\beta_1\alpha_7$, $\beta_1\alpha_8$, $\beta_1\alpha_v$, LFA-1, Mac-1, CD41a, etc. | Laminin, collagen, fibronectin, VCAM-1, thrombo-spondin, vitronectin etc. | Endothelium, Vessel wall etc. | |
| Integrin receptors, e.g. Laminin, collagen, fibronectin, VCAM-1, thrombospondin, vitronectin etc. | Integrins, e.q. VLA-1, VLA-2, VLA-3, VLA-4, VLA-5, VLA-6, $\beta_1\alpha_7$, $\beta_1\alpha_8$, $\beta_1\alpha_v$, LFA-1, Mac-1, CD41a, etc. | Cells in immune system vessel wall etc. | |
| Nerve cell adhesion molecule (N-CAM) | proteoglycans N-CAM (homophilic) | | |
| RGD-peptides | integrins | angiogenesis | c |

| Vectors comprising cytokines/growth factors/peptide hormones and fragments thereof | | | |
|---|---|---|---|
| Vector type | Receptor | Comments/areas of use | Ref |
| Epidermal growth factor | EGF-receptor or related receptors | Tumours | |
| Nerve growth factor | NGF-receptor | Tumours | |
| Somatostatin | ST-receptor | Tumours | |
| Endothelin | Endothelin-receptor | Vessel wall | |
| Interleukin-1 | IL-1-receptor | Inflammation, activated cells of different kinds | |
| Interleukin-2 | IL-2-receptor | Inflammation, activated cells of different kinds | |
| Chemokines (ca. 20 different cytokines partly sharing receptors) | Chemokine receptors, proteoglycans | Inflammation | |
| Tumour necrosis factor | TNF-receptors | Inflammation | |
| Parathyroid hormone | PTH-receptors | Bone diseases Kidney diseases | |
| Bone Morphogenetic Protein | BMP-receptors | Bone Diseases | |
| Calcitonin | CT-receptors | Bone diseases | |
| Colony stimulating factors (G-CSF, GM-CSF, M-CSF, IL-3) | Corresponding specific receptors, proteoglycans | Endothelium | |
| Insulin like growth factor I | IGF-I receptor | Tumours, other growing tissues | |
| Atrial Natriuretic Factor | ANF-receptors | Kidney, vessel wall | |
| Vasopressin | Vasopressin receptor | Kidney, vessel wall | |
| VEGF | VEGF-receptor | Endothelium, regions of angiogenesis | |
| Fibroblast growth factors | FGF-receptors, Proteoglycans | Endothelium Angiogenesis | |
| Schwann cell growth factor | proteoglycans specific receptors | | |

| Miscellaneous protein and peptide vectors | | | |
|---|---|---|---|
| Vector type | Receptor | Comments/areas of use | Ref |
| Streptavidin | Kidney | Kidney diseases | |
| Bacterial fibronectin-binding proteins | Fibronectin | Vessel wall | |
| Fc-part of antibodies | Fc-receptors | Monocytes macrophages liver | |
| Transferrin | transferrin-receptor | Tumours vessel walls | |
| Streptokinase/ tissue plasminogen activator | thrombi | thrombi | |
| Plasminogen, plasmin | Fibrin | Thrombi, tumours | |
| Mast cell proteinases | proteoglycans | | |
| Elastase | proteoglycans | | |
| Lipoprotein lipase | proteoglycans | | |
| Coagulation enzymes | proteoglycans | | |
| Extracellular superoxide dismutase | proteoglycans | | |
| Heparin cofactor II | proteoglycans | | |
| Retinal survival factor | proteoglycans specific receptors | | |
| Heparin-binding brain mitogen | proteoglycans specific receptors | | |
| Apolipoprotein, e.g. apolipoprotein B | proteoglycans specific receptors (e.g., LDL receptor) | | |
| Apolipoprotein E | LDL receptor proteoglycans | | |
| Adhesion-promoting proteins, e.g. Purpurin | | proteoglycans | |
| Viral coat proteins, | | proteoglycans | |

Miscellaneous protein and peptide vectors

| Vector type | Receptor | Comments/areas of use | Ref |
|---|---|---|---|
| e.g. HIV, Herpes | | | |
| Microbial adhesins | "Antigen 85" complex of mycobacteria | fibronectin, collagen, fibrinogen, vitronectin, heparan sulfate | |
| β-amyloid precursor | proteoglycans | β-amyloid accumulates in Alzheimer's disease | |
| Tenascin, e.g. tenascin C | heparan sulfate, integrins | | |

Vectors comprising non-peptide agonists/antagonists of cytokines/growth factors/peptide hormones/cell adhesion molecules

| Vector type | Receptor | Comments/areas of use | Ref |
|---|---|---|---|
| Endothelin antagonist | Endothelin receptor | Vessel wall | |
| Desmopressin (vasopressin analogue) | Vasopressin receptor | Kidney Vessel wall | |
| Demoxytocin (oxytocin analogue) | Oxytocin Receptor | Reproductive organs, Mammary glands, Brain | |
| Angiotensin II receptor antagonists CV-11974, TCV-116 | Angiotensin II receptors | Vessel wall brain adrenal gland | |
| non-peptide RGD-analogues | integrins | Cells in immune system vessel wall etc. | |

Vectors comprising anti-angiogenic factors

| Vector type | Target | Comments/areas of use | Ref |
|---|---|---|---|
| Angiostatin | EC of tumors | plasminogen fragment | K |
| cartilage-derived inhibitor | EC of tumors | | J |
| β-Cyclodextrin tetradecasulfate | tumors, inflammation | | C |
| fumagillin and analogs | tumors, inflammation | | E |
| Interferon-α | EC of tumors | | K |
| Interferon-γ | EC of tumors | | E |
| interleukin-12 | EC of tumors | | E |
| linomide | tumors, inflammation | | A |
| medroxyprogesterone | EC of tumors | | K |
| metalloproteinase inhibitors | EC of tumors | | K |
| pentosan polysulfate | EC of tumors | | K |
| platelet factor 4 | EC of tumors | | M |
| Somatostatin | EC of tumors | | K |
| Suramin | EC of tumors | | K |
| Taxol | EC of tumors | | K |
| thalidomide | EC of tumors | | K |
| Thrombospondin | EC of tumors | | K |

Vectors comprising angiogenic factors

| Vector type | Target | Comments/areas of use | Ref |
|---|---|---|---|
| acidic fibroblast growth factor | EC of tumors | | K |
| adenosine | EC of tumors | | K |
| Angiogenin | EC of tumors | | K |
| Angiotensin II | EC of tumors | | K |
| basement membrane components | tumors | e.g., tenascin, collagen IV | M |
| basic fibroblast growth factor | EC of tumors | | K |
| Bradykinin | EC of tumors | | K |
| Calcitonin gene-related peptide | EC of tumors | | K |
| epidermal growth factor | EC of tumors | | K |
| Fibrin | tumors | | K |
| Fibrinogen | tumors | | K |
| Heparin | EC of tumors | | K |
| histamine | EC of tumors | | K |
| hyaluronic acid or fragments thereof | EC of tumors | | K |
| Interleukin-1α | EC of tumors | | K |
| laminin, laminin fragments | EC of tumors | | K |
| nicotinamide | EC of tumors | | K |
| platelet activating factor | EC of tumors | | K |
| platelet-derived endothelial growth factor | EC of tumors | | K |
| prostaglandins E1, E2 | EC of tumors | | K |
| spermine | EC of tumors | | K |
| spermine | EC of tumors | | K |
| Substance P | EC of tumors | | K |
| transforming growth factor-α | EC of tumors | | K |
| transforming growth factor-β | EC of tumors | | K |
| Tumor necrosis factor-β | EC of tumors | | K |
| vascular endothelial growth factor/vascular permeability factor | EC of tumors | | K |
| vitronectin | | | A |

Vector molecules other than recognized angiogenetic factors with known affinity for receptors associated with angiogenesis

| Vector type | Target | Comments/areas of use | Ref |
|---|---|---|---|
| angiopoietin | tumors, inflammation | | B |
| α₂-antiplasmin | tumors, inflammation | | |
| combinatorial libraries, compounds from | tumors, inflammation | for instance: compounds that bind to basement membrane after degradation | |
| endoglin | tumors, inflammation | | D |
| endosialin | tumors, inflammation | | D |
| endostatin [collagen fragment] | tumors, inflammation | | M |
| Factor VII related antigen | tumors, inflammation | | D |
| fibrinopeptides | tumors, inflammation | | ZC |
| fibroblast growth factor, basic | tumors, inflammation | | E |
| hepatocyte growth factor | tumors, inflammation | | I |
| insulin-like growth factor | tumors, inflammation | | R |
| interleukins | tumors, inflammation | e.g.,: IL-8 | I |
| leukemia inhibitory | tumors, | | A |

-continued

Vector molecules other than recognized angiogenetic factors with known affinity for receptors associated with angiogenesis

| Vector type | Target | Comments/areas of use | Ref |
|---|---|---|---|
| factor | inflammation | | |
| metalloproteinase inhibitors | tumors, inflammation | e.g., batimastat | E |
| Monoclonal antibodies | tumors, inflammation | for instance: to angiogenetic factors or their receptors, or to components of the fibrinolytic system | |
| peptides, for instance cyclic RGD$_D$FV | tumors, inflammation | | B, Q |
| placental growth factor | tumors, inflammation | | J |
| placental proliferin-related protein | tumors, inflammation | | E |
| plasminogen | tumors, inflammation | | M |
| plasminogen activators | tumors, inflammation | | D |
| plasminogen activator inhibitors | tumors, inflammation | | U, V |
| platelet activating factor antagonists | tumors, inflammation | inhibitors of angiogenesis | A |
| platelet-derived growth factor | tumors, inflammation | | E |
| pleiotropin | tumors, inflammation | | ZA |
| proliferin | tumors, inflammation | | E |
| proliferin related protein | tumors, inflammation | | E |
| selectins | tumors, inflammation | e.g., E-selectin | D |
| SPARC | tumors inflammation | | M |
| snake venoms (RGD-containing) | tumors, inflammation | | Q |
| Tissue inhibitor of metalloproteinases | tumors, inflammation | e g., TIMP-2 | U |
| thrombin | tumors, inflammation | | H |
| thrombin-receptor-activating tetra-decapeptide | tumors, inflammation | | H |
| thymidine phosphorylase | tumors, inflammation | | D |
| tumor growth factor | tumors, inflammation | | ZA |

-continued

Receptors/targets associated with angiogenesis

| Vector type | Target | Comments/areas of use | Ref |
|---|---|---|---|
| biglycan | tumors, inflammation | dermatan sulfate proteoglycan | X |
| CD34 | tumors, inflammation | | L |
| CD44 | tumors, inflammation | | F |
| collagen type I, IV, VI, VIII | tumors, inflammation | | A |
| decorin | tumors, inflammation | dermatan sulfate proteoglycan | Y |
| dermatan sulfate proteoglycans | tumors, inflammation | | X |
| endothelin | tumors, inflammation | | G |
| endothelin receptors | tumors, inflammation | | G |
| fibronectin | tumors | | P |
| Flk-1/KDR, Flt-4 | tumors, inflammation | VEGF receptor | D |
| FLT-1 (fms-like tyrosine kinase) | tumors, inflammation | VEGF-A receptor | O |
| heparan sulfate | tumors, inflammation | | P |
| hepatocyte growth factor receptor (c-met) | tumors, inflammation | | I |
| insulin-like growth factor/mannose-6-phosphate receptor | tumors, inflammation | | R |
| integrins: $\beta_3$ and $\beta_5$, integrin $\alpha_V\beta_3$, integrin $\alpha_6\beta_1$, integrins $\alpha_6$, integrins $\beta_1$, integrin $\alpha_2\beta_1$, integrin $\alpha_V\beta_3$, integrin $\alpha_5$ integrin $\alpha_V\beta_5$, fibrin receptors. | Tumors, inflammation | laminin receptor subunit of the fibronectin receptor | D, P |
| Intercellular adhesion molecule-1 and -2 | tumors, inflammation | | P |
| Jagged gene product | tumors, inflammation | | T |
| Ly-6 | tumors, inflammation | a lymphocyte activation protein | N |
| matrix metalloproteinases | tumors, inflammation | | D |
| MHC class II | tumors, inflammation | | |
| Notch gene product | tumors, inflammation | | T |
| Osteopontin | tumors | | Z |
| PECAM | tumors, inflammation | alias CD31 | P |
| plasminogen activator receptor | tumors, inflammation | | ZC |
| platelet-derived growth factor receptors | tumors, inflammation | | E |
| Selectins: E-, P- | tumors, inflammation | | D |
| Sialyl Lewis-X | tumors, inflammation | blood group antigen | M |
| stress proteins: glucose regulated, heat shock families and others | tumors, inflammation | molecular chaperones | |
| syndecan | tumors, inflammation | | T |
| thrombospondin | tumors, inflammation | | M |
| TIE receptors | tumors, inflammation | tyrosine kinases with Ig- and EGF-like domains | E |
| tissue factor | tumors, inflammation | | Z |
| tissue inhibitor of metalloproteinases | tumors, inflammation | e.g., TIMP-2 | U |
| transforming growth factor receptor | tumors, inflammation | | E |
| urokinase-type plasminogen activator receptor | tumors, inflammation | | D |
| Vascular cellular adhesion molecule (VCAM) | tumors, inflammation | | D |
| Vascular endothelial growth factor related protein | tumors, inflammation | | |
| Vascular endothelial | tumors, | | K |

-continued

Receptors/targets associated with angiogenesis

| Vector type | Target | Comments/areas of use | Ref |
|---|---|---|---|
| growth factor-A receptor | inflammation | | |
| von Willebrand factor-related antigen | tumors, inflammation | | L |

Oligonucleotide vectors

| Vector type | Receptor | Comments/areas of use | Ref |
|---|---|---|---|
| Oligonucleotides complementary to repeated sequences, e.g. genes for ribosomal RNA, Alu-sequences | DNA made available by necrosis | Tumours Myocardial infection All other diseases that involves necrosis | |
| Oligonucleotides complementary to disease-specific mutations (e.g. mutated oncogenes) | DNA made available by necrosis in a region of the relevant disease | Tumours | |
| Oligonucleotides complementary to DNA of infecting agent. | DNA of infective agent | Viral or bacterial infections | |
| Triple or quadruple-helix forming oligonucleotides | As in above examples | As in above examples | |
| Oligonucleotides with recognition sequence for DNA- or RNA-binding proteins | DNA-binding protein, e.g. transcription factors (often overexpressed/ activated in tumours or activated endothelium/ immune cells | Tumours Activated endothelium Activated immune cells | |

Modified oligonucleotide vectors

| Vector type | Receptor | Comments/areas of use | Ref |
|---|---|---|---|
| Phosphorothioate oligos | As for unmodified oligos | As for unmodified oligos | |
| 2'-O-methyl substituted oligos | As for unmodified oligos | As for unmodified oligos | |
| circular oligos | As for unmodified oligos | As for unmodified oligos | |
| oligos containing hairpin structure to decrease degradation | As for unmodified oligos | As for unmodified oligos | |
| oligos with terminal phosphorothioate | As for unmodified oligos | As for unmodified oligos | |
| 2'-fluoro oligos | As for unmodified oligos | As for unmodified oligos | |
| 2'-amino oligos | As for unmodified oligos | As for unmodified oligos | |

-continued

Modified oligonucleotide vectors

| Vector type | Receptor | Comments/areas of use | Ref |
|---|---|---|---|
| DNA-binding drugs conjugated to oligos (for examples, see below) | As for unmodified oligos | Increased binding affinity as compared to pure oligos | |
| Peptide Nucleic Acids (PNAs, oligonucleotidss with a peptide backbone) | As for unmodified oligos | Increased binding affinity and stability compared to standard oligos. | |

Nucleoside and nucleotide vectors

| Vector type | Receptor | Comments/areas of use | Ref |
|---|---|---|---|
| Adenosine or analogues | Adenosine receptors | Vessel wall Heart | |
| ADP, UDP, UTP and others | Various nucleotide receptors | Many tissues e.g. brain, spinal cord, kidney, spleen | |

Receptors comprising DNA-binding drugs

| Vector type | Receptor | Comments/areas of use | Ref |
|---|---|---|---|
| acridine derivatives distamycin netropsin actinomycin D echinomycin bleomycin etc. | DNA made available by necrosis | Tumours, Myocardial infarction and all other diseases involving necrosis or other processes liberating DNA from cells | |

Receptors comprising protease substrates

| Vector type | Receptor | Comments/areas of use | Ref |
|---|---|---|---|
| Peptidic or non-peptidic substrates | Cathepsin B | Tumours, a variety of which may more or less specifically overexpress proteases of various kinds, e.g. Cathepsin B | |

Receptors comprising protease inhibitors

| Vector type | Receptor | Comments/areas of use | Ref |
|---|---|---|---|
| Peptidic or non-peptidic inhibitors e.g. N-acetyl-Leu—Leu-norleucinal | Cathepsin B | Tumours, a variety of which may more or less specifically overexpress proteases of various kinds, e.g. Cathepsin B | |
| bestatin ([(2S,3R)-3-Amino-2-hydroxy-4-phenyl- | Amino-peptidases | Tumours, e.g. on cell surfaces | |

-continued

Receptors comprising protease inhibitors

| Vector type | Receptor | Comments/areas of use | Ref |
|---|---|---|---|
| butanoyl]-L-leucine hydrochloride) | | | |
| Pefabloc (4-(2-aminoethyl)-benzenesulfonyl fluoride hydrochloride) | Serine proteases | Tumours, vessel wall etc. | |
| Commercially available inhibitors e.g. kaptopril enalapril ricionopril | Angiotensin converting enzyme | Endothelial cells | |
| Low specificity non-peptidic compounds | Coagulation factors | Vessel wall injury, tumours, etc. | |
| Protease nexins (extracellular protease inhibitors) | proteoglycans | | |
| Antithrombin | proteoglycans, Coagulation factors | | |

Vectors from combinatorial libraries

| Vector type | Receptor | Comments/areas of use | Ref |
|---|---|---|---|
| Antibodies with structure determined during generation process | Any of above targets - or may be unknown when make functional selection of vector binding to chosen diseased structure | Any diseased or normal structure of interest, e.g. thrombi, tumors or walls of myocardial vessels | |
| Peptides with sequence determined during generation process | Any of above targets - or may be unknown when make functional selection of vector binding to chosen diseased structure | Any diseased or normal structure of interest, e.g. thrombi, tumours or walls of myocardial vessels | |
| Oligonucleotides with sequence determined during generation process | Any of above targets - or may be unknown when make functional selection of vector binding to chosen diseased structure | Any diseased or normal structure of interest, e.g. thrombi, tumours or walls of myocardial vessels | |
| Modifications of oligos obtained as above | Any of above targets - or may be unknown when make functional selection of vector binding to chosen diseased structure | Any diseased or normal structure of interest, e.g. thrombi, tumours or walls of myocardial vessels | |
| Other chemicals with structure determined during generation process | Any of above targets - or may be unknown when make functional selection of vector binding to chosen diseased structure | Any diseased or normal structure of interest, e.g. thrombi, tumours or walls of myocardial vessels | |

Carbohydrate vectors

| Vector type | Receptor | Comments/areas of use | Ref |
|---|---|---|---|
| neo-glycoproteins | macrophages | general activation/inflammation | |
| oligosaccharides with terminal galactose | Asialo-glycoprotein receptor | liver | |
| Hyaluronan | aggrecan (a proteoglycan) "link proteins" cell-surface receptors: CD44 | | |
| Mannose | | Blood brain barrier, Brain tumours and other diseases causing changes in BBB | |
| Bacterial glycopeptides | | Blood brain barrier, Brain tumours and other diseases causing changes in BBB | |

Lipid vectors

| Vector type | Receptor | Comments/areas of use | Ref |
|---|---|---|---|
| LDL-like lipids | LDL-receptor | Atherosclerosis | |

Small molecule vectors

| Vector type | Receptor | Comments/areas of use | Ref |
|---|---|---|---|
| Adrenalin | Corresponding receptors | | |
| Betablockers | Adrenergic beta-receptors | Myocardium for beta-1 blockers | |
| Alpha-blockers | Adrenergic alpha-receptors | Vessel wall | |
| benzodiazepines serotonin-analogues | Serotonin-receptors | | |
| anti-histamines | Histamine-receptors | Vessel wall | |
| Acetyl-choline receptor antagonists | ACh-receptors | | |
| verapamil | $Ca^{2+}$-channel blocker | Heart muscle | |
| nifedipin | $Ca^{2+}$-channel blocker | Heart muscle | |
| Amiloride | $Na^+/H^+$-exchanger | Blocks this exchanges in kidney and is generally upregulated in cells stimulated by growth factors. | |

-continued

Small molecule vectors

| Vector type | Receptor | Comments/areas of use | Ref |
|---|---|---|---|
| Digitalis glycosides | $Na^+/K^+$-ATP-ases | myocardium peripheral vasculature, central nervous system | |
| Thromboxae/ Prostaglandin receptor antagonists or agonists | Thromboxane/ prostaglandin receptors | Vessel wall, Endothelium | |
| Glutathione | Glutathione-receptors Leukotriene-receptors | Lung, Brain | |
| Biotin | biotin transport protein on cell surface | | |
| Folate | folate transport protein on cell surface | Tumours | |
| Riboflavin | riboflavin transport protein on cell surface | | |
| Methotrexate | folate transport protein on cell surface | | |
| chlorambucil | general transport mechanisms | | |

References to the preceding tables

A. Auerbach, W., and R. Auerbach. 1994. "Angiogenesis inhibition: a review". *Pharmac. Ther.* 63: 265–311.

B. Barinaga, M. 1997. "Designing Therapies That Target Tumor Blood Vessels". *Science* 275 (Jan. 24): 482–484.

C. Folkman, J., P. B. Weisz, M. M. Joullie, W. W. Li, and W. R. Ewing. 1989. "Control of Angiogenesis With Synthetic Heparin Substitutes". *Science* 243: 1490–1493.

D. Fox, S. B., and A. L. Harris. 1997. "Markers of tumor angiogenesis: Clinical applications in prognosis and anti-angiogenic therapy". *Investigational New Drugs* 15 (1): 15–28.

E. Gastl, G., T. Hermann, M. Steurer, J. Zmija, E. Gunsilius, C. Unger, and A. Kraft. May 1997. "Angiogenesis as a target for tumor treatment". *Oncology* 54 (3): 177–184.

F. Griffloen, A. W., M. J. H. Coenen, C. A. Damen, S. M. M. Hellwig, D. H. J. Vanweering, W. Vooys, G. H. Blijham, and G. Groenewegen. 1 August 1997. "CD44 is involved in tumor angiogenesis; an activation antigen on human endothelial cells". *Blood* 90 (3): 1150–1159.

G. Hlatky, L., P. Hahnfeldt, and C. N. Coleman. 1996. "Vacular endothelial growth factor: environmental controls and effects in angiogenesis". *Brit. J. Cancer* 74 (Suppl. XXVII): S151–S156.

H. Maragoudakis, M. E., E. Pipili-Synethos, E. Sakkoula, D. Panagiotopoulos, N. Craniti, and J. M. Matsoukas. 1996. "Inhibition of TRAP-induced angiogenesis by the tripeptide Phe-Pro- Arg, a thrombin-receptor-derived peptide analogue". *Letters in Peptide Science* 3: 227–232.

I. Nguyen, M. 1997. "Angiogenic factors as tumor markers". *Investigational New Drugs* 15 (1): 29–37.

J. Ono, M., H. Izumi, S. Yoshida, D. Gtot, S. Jimi, N. Kawahara, T. Shono, S. Ushiro, M. Rynto, K. Kohno, Y. Sato, and M. Kuwano. 1996. "Angiogenesis as a new target for cancer treatment". *Cancer Chemoter. Pharmacol.* 38 (Suppl.): S78–S82.

K. Passe, T. J., D. A. Bluemke, and S. S. Siegelman. June 1997. "Tumor angiogenesis: Tutorial on implications for imaging". *Radiology* 203 (3): 593–600.

L. Saclarides, T. J. February 1997. "Angiogenesis in colorectal cancer". *Surgical Clinics of North America* 77 (1): 253.

M. Sage, E. H. May 1997. "Pieces of eight: Bioactive fragments of extracellular proteins as regulators of angiogenesis". *Trends in Cell Biology* 7 (5): 182–186.

N. Sagi-Assif, O., A. Traister, B. Z. Katz, R. Anavi, M. Eskenazy, and I. P. Witz. 1996. "TNF$\alpha$ and anti-Fas antibodies regulate Ly-6E.1 expression by tumor cells: A possible link between angiogenesis and Ly-6E.1". *Immunology Letters* 54: 207–213.

O. Strawn, L. M., G. McMahon, H. App, R. Schreck, W. R. Kuchler, M. P. Longhi, T. H. Hui, C. Tang, A. Levitzki, A. Gazit, I. Chen, G. Keri, L. Orfi, W. Risau, I. Flamme, A. Ullirch, K. P. Hirth, and L. K. Shawyer. 1996. "Flk-1 as a Target for Tumor Growth Inhibition". *Cancer Res.* 56: 3340–3545.

P. Stromblad, S., and D. A. Cheresh. December 1996. "Cell adhesion and angiogenesis". *Trends in Cell Biology* 6 (12): 462–468.

Q. Stromblad, S., and D. A. Cheresh. November 1996. "Integrins, angiogenesis and vascular cell survival". *Chemistry & Biology* 3 (11): 881–885.

R. Volpert, O., D. Jackson, N. Bouck, and D. I. H. Linzer. September 1996. "The insulin-like growth factor II/mannose 6-phosphate receptor is required for proliferin-induced angiogenesis". *Endocrinology* 137 (9): 3871–3876.

S. Yoshida, O. M., T. Shono, H. Izumi, T. Ishibashi, H. Suzuki, and M. Kuwano. 1997. "Involvement of Interleukin-8, Vascular Endothelial Growth Factor, and Basic Fibroblast Growth Factor in Tumor Necrosis Factor Alpha-Dependent Angiogenesis". *Mol. Cell. Biol.* 17: 4015–4023.

T. Zimrin, A. B., M. S. Pepper, G. A. McMahon, F. Nguyen, R. Montesano, and T. Maciag. 1996. "An Antisense Oligonucleotide to the Notch Ligand Jagged Enhances Fibroblast Growth Factor-induced Angiogenesis<in vitro>". *J. Biol. Chem.* 271 (Dec. 20): 32499–3502.

U. Albini, A., R. Soldi, D. Giunciuglio, E. Giraudo, R. Benelli, R. Primo, D. Noonan, M. Salio, G. Camussi, W. Rockl, and F. Bussolino. 1996. "The angiogenesis induced by HIV-1 Tat protein is mediated by the Flk-1/KDR receptor on vacular endothelial cells". *Nature Medicine* 2 (12 (Dec.)): 1371–1374.

V. Ferrara, N. 1996. "The biology of vascular endothelial growth factor". in *Molecular, Cellular and Clinical Aspects of Angiogenesis*, ed. M. E. Maragoudakis. New York: Plenum Press.

X. Jackson, R. L., S. J. busch, and A. J. Cardin. 1991. "Glycosaminoglycans: Molecular Properties, Protein Interactions, and Role in Physiological Processes". *Physiological Reviews* 71 (2): 481–435.

Y. Kinsella, M. G., C. K. Tsoi, H. T. Jarvelainen, and T. N. Wight. 1997. "Selective expression and processing of biglycan during migration of bovine aortic endothelial cells—The role of endogenous basic fibroblast growth factor". *Journal of Biological Chemnistry* 272: 318–325.

Z. Folkman, J. 1996. Tumor angiogenesis and tissue factor. *Nature Medicine* 2, 167–8

ZA. Relf, M., S. LeJeune, P.A. Scott, S. Fox, K. Smith, R. Leek, A. Moghaddam, R. Whitehouse, R. Bicknell and A:L. Harris. 1997. "Expression of the angiogenic factors vascular endothelial cell growth factor, acidic and basic fibroblast growth factor, tumor growth factor beta-1, platelet-derived endothelial cell growth factor, placenta growth factor and pleiotrophin in human primary breast cancer and its relation to angiogenesis". *Cancer Res.* 57, 963–9.

ZB. Carmeliet, P., L. Moons, M. Dewerchin, N. Mackman, T. Luther, G. Breier, V. Ploplis, M. Müller, A. Nagy, E. Plow, R. Gerard, T. Edgington, W. Risau, D. Collen. 1997. *Ann, N.Y. Acad. Sci.* 811, 191–206.

ZC. Van Hinsbergh, P. Koolwijk, R. Haanemaijer. 1997. "Role of fibrin and plasminogen activators in repair-associated angiogenesis: in vitro studies with human endothelial cells" EXS 79, 391–411.

Passe, T. J., D. A. Bluemke and S. S. Siegelman. 1997. *Radiology* 203: 593–600.

Representative examples of drugs useful in accordance with the invention include:

abamectin, abundiazole, acaprazine, acabrose, acebrochol, aceburic acid, acebutolol, acecainide, acecarbromal, aceclidine, aceclofenac, acedapsone, acediasulfone, acedoben, acefluranol, acefurtiamine, acefylline clofibrol, acefylline piperazine, aceglatone, aceglutamide, aceglutamide aluminium, acemetacin, acenocoumarol, aceperone, acepromazine, aceprometazine, acequinoline, acesulfame, acetaminophen, acetaminosalol, acetanilide, acetarsone, acetazolamide, acetergamine, acetiamine, acetiromate, acetohexamide, acetohydroxamic acid, acetomeroctol, acetophenazine, acetorphine, acetosulfone, acetriozate, acetryptine, acetylcholine chloride, acetylcolchinol, acetylcysteine, acetyldigitoxin, acetylleucine, acetylsalicyclic acid, acevaltrate, acexamic acid, acifran, acipimox, acitemate, acitretin, acivicin, aclantate, aclarubicin, aclatonium napadisilate, acodazole, aconiazide, aconitine, acoxatrine, acridorex, acrihellin, acrisorcin, acrivastine, acrocinide, acronine, actinoquinol, actodigin, acyclovir, adafenoxate, adamexine, ademetionine, adenosine phosphate, adibendan, adicillin, adimolol, adinazolam, adiphenine, aditeren, aditoprim, adrafinil, adrenalone, afloqualone, afurolol, aganodine, ajmaline, aklomide, alacepril, alafosfalin, alanine mustard, alanosine, alaproclate, alazanine triclofenate, albendazole, albendazole oxide, albuterol, albutoin, alclofenac, alcometasone dipropionate, alcloxa, alcuronium chloride, aldioxa, aldosterone, alepride, aletamine, alexidine, alfacalcidol, alfadex, alfadolone, alfaprostol, alfaxalone, alfentanil, alfuzosin, algestone acetonide, algestone acetophenide, alibendol, aliconazole, alifedrine, aliflurane, alimadol, alinidine, alipamide, alitame, alizapride, allantoin, alletorphine, allobarbital, alloclamide, allocupreide, allomethadione, allopurinol, allylestrenol, allyl isothicyanate, allyprodine, allylthiourea, almadrate sulfate, almasilate, almecillin, almestrone, alminoprofen, almitrine, almoxatone, alonacic, alonimid, aloxistatin, alozafone, alpertine, alphacetylmethadol, alphameprodine, alphamethadol, alphaprodine, alpha-vinylaziridinoethyl acetate, alpidem, alpiropride, alprazolam, alprenolol, alprostadil, alrestatin, altanserin, altapizone, alteconazole, althiazide, altrenogest, altretamine, aluminium acetate, aluminium clofibrate, aluminium subacetate, alverine, amadinone acetate, amafolone, amanozine, amantadine, amantanium bromide, amantocillin, ambasilide, ambazone, ambenonium chloride, ambenoxan, ambroxol, ambruticin, ambucaine, ambucetamide, ambuphylline, ambuside, ambutonium bromide, amcinafal, amcinafide, amcinonide, amdinocillin, amdinocillin pivoxil, amebucort, amedalin, ametantrone, amezepine, amezinium metilsulfate, amfenac, amfepentorex, amfetaminil, amflutizole, amfonelic acid, amicarbalide, amicibone, amicloral, amicycline, amidantel, amidapsone, amidephrine, amiflamine, amifloverine, amifloxacin, amifostine, amikacin, amikhelline, amiloride, aminacrine, amindocate, amineptine, aminobenzoic acid, aminocaproic acid, aminoethyl nitrate, aminoglutethimide, aminohippuric acid, aminometradine, aminopentamide, aminophylline, aminopromazine, aminopterin, aminopyrine, aminoquinol, aminoquinuride, aminorex, aminosalicyclic acid, aminothiadiazole, aminothiazole, amiodarone, amiperone, amipheazole, amipizone, amiprilose, amiquinsin, amisometradine, amisulpride, amiterol, amithiozone, amitraz, amitriptyline, amitriptylinoxide, amixetrine, amlexanox, amlodipine, amobarbital, amodiaquine, amogastrin, amolanone, amonofide, amoproxan, amopyroquin, amorolfine, amocanate, amosulalol, amotriphene, amoxapine, amoxecaine, amoxicillin, amoxydramine camsilate, amperozide, amphecloral, amphenidone, amphetamine, amphotalide, amphotericin B, ampicillin, ampiroxicam, amprolium, ampyrimine, ampyzine, amquinate, amrinone, amsacrine, amygdalin, amylene, amylmetacresol, amyl nitrite, anagestone acetate, anagrelide, anaxirone, anazocine, anazolene, ancarolol, ancitabine, androstanediol, androstanol propionate, androstenetrione, androstenonol propionate, anethole, anguidine, anidoxime, anilamate, anileridine, aniline, anilopam, anipamil, aniracetam, anirolac, anisacril, anisindione, anisopirol, anisoylbromacrylic acid, anitrazafen, anpirtoline, ansoxetine, antafenite, antazoline, antazonite, anthelmycin, anthiolimine, anthralin, anthramycin, antienite, antimony potassium tartrate, antimony thioglycollate, antipyrine, antrafenine, apalcillin, apazone, apicycline, apomorphine, apovincamine, apraclonidine, apramycin, aprindine, aprobarbital, aprofene, aptazapine, aptocaine, arabinosylmercaptopurine, aranotin, arbaprostil, arbekacin, arclofenin, arfendazam, arginine, arginine glutamat, arildone, arnolol, aronixil, arotinolol, arpinocid, arpromidine, arsanilic acid, arsthinol, artemisinin, articaine, asaley, ascorbic acid, ascorbyl palmitate, asocainol, aspartame, aspartic acid, asperlin, aspoxicillin, astemizole, atamestane, atenolol, atipamezole, atiprosin, atolide, atracurium besilate, atromepine, atropine, atropine oxide, auranofin, aurothoiglucose, aurothioglycanide, avilamycin-A, avridine, axamozide, azabon, azabuperone, azacitodine, azaclorzine, azaconazole, azacosterol, azacyclonol, azaftozine, azaguanidine, azaloxan, azamethonium bromide, azamulin, azanator, azanidazole, azaperone, azapicyl, azaprocin, azaquinzole, azaribine, azarole, azaserine, azaspirium chloride, azastene, azastrptonigrin, azatodine, azathioprine, azauridine, azelastine, azepexole, azepindole, azetepa, azidamfenicol, azidocillin, azimexon, azintamide, azipramine, azithromycin, azlocillin, azolimine, azosemide, azotomycin, aztreonam, azumolene, bacampicillin, baclofen, bacmecillinam, balsalazide, bamaluzole, bambuterol, bamethan, bamifylline, bamipine, bamnidazole, baquiloprim, barbexaclone, barbital, barucainide, batilol, bazinaprine, becanthone, beclamide, beclobrate, beclomethasone dipropionate, beclotiamine, befiperide, befunolol, befuraline, bekanamycin, belarizine, beloxamide, bemarinone, bemegride, bemetizide, bemitradine, benactyzine, benafentrine, benanserin, benapryzine, benaxibine, benazepril, bencianol, bencisteine, benclonidine, bencyclane, bendamustine, bendazac, bendazol, benderizine, bendroflumethiazide, benethamide penicillin, benexate, benflorex, benfosformin, benfotiamine, benfurodil hemisuccinate, benhepazone, benidipine, benmoxin, benolizime, benorilate, benorterone, benoxafos, benoxaprofen, benoxinate, benperidol, benproperine, benrixate, bensalan, benserazide, bensuldazic acid, bentazepam, bentemazole, bentiamine, bentipimine, bentiromide, benurestat, benzaldehyde, benzalkonium chloride, benzaprinoxide, benzarone, benzbromarone, benzestrol, benzethidine, benzethonium chloride, benzetimide, benzilonium bromide, benzindopyrine, benziodarone, benzmalecene, benznidazole, benzobarbital, benzocaine, benzoclidine, benzoctamide, benzodepa, benzododecinium chloride, benzoic acid, benzoin, benzonatate, benzopyrronium bromide, benzoquinium chloride, benzotript, benzoxiquine, benzoxonium chloride, benzoyl peroxide, benzoylpas, benzphetamine, benzpiperylon, benzpyrinium bromide, benzquercin, benzquinamide, benzthiazide, benztropine, benzydamine, benzylpenicillin, benzylsulfamide, beperidium iodide, bephenium naphtoate, bepiastine, bepridil, beraprost, berberine sulfate, bermastine, bermoprofen, berythromycin, besulpamide, beslunide, beta carotene, betacetylmethadol, betahistine, betaine, betameprodine, betamethadol, betamethasone, betamethasone acetate, betamethasone acibutate, betamethasone benzoate, betamethasone dipropionate, betamethasone phosphate, betamethasone valerate, betamicin, betaprodine, betaxolol, betazole, bethanechol chloride, bethanidine, betiatide, betoxycaine, bevantolol, bevonium metilsulfate, bezafibrate, bezitramide, bialamicol, bibenzonium bromide, bibrocathol, bicifadine, biclodil, biclofibrate, biclotymol, bicozamycin, bidimazium iodine, bietamiverine, bietaserpine, bifemelane, bifepramide, bifluranol, bifonazole, binedaline, binfloxacin, binfibrate, bioallethrin, bioresmethrin, biotin, bipenamol, biperiden, biphenamine, biriperone, bisacodyl, bisantrene, bis(aziridinyl) butanediol, bisbendazole, bisbentiamine, bisfenazone, bisfentidine, bismuth betanaphthol, bismuth-triglycollamate, bismuth subgallate, bismuth subsalicylate, bisorbin, bisoprolol, bisorcic, bioxatin acetate, bispyrithione magsulfex, bithionol, bithionoloxide, bitipazone, bitoterol, bitoscantate, bleomycin, bluensomycin, bofumustine, bolandiol dipropionate, bolasterone, bolazine, boldenone undecylenate, bolenol, bolmantalate, bometolol, bopindolol, bornaprine, bornaprolol, bornelone, botiacrine, boxidine, brallobarbital, brazergoline, brefonalol, bremazocine, brequinar, bretylium tosylate, brindoxime, brivundine, brobactam, broclepride, brocresine, brocrinat, brodimoprim, brofaromine, brofezil, brofoxine, brolaconazole, brolamfetamine, bromacrylide, bromadoline, bromamid, bromazepam, bromchlorenone, bromebric acid, bromerguride, brometenamine, bromfenac, bromhexine, bromindione, bromisovalum, bromociclen, bromocriptine, bromodiphenhydramine, bromofenofos, bromopride, bromoxandide, bromperidol, bromperidol decanoate, brompheniramine, bronopol, broparestrol, broperamole, bropirimine, broquinaldol, brosotamide, brosuximide, brotianide, brotizolam, brovanexine, brovincamine, broxaldine, broxaterol, broxitalamic acid, broxuridine, broxyquinoline, bruceantin, brucine, bucainide, bucetin, buciclovir, bucillamine, bucindolol, bucladesine, buclizine, buclosamide, bucloxic acid, bucolome, bucricaine, bucromarone, bucrylate, bucumolol, budesonide, budipine, budotitane, budralazine, bufenadrine, bufeniode, bufetolol, bufexamac, bufezolac, buflomedil, bufogenin, buformin, bufrolin, bufuralol, bumadizone, bumecaine, bumepidil, bumetanide, bumetrizole, bunaftine, bunamidine, bunamiodyl, bunaprolast, bunazosin, bunitrolol, bunolol, buparvaquone, bupicomide, bupivacaine, bupranolol, buprenorphine, bupropion, buquineran, buquinolate, buquiterine, buramate, burodiline, buspirone, busulfan, butabarbital, butacaine, butacetin, butaclamol, butadiazamide, butafosfan, butalamine, butalbital, butamben, butamirate, butamisole, butamoxane, butanediol cyclic sulfite, butanilicaine, butanixin, butanserin, butantrone, butaperazine, butaprost, butaverine, butedronate, buterizine, butetamate, butethamine, buthiazide, butibufen, butidrine, butikacin, butilfenin, butinazocine, butinoline, butirosin, butixirate, butobendine, butoconazole, butocrolol, butoctamide, butofilolol, butonate, butopamine, butopiprine, butoprozine, butopyrammonium iodide, butorphanol, butoxamine, butoxylate, butriptyline, butropium bromide, butylated hydroxyanisole, butylated hydroxytoluene, butylparaben, butynamine, buzepide metiodide, cabastine, cabergoline, cadralazine, cafaminol, cafedrine, caffeine, calcifediol, calcitrol, calcium citrate, calcium dobesilate, calcium glubionate, calcium gluceptate, calcium gluconate, calcium glycerophosphate, calcium hypophosphite, calcium lactate, calcium lactobionate, calcium levulinate, calcium mandelate, calcium pantothenate, calcium phosphate dibasic, calcium phophate tribasic, calcium saccharate, calcium stearate, calusterone, camazepam, cambendazole, camiverine, camostast, camphotamide, camptothecin, camylofin, canbisol, cannabinol, canrenoic acid, canrenone, cantharidine, capobenic acid, capreomycin, caproxamine, capsaicine, captamine, captodiame, captopril, capuride, caracemide, caramiphen, carazolol, carbachol, carbadox, carbaldrate, carbamazepine, carbamide peroxide, carbantel lauryl sulfate, carbaril, carbarsone, carbaspirin calcium, carbazeran, carbazochrome, carbazachrome salicylate, carbazachrome sulfonate, carbazocine, carbeniciltin, carbenicillin indanyl, carbencillin phenyl, carbenoxolone, carbenzide, carbestrol, carbetapentane, carbidopa, carbimazole, carbinoxamine, carbiphene, carbocloral, carbocysteine, carbofenotion, carbolfuschin, carbomycin, carboplatin, carboprost, carboprost methyl, carboquone, carbromal, carbubarb, carburazepam, carbutamide, carbuterol, carcainium chloride, carebastine, carfentanil, carfimate, carisoprodol, carmantadine, carmetizide, carmofur, carmustine, carnidazole, carnitine, carocainide, caroverine, caroxazone, carperidine, caperone, carphenazine, carpindolol, carpiramine, carprofen, carpronium chloride, carsalam, cartazolate, carteolol, carubicin, carumonam, carvedilol, carzenide, carzolamide, cathine, cathinone, cefaclor, cefadroxil, cefalonium, cefaloram, cefamandole, cefamandole naftate, cefaparole, cefatrizine, cefazaflur, cefazedone, cefazolin, cefbuperazone, cefcanel, cefcanel daloxate, cefedrolor, cefempidone, cefepime, cefetamet, cefetrizole, cefvitril, cefixime, cefmenoxime, cefmepidium chloride, cefmetazole, cefminox, cefodizime, cefonizid, cefoperazone, cefomanide, cefotaxime, cefotetan, cefotiam, cefoxazole, cefoxitin, cefpimizole, cefpiramide, cefpirome, cefpodoxime, cefpodoxime proxetil, cefquinome, cefrotil, cefroxadine, cefsulodin, cefsumide, ceftazidime, cefteram, ceftezole, ceftiofur, ceftiolene, ceftioxide, ceftizoxime, ceftriaxone, cefuracetime, cefuroxime, cefuraxime axetil, cefurzonam, celiprolol, cephacetrile, cephalexin, cephaloglycin, cephaloridine, cephalothin, cephapirin, cephradine, cetaben, cetamolol, cethexonium chloride, cetiedil, cetirizine, cetocycline, cetohexazine, cetophenicol, cetotiamine, cetoxime, cetraxate, chaulmosulfone, chendiol, chiniofon, chlophedianol, chloracyzine, chloral betaine, chloral hydrate, chloralose, chlorambucil, chloramine, chloramphenicol, chloramphenicol palmitate, chloramphenicol succinate, chlorazanil, chlorbenzoxamine, chlorbetamide, chlorcyclizine, chlordantoin, chlordiazepoxide, chlordimorine, chlorhexadol, chlorhexidine, chlorhexidine phosphanilate, chlorindanol, chlorisondamine chloride, chlormadinone acetate, chlormerodrin, chlormezanone, chlormidazole, chloronaphazine, chloroazodin, chlorobutanol, chlorocresol, chlorodihydroxyandrostenone, chloroethyl mesylate, 5-chloro-3'-fluoro-2'3-dideoxyuridine, chloroguanide, chlorophenothane, chloroprednisone acetate, chloroprocaine, chloropyramine, chloroquine, chloroserpidine, chlorothen, chlorothiazide, chlorotriansene, chloroxine, chloroxylenol, chlorozotocin, chlorphenesin, chlorphenesin carbamate, chlorpheniramine, chlorphenoctium amsonate, chlorphenoxamine, chlorphentermine, chlorproethazine, chlorproguanil, chlorpromazine, chlorpropamide, chlorprothixene, chlorquinaldol, chlortetracycline, chlorthalidone, chlorthenoxazine, chlorzoaxazone, chloecalciferol, cholic acid, choline chloride, choline glycerophosphate, chromocarb, chromonar, ciadox, ciamexon, cianergoline, cianidol, cianopramine, ciapilome, cicaprost, cicarperone, ciclactate, ciclafrine, ciclazindol, cicletanine, ciclomenol, ciclonicate, ciclonium bromide, ciclopirox, ciclopramine, cicloprofen, cicloprolol, ciclosidomine, ciclotizolam, ciclotropium bromide, ciclox ilic acid, cicloxolone, cicortonide, cicrotic acid, cidoxepin, cifenline, cifostodine, ciglitazone, ciheptolane, ciladopa, cilastatine, cilazapril, cilazaprilat, cilobamine, cilofungin, cilostamide, cilostazol, ciltoprazine, cimaterol, cimemoxin, cimepanol, cimetidine, cimetropium bromide, cimoxatone, cinchonine, cinchophen, cinecromen, cinepaxadil, cinepazet, cinepazic acid, cinepazide, cinfenine, cinfenoac, cinflumide, cingestol, cinitapride, cinmetacin, cinnamaverine, cinnamedrine, cinnarizine, cinnarizine clofibrate, cinnofuradione, cincotramide, cinodine, cinolazepam, cinooquidox, cinoaxin, cinoxate, cinoxolone, cinooxopazide, cinperene, cinprazole, cinpropazide, cinromide, cintazone, cintriamide, cinperone, ciprafamide, ciprafazone, ciprefadol, ciprocinonide, ciprofibrate, ciprofloxacin, cipropride, ciproquazone, ciprostene, ciramadol, cirazoline, cisapride, cisconazole, cismadinone, cisplatin, cistinexine, citalopram, citatepine, citenamide, citenazone, citicoline, citiolone, clamidoxic acid, clamoxyquin, clanfenur, clanobutin, clantifen, clarithromycin, clavulanic acid, clazolam, clazolimine, clazuril, clebopride, clefamide, clemastine, clemeprol, clemizole, clenbuterol, clenpirin, cletoquine, clibucaine, clidafidine, clidanac, clidinum bromide, climazolam, climbazole, climiqualine, clindamycin, clindamycin palmitate, clindamycin phosphate, clinofibrate, clinolamide, cliquinol, clioxanide, clipoxamine, cliprofen, clobazam, clobenoside, clobenzepam, clobenzorex, clobenztropine, clobetasol propionate, clobetasone butyrate, clobutinol, clobuzarit, clocanfamide, clocapramine, clociguanil, clocinizine, clocortolone acetate, clocortolone pivalate, clocoumarol, clodacaine, clodanolene, clodazon, clodoxopone, clodronic acid, clofazimine, clofenamic acid, clofenamide, clofenciclan, clofenetamine, clofenoxyde, clofenvinfos, clofeverine, clofexamide, clofezone, clofibrate, clofibric acid, clofibride, clofilium phosphate, cloflucarban, clofoctol, cloforex, clofurac, clogestone acetate, cloguanamil, clomacran, clomegestone acetate, clometacin, clometherone, clomethiazole, clometocillin, clomifenoxide, clominorex, clomiphene, clomipramine, clomocycline, clomoxir, clonazepam, clonazoline, clonidine, clonitazene, clonitrate, clonixeril, clonixin, clopamide, clopenthixol, cloperastine, cloperidone, clopidogrel, clopidol, clopimozide, clopipazan, clopirac, cloponone, cloprednol, cloprostenol, cloprothiazole, cloquinate, cloquinozine, cloracetadol, cloranolol, clorazepate, clorethate, clorexolone, clorgiline, cloricromen, cloridarol, clorindanic acid, clorindione, clormecaine, cloroperone, clorophene, cloroqualone, clorotepine, clorprenaline, clorsulon, clortermine, closantel, closiramine, clostebol, clothiapine, clothixamide, clotiazepam, cloticasone propionate, clotioxone, clotrimazole, clovoxamine, cloxacepride, cloxacillin, cloxacillin benzathine, cloxazolam, cloxestradiol, cloximate, cloxotestosterone, cloxypendyl, cloxyquin, clozapine, cobamide, cocaine, cocarboxylase, codeine, codoxime, cofisatin, cogazocine, colchicine, colestolone, colfenamate, colforsin, colterol, conessine, conorphone, copper gluconate, cormethasone acetate, corticosterone, cortisone acetate, cortisuzol, cortivazol, cortodoxone, cotarnine chloride, cotinine, cotriptyline, coumaphos, coumazoline, coumermycin, coumetarol, creatinolfosfate, crisnatol, croconazole, cromakalim, cromitrile, cromolyn, cropropamide, crospovidone, crotamiton, crotetamide, crotoniazide, crufomate, cuprimyxin, cuproxoline, cyacetacide, cyamemazine, cyanocobalamine, cyclacillin, cyclandelate, cyclarbamate, cyclazocine, cyclazodone, cyclexanone, cyclindole, cycliramine, cyclizine, cyclobarbital, cyclobendazole, cyclobenzaprine, cyclobutoic acid, cyclobutyrol, cyclofenil, cycloguanil, cloheximide, cycloleucine, cyclomenol, cyclomethicone, cyclomethycaine, cyclopentamine, cyclopenthiazide, cyclopentolate, cyclopenazine, cyclophosphamide, cyclopregnol, cyclopyrronium bromide, cycloserine, cyclosporine, cyclothiazide, cyclovalone, cycotiamine, cycrimine, cyheptamide, cyheptropine, cynarine, cypenamine, cypothrin, cyprazepam, cyprenophine, cyprodenate, cyproheptadine, cyprolidol, cyproquinate, cyproterone acetate, cyproximide, cystine, cytarabine, dacarbazine, dacemazine, dacisteine, dacinomycin, dacuronium bromide, dagapamil, dalbraminol, daledalin, daltroban, dametralast, damotepine, danazol, danitracen, danosteine, danthron, dantrolene, dapiprazole, dapsone, daptomycin, darenzepine, darodipine, datelliptium chloride, dunorubicin, dazadrol, dazepinil, dazidamine, dazmegrel, dazolicine, dazopride, dazoquinast, dacoxiben, deanol aceglumate, deanol acetaminobenzoate, deazauridine, deboxamet, debrisoquin, decamethonium bromide, decimemide, decitropine, declaben, declenperone, decloxizine, decominol, decoquinate, deditonium bromide, deferoxamine, deflazacort, defosfamide, dehydroacetic acid, dehydroemetine, dehydro-7-methyltestosterone, delanterone, delapril, delergotrile, delfantrine, delmadinone acetate, delmetacin, delmopinol, delorazepam, deloxone, delprostenate, dembrexine, demecarium bromide, demeclocycline, demecolcine, demecycline, demegestone, demelverine, demexiptiline, democonazole, demoxepam, denaverine, denbufylline, denipride, denopamine, denpidazone, denzimol, deoxyspergualin, depramine, deprodone, deprostil, deptropine, derpanicate, desacetylcolchicine tartrate, desaspidin, desiclovir, descinolone acetonide, deserpidine, desipramine, deslanoside, desmethylcolchicine, desmethylmisonidazole, desmethylmoramide, desocriptine, desogestrel, desomorphine, desonide, desoximetasone, desoxycorticosterone acetate, desoxycorticosterone pivalate, desoxypyridoxine, detajmium bitartrate, detanosal, deterenol, detomidine, detorubicin, detrothronine, devapamil, dexamethasone, dexamethasone acefurate, dexamethasone acetate, dexamethasone dipropionate, dexamethasone phosphate, dexamisole, dexbrompheniramine, dexchlorpheniramine, dexclamol, dexetimide, dexetozoline, dexfenfluramine, deximafen, dexindoprofen, dexivacaine, dexlofexidine, dexmedetomidine, dexoxadrol, dexpanthenol, dexpropranolol, dexproxibutene, dexecoverine, dextilidine, dextroamphetamine, dextrofemine, dextromethorphan, dextromoramide, dextrorphan, dextrothyroxine, dezaguanine, dezocine, diacerein, diacetamate, diacetolol, diacetylmorphine, diamfenetide, diaminomethylphenazinium chloride, diamocaine, diampromide, diamthazole, dianhydrogalactitol, diapamide, diarbarone, diathymosulfone, diatrizoic acid, diaveridine, diazepam, diaziquone, diazoacetylglycine hydrazide, diazouracil, diazoxide, dibekacin, dibemethine, dibenamine, dibenzepin, dibrompropamidine, dibromsalan, dibrospidium chloride, dibucaine, dibuprol, dibupyrone, dibusadol, dicarbine, dicarfen, dichlorallyl lawsone, dichlorisone acetate, dichlormezanone, dichlorofluormethane, dichloromethotrexate, dichlorophen, dichlorophenarsine, dichlorotetrafluoroethane, dichloroxylenol, dichlrphenamide, dichlorvos, diciferron, dicirenone, diclazuril, diclofenac, diclofensine, diclofurime, diclometide, diclonixin, dicloxacillin, dicobalt edetate, dicolinium iodide, dicresulene, dicumarol, dicyclomine, didemnin, dideoxycytidine, didrovaltrate, dieldrin, dienestrol, dienogest, diethadione, diethazine, diethylpropion, diethylstilbestrol, diethylstilbestrol diphosphate, diethylstilbestrol dipropionate, diethylthiambutene, diethyltoluamide, dietifen, difebarbamate, difemerine, difemetorex, difenamizole, difencloxazine, difenoximide, difenoxin, difetarsone, difeterol, diflorasone diacetate, difloxacin, difluanine, diflucortolone, diflurcortolone pivalate, diflumidone, diflunisal, difluprednate, diftalone, digalloyl trioleate, digitoxin, digoxin, dihexyverine, dihydralazine, dihydroazacytidine, dihydroergotamine, dihydrolenperone, dihydrostreptomycin, dihydrotachysterol, dihydroxyfluoroprogestrone, diisopromine, diisopropanolamine, dilazep, dilevalol, dilmefone, diloxanide, diltiazem, dimabefylline, dimecamine, dimecolonium iodide, dimecrotic acid, dimefadane, dimefline, dimelazine, dimemorfan, dimenhydrinate, dimenoxadol, dimeheptanol, dimepranol, dimepregnen, dimeprozan, dimercaprol, dimesna, dimesone, dimetacrine, dimetamfetamine, dimethadione, dimethaminostyrylquinoline, dimethazan, dimethindene, dimethiodal, dimethisoquin, dimethisterone, dimetholizine, dimethoxanate, dimethylhydroxytestosterone, dimethylnorandrostadienone, dimethylnortestosterone, dimethylstilbestrol, dimethyl, dimethylthiambutene, dimethyltubocurarinium chloride, dimetipirium bromide, dimetofrine, dimetridazole, diminazene, dimoxamine, dimoxaprost, dimoxyline, dimpylate, dinaline, dinazafone, diniprofylline, dinitolmide, dinoprost, dinoprostone, dinsed, diosmin, dioxadilol, dioxadrol, dioxamate, dioxaphetyl butyrate, dioxethedrin, dioxifedrine, dioxybenzone, dipenine bromide, diperodon, diphemanil methylsulfate, diphenadione, diphenan, diphenhydramine, diphendiol, diphenoxylate, diphenylpraline, diphoxazide, dipipanone, dipipoverine, dipiverin, diprafenone, diprenorphine, diprobutine, diprofene, diprogulic acid, diproleandomycin, diproqualone, diproteverine, diprotriozate, diproxadol, dipyridamole, dipyrithione, dipyrocetyl, dipyrone, dirithromycin, disobutamide, disofenin, disogluside, disopyramide, disoxaril, distigmine bromide, disulergine, disulfamide, disulfiram, disuprazole, ditazole, ditercalinium chloride, dithiazanine iodide, ditiocarb, ditiomustine, ditolamide, ditophal, divabuterol, dixanthogen, dizatrifone, dizocilpine, dobupride, dobutamine, docarpamine, doconazole, docusate, doliracetam, domazoline, domiodol, domiphen bromide, domipizone, domoprednate, domoxin, domperidone, don, donetidine, dopamantine, dopamine, dopexamine, dopropidil, doqualast, dorastine, doreptide, dosergoside, dotarizine, dotefonium bromide, dothiepin, doxacurium chloride, doxaminol, doxapram, doxaprost, doxazosin, doxefazepam, doxenitoin, doxepin, doxibetasol, doxifluridine, doxofylline, doxorubicin, doxpicomine, doxycycline, doxylamine, dramedilol, draquinolol, deazidox, dribendazole, drindene, drobuline, drocinonide, droclidinium bromide, drocode, drofenine, droloxifene, drometrizole, dromostanolone, dromostanolone propionate, dronabinol, dropempine, droperidol, droprenilamine, dropropizine, drotaverine, drotebanol, droxacin, droxicainide, droxicam, droxidopa, droxypropine, dulofibrate, dulozafone, duometacin, duoperone, dupracetam, durapatite, dyclonine, dydrogesterone, dymanthine, dyphylline, ebastine, ebrotidine, ebselen, ecastolol, echinomycin, echothiophate iodide, ecipramidil, eclanamine, eclazolast, econazole, ectylurea, edelfosine, edetic acid, edetol, edifolone, edogestrone, edoxudine, edrophonium chloride, efaroxan, efetozole, eflornithine, efloxate, efrotomycin, elantrine, elanzepine, elderfield's pyrimidine mustard, elfazepam, ellagic acid, elliptinium acetate, elmustine, elnadipine, eltenac, eltoprazine, elucaine, elziverine, embramine, embutramide, emepronium bromide, emetine, emiglitate, emilium tosylate, emopanil, emorfazone, emylcamate, enalapril, enalaprilat, enbucrilate, encainide, enciprazine, enclomiphene, encyprate, endomide, endralazine, endrysone, enefexine, enestebol, enfenamic acid, enflurane, eniclobrate, enilconazole, enilospirone, enisoprost, enocitabine, enolicam, enoxacin, enoxamast, enoximone, enoxolone, eniprazole, eniproline, enprazepine, enprofylline, enpromate, enprostil, enrofloxacin, entsufon sodium, enviomycin, enviradene, epalretat, epanolol, eperisone, ephedrine, epicainide, epicillin, epicriptine, epiestriol, epimestrol, epinastine, epinephrine, epinephryl borate, epipropidine, epirizole, epiroprim, epirubicin, epithiazide, epitiostanol, epoprostenol, epostane, eprazinone, eprovafen, eproxindine, eprozinol, epsiprantel, eptaloprost, eptazocine, equilin, erdosteine, ergocalciferol, ergoloid mesylates, ergonovine, ergosterol, ergotamine, ericolol, erizepine, erocainide, erythrityl tetranitrate, erythromycin, erythromycin acistrate, erythromycin ethylsuccinate, erythromycin propionate, erythrosine, esaprazole, esculamine, eseridine, esflurbiprofen, esmolol, esorubicin, esproquin, estazolam, estradiol, estradiol benzoate, estradiol cypionate, estradiol dipropionate, estradiol enanthate, estradiol undecylate, estradiol valerate, estramustine, estramustine phosphate, estrapronicate, estrazinol, estriol, estrofurate, estrone, estrone hydrogen sulfate, estropipate, esuprone, etabenzarone, etacepride, etafedrine, etafenone, etamestrol, etamiline, etamiphyllin, etamocycline, etanidazole, etanterol, etaqualone, etasuline, etazepine, etazolate, etebenecid, eterobarb, etersalate, ethacridine, ethacrynic acid, ethambutol, ethamivan, ethamsylate, ethanolamine oleate, ethaverine, ethchlorvynol, ethenzamide, ethazide, ethidium chloride, ethinamate, ethinyl estradiol, ethiofos, ethionamide, ethsterone, ethoheptazine, ethomoxane, ethonam, ethopropazine, ethosuximide, ethotoin, ethoxazene, ethoxazorutoside, ethoxzolamide, ethyybenztropine, ethyl biscoumacetate, ethyl carfluzepate, ethyl cartrizoate, ethyl dibunate, ethyl dirazepate, ethylenediamine, ethylestrenol, ethylhydrocupreine, ethyl loflazepate, ethylmethylthiambutene, ethylmorphine, 9-ethyl-6-mercaptopurine, ethyl nitrite, ethylnorepinephrine, ethylparaben, ethylphenacemide, ethylstibamine, ethynerone, ethynodiol diacetate, ethypicone, etibendazole, eticlopride, eticyclidine, etidocaine, etidronic acid, etifelmine, etifenin, etifoxine, etilamfetamine, etilefrine, etilefrine pivalate, etintidine, etiochlanolone, etipirium iodide, etiproston, etiracetam, etiroxate, etisazole, etisomicin, etisulergine, etizolam, etocarlide, etocrylene, etodolac, etodroxzine, etofamide, etofenamate, etofenprox, etofibrate, etoformin, etofuradine, etofylline, etoglucid, etolorex, etolotifen, etoloxamine, etomidate, etomidoline, etomoxir, etonitazene, etoperidone, etoposide, etoprindole, etoprine, etorphine, etosalamide, etoxadrol, etoxeridine, etozolin, etrabamine, etretinate, etryptamine, etymemazine, eucalyptol, eucatropine, eugenol, euprocin, evandamine, Evans blue, exalamide, exametazine, exaprolol, exepanol, exifone, exiproben, falintolol, falipamil, famiraprinium chloride, famotidine, famotine, famiprofazone, fanetizole, fantridone, fazadinium bromide, fazaribine, febantel, febarbamate, februpol, febuverine, feclemine, feclobuzone, fedrilate, felbamate, felbinac, felipyrine, felodipine, femoxetine, fenabutene, fenacetinol, fenaclon, fenadiazole, fenaptic acid, fenalamide, fenalcomine, fenamifuril, penamole, fenaperone, fenbendazole, fenbencillin, fenbufen, fenbutrazate, fencamfamine, fencibutirol, fenclexonium metilsulfate, fenclofenac, fenclonine, fenclorac, fenlozic acid, fendiline, fendosal, feneritrol, fenestrel, fenethazine, fenethylline, fenetradil, fenflumizole, fenfluramine, fenfluthrin, fengabine, fenharmane, fenimide, feniodium chloride, fenipentol, fenirofibrate, fenisorex, fenmetozole, fenmetramide, fenobam, fenocinol, fenoctimine, fenofibrate, fenoldopam, fenoprofen, fenoterol, fenoverine, fenoxazoline, fenoxedil, fenozolone, fenpentadiol, fenperate, fenipalone, fenipramide, feniprane, fenpiverinium bromide, fenprinast, fenproporex, fenprostalene, fenquizone, fenretinide, fenspiride, fentanyl, fentiazac, fenticlor, fenticonazole, fentonium bromide, fenyripol, fepentolic acid, fepitrizol, fepradinol, feprazone, fepromide, feprosidnine, ferriclate calcium, ferrotrenine, ferrous fumarate, ferrous gluconate, fetoxylate, fexicaine, fexinidazole, fezatione, fezolamine, fiacitabine, fibracillin, filenadol, filipin, fifexide, flamenol, flavamine, flavodic acid, flavodil, flavoneactic acid, flavoxate, flazalone, flecainide, flerobuterol, fleroxacin, flesinoxan, flestolol, fletazepam, floctafenine, flomoxef, flopropione, florantyrone, flordipine, floredil, florfenicol, florifenine, flosequinan, flotrenizine, floverine, floxacillin, floxacrine, floxuridine, fluacizine, flualamide, fluanisone, fluazacort, flubanilate, flubendazole, flubepride, flucabril, flucetorex, flucindole, fluciprazine, flucloronide, fluconazole, flucrylate, flucytosine, fludalanine, fludarabine phosphate, fludazonium chloride, fludiazepam, fludorex, fludoxopone, fludrocortisone acetate, flufenamic acid, flufenisal, flufosal, flufylline, fluindarol, fluindione, flumazenil, flumecinol, flumedroxone-17-acetate, flumequine, flumeridone, flumethasone, flumethasone pivalate, flumethiazide, flumetramide, flumexadol, flumezapine, fluminorex, flumizole, flumoxonide, flunamine, flunarizine, flunidazole, flunisolide, flunisolide acetate, flunitrazepan, flunixin, flunoprost, flunoxaprofen, fluocinolone acetonide, fluocinonide, flourcortin butyrate, fluocortolone, fluocortolone caproate, fluorescein, fluoresone, fluoroadenosine, 3-fluoroandrostanol, fluorodopane, fluorohydroxyandrosterone, fluorometholone, fluorometholone acetate, fluorosalan, 6-fluorotestosterone propionate, fluorouracil, 9-fluoroxotestenololactone, 9-fluoroxotestololacetone, fluotracen, fluoxetine, fluoxymesterone, fluparoxan, flupentixol, fluperamide, fluperlapine, fluperolone acetate, fluphenazine, fluphenazine enanthate, flupimazine, flupirtine, flupranone, fluprazine, fluprednidene, fluprednisolone, fluprednisolone valerate, fluprofen, fluprofylline, fluproquazone, fluprostenol, fluquazone, fluradoline, flurandrenoline, flurantel, flurazepam, flurbiprofen, fluretofen, flurithromycin, flurocitabine, flurofamide, flurogestone acetate, flurothyl, fluroxene, flusoxolol, fluspiperone, fluspirilene, flutamide, flutazolam, flutemazepam, flutiazin, fluticasone propionate, flutizenol, flutonidine, flutoprazepam, flutroline, flutropium bromide, fluvoxamine, fluzinamide, fluzoperine, folescutol, folic acid, fomidacillin, fominoben, fomocaine, fonazine, fopirtoline, forfenimex, formebolone, formetorex, formintrazole, formocortal, formoterol, fosarilate, fosazepam, foscarnet, foscolic acid, fosenazide, fosfocreatine, fosfomycin, fosfonet, fosfosal, fosinapril, fosmenic acid, fosmidomycin, forpirate, fostedil, fostriecin, fotemustine, fotreamine, frabuprofen, frentizole, fronepidil, froxiprost, ftaxilide, ftivazide, ftorafur, ftormetazine, ftorpropazine, fubrogonium iodide, fuchsin, fumagillin, fumoxcillin, fuprazole, furacrinic acid, furafylline, furalazine, furaltadone, furaprofen, furazabol, furazolidone, furazolium chloride, furbucillin, furcloprofen, furegrelate, furethidine, furfenorex, furidarone, furmethoxadone, furobufen, furodazole, furofenac, furomazine, furosemide, furostilbestrol, fursalan, fursultiamine, furterene, furtrethonium iodide, fusidic acid, fuzlocillin, gabapentin, gabexate, gaboxadol, galantamine, gallamine triethodide, gallopamil, galosemide, galtifenin, gampexine, gamolenic acid, ganciclovir, ganglefene, gapicomine, gapromidine, gefarnate, gemazocine, gemcadiol, gemeprost, gemfibrozil, gentamicin, gentian violet, gepefrine, gepirone, geroquinol, gestaclone, gestadienol, gestodene, gestonorone caproate, gestrinone, giparmen, gitaloxin, gitoformate, glafenine, glaziovine, gliamilide, glibornuride, glibutimine, glicaramide, glicetanile, geroquinol, gestaclone, gestadienol, gestodene, gestonorone caproate, gestrinone, giparmen, gitaloxin, gitoformate, glafenine, glaziovine, gliamilide, glibornuride, glibutimine, glicaramide, glicetanile, gliclazide, glicondamide, glidazamide, gliflumide, glimepiride, glipentide, glipizide, gliquidone, glisamuride, glisindamide, glisolamide, glisoxepide, gloxazone, gloximonam, glucametacin, glucosamine, glucosulfamide, glucosulfone, glucurolactone, glucuronamide, glunicate, glutamic acid, glutaral, glutarimide, glutaurine, glutethimide, glyburide, glybuthiazol, glybuzole, glyceryl monostearate, glycidyl methacrylate, glycine, glyclopyramide, glybiarsol, glycopyrrolate, glycyclamide, glyhexamide, glymidine, glyoctamide, glypinamide, glyprothiazol, glysobuzole, gold thiomalate, gold sodium thiosulfate, granisetron, griseofulvin, guabenxan, guacetisal, guafecainol, guaiactamine, guaiapate, guaietolin, guaifenesin, guaimesal, guaisteine, guaithylline, guamecycline, guanabenz, guanacline, guanadrel, guanazodine, guanazole, guanclofine, guancydine, guanethidine, guanfacine, guanisoquin, guanoclor, guanoctine, guanoxabenz, guanoxan, guanoxyfen, hadacidin, halazepam, halazone, halcinonide, halethazole, halocortolone, halofantrine, halofenate, halofuginone, halometasone, halonamine, halopemide, halopenium chloride, haloperidol, haloperidol decanoate, haloperidone acetate, haloprogesterone, haloprogin, halothane, haloxazolam, haloxon, halquinols, hedaquinium chloride, hepronicate, heptabarbital, heptaminol, heptaverine, heptolamide, hepzidine, hetacillin, hetaflur, heteronium bromide, hexachlorophene, hexacyclonate, hexacyprone, hexadiline, hexadimethrine bromide, hexafluorenium bromide, hexamethonium bromide, hexamidine, hexapradol, hexaprofen, hexapropymate, hexasonium iodide, hexacarbacholine bromide, hexedine, hexestrol, hexetidine, hexobarbital, hexobendine, hexocyclium methylsulfate, hexoprenaline, hexopyrronium bromide, hexylcaine, hexylene glycol, hexylresorcinol, histamine, histapyrrodine, homarylamine, homatropine, homatropine methylbromide, homidium bromide, homochlorcyclizine, homofenazine, homoharringtonine, homopipramol, homosalate, homotestosterone propionate, homprenorphine, hopantenic acid, hoquizil, hycanthone, hydracarbazine, hydralazine, hydrargaphen, hydrobentizide, hydrochlorthiazide, hydrocodone, hydrocortamate, hydrocortisone, hydrocortisone aceponate, hydrocortisone acetate, hydrocortisone butyrate, hydrocortisone cypionate, hydrocortisone-phosphate, hydrocortisone succinate, hydrocortisone valerate, hydroflumethiazide, hydromadinone, hydromorphinol, hydromorphone, hydroquinone, hydroxindasate, hydroxindasol, hydroxyoxocobalamin, hydroxy amphetamine, hydroxychloroquine, hydroxydimethandrostadienone, hydroxydione succinate, hydroxymethylandrostanone, 10-hydroxynorehisterone, hydroxypethidine, hydroxyphenamate, hydroxyprocaine, hydroxyprogeserone, hydroxyprogesterone caproate, hydroxypyridine tartrate, hydroxystilbamidine, 7-hydroxytestololacetone, hydroxytestosterone propionate, hydroxytetracaine, hydroxytoluic acid, hydroxyurea, hydroxyzine, hymecromone, hyoscyamine, hypericin, ibacitabine, ibafloxacin, ibazocine, ibopamine, ibrotamide, ibudilast, ibufenac, ibuprofen, ibuprofen piconol, ibuproxam, ibuterol, ibuverine, icazepam, icosipiramide, icotidine, idarubicin, idaverine, idazoxan, idebenone, idenast, idoxuridine, idralfidine, idrocilamide, idropranolol, ifenprodil, ifosfamide, ifoxetine, ilmofosine, iloprost, imafen, imanixil, imazodan, imcarbofos, imexon, imiclopazine, imidazole salicylate, imidazopyrazole, imidecyl iodine, imidocarb, imidoline, imidurea, imiloxan, iminophendimide, imipenem, imipramine, imipraminoxide, imirestat, imolamine, imoxiterol, impacarzine, impromidine, improsulfan, imuracetam, inaperisone, indacrinone, indalpine, indanazoline, indanidine, indanorex, indapamide, indatraline, indacainide, indeloxazine, indenolol, indicine-N-oxide, indigotindisulfonic acid, indobufen, indocate, indocyanine green, indolapril, indolidan, indomethacin, indopanolol, indopine, indoprofen, indoramin, indorenate, indoxole, indriline, inicarone, inocoterone, inosine, inosine dialdehyde, inositol niacinate, inproquone, intrazole, intriptyline, iobenzamic acid, iobutic acid, iocarmic acid, iocetamic acid, iodamide, iodecimol, iodetryl, iodipamide, iodixanol, iodoalphionic acid, iodol, iodophthalein, iodoquinol, iodothiouracil, iodoxamic acid, ioglicic acid, ioglucol, ioglucomide, ioglunide, ioglycamic acid, iogulamide, iohexol, iodlidonic acid, iolixanic acid, iomeglamic acid, iomeprol, iomorinic acid, iopamidol, iopanoic acid, iopentol, iophendylate, iophenoxic acid, iopromic acid, iopromide, iopronic acid, iopydol, iopydone, iosarcol, iosefamic acid, ioseric acid, iosimide, iosulamide, iosumetic acid, iotasul, iotetric acid, iothalamic acid, iotranic acid, iotrizoic acid, iotrolan, iotroxic acid, ioversol, ioxabrolic acid, ioxaglic acid, ioxitalamic acid, ioxotrizoic acid, iozomic acid, ipexidine, ipodic acid, ipragratine, ipramidil, ipratropium bromide, iprazochrome, ipriflavone, iprindole, iprocinodine, iproclozide, iprocrolol, iprofenin, iproheptine, iproniazid, iproidazole, iproplatin, iprotiazem, iproxamine, iprozilamine, ipsalazide, ipsapirone, iquindamine, irindalone, irloxacin, irolapride, irsogladine, isamfazone, isamoltan, isamoxole, isaxonine, isbogrel, isepamicin, isoaminile, isobromindione, isobucaine, isobutamben, isocarboxazid, isoconazole, isocromil, isoetharine, isofezolac, isoflupredone acetate, isoflurane, isoflurophate, isoleucine, isomazole, isomerol, isometamidium, isomethadone, isomethepthene, isomylamine, isoniazid, isonixin, isoprazone, isoprednidene, isoprofen, isoprofamide iodide, isopropicillin, isopropyl myristate, isopropyl palmitate, isoproterenol, isosorbide, isosorbide dinitrate, isosorbide mononitrate, isospalglumic acid, isosulfan blue, isosulpride, isothipendyl, isotic, isotiquimide, isotretinoin, isoxaprolol, isoxepac, isoxicam, isoxsuprine, isradipine, itanoxone, itazigrel, itraconazole, itrocainide, ivermectin bib, ivoqualine, josamycin, kainic acid, kalafungin, kanamycin, kebuzone, keracyanin, ketamine, ketanserin, ketazocine, ketazolam, kethoxal, ketipramine, ketobemidone, ketocaine, ketocainol, ketoconazole, ketoprofen, ketorfanol, ketorolac, ketotifen, ketotrexate, khellin, khelloside, kitasamycin, labetalol, lacidipine, lactalfate, lactose, lactulose, lamotrigine, lamtidine, lanatoside, lapachol, lapinone, lapyrium chloride, lasalocid, laudexium methyl sulfate, lauralkonium chloride, laureth, laurixamine, laurocapram, lauroguadine, laurolinium acetate, lauryl isoquinolinium, lefetamine, leflunomide, leiopyrrole, lemidosul, lenampicillin, leniquinsin, lenperone, leptacline, lergotrile, letimide, letosteine, leucine, leucinocaine, leucocianidol, leucovorin,levacecarnine, levallorphan, levamfetamine, levamisole, levdropropizine, levisoprenaline, levlofexidine, levobunolol, levocabastine, levocarnitine, levodopa, levofacetoperane, levofenfluramine, levofuraltadone, levoglutamide, levomenol, levomethadone, levomethadyl acetate, levomethorphan, levometiomeprazine, levomopranol, levomoramide, levonantradol, levonordeprin, levonorgestrel, levophenacyl morphan, levopropoxyphene, levopropylcillin, levopropylhexedrine, levoprotiline, levorin, levorphanol, levothyroxine, levoxadrol, lexofenac, libecillide, libenzapril, lidamidine, lidocaine, lidofenin, lidoflazine, lifibrate, lilopristone, limaprost, lincomycin, lindane, linsidomine, liothyronine, liroldine, lisinopril, lisuride, lithium carbonate, lithium citrate, litracen, lividomycin, lixazinone, lobeline, lobendazole, lobenzarit, lobuprofen, locicortone, lodaxaprine, lodacezarlodinixil, lodiperone, lodoxamide, lodoxamide ethyl, lofemizole, lofendazam, lofentanil, lofepramine, lofexidine, loflucarban, lombazole, lomefloxacin, lometraline, lomevactone, lomifylline, lomofungin, lomustine, lonapalene,lonaprofen, lonazolac, lonidamine, loperamide, loperamide oxide, lopirazepam, loprazolam, loprodiol, lorajmine, lorapride, loratadine, lorazepam, lorbamate, lorcainide, lorcinadol, lorglumide, lormetazepam, lortalamine, lorzafone, losindole, losulazine, lotifazole, lotrifen, lotucaine, lovastatin, loxanast, loxapine, loxiglumide, loxoprofen, loxtidine, lozilurea, lucanthone, lucartamide, lucimycin, lufuradom, lupitidine, luprostiol, luxabendazole, lyapolate sodium, lycetamine, lydimycin, lymecycline, lynestrenol, lysergide, lysine, mabuterol, maduramicin, mafenide, mafoprazine, mafosfamide, magnesium citrate, magnesium gluconate, magnesium salicylate, malathion, malethamer, malic acid, malotilate, manidipine, manganese gluconate, mannitol, mannitol hexanitrate, mannomustine, mannosulfan, manozodil, maprotiline, maridomycin, mariptiline, maroxepin, maytansine, mazaticol, mazindol, mazipredone, mebanazine, mebendazole, mebenoside, mebeverine, mebezonium iodide, mebhydrolin, mebiquine, mebolazine, mebrofenin, mebutamate, mebutizide, mecamylamine, mecarbinate, mecetronium ethylsulfate, mechlorethamine, meciadanol, mecinarone, meclizine, meclocycline, meclocycline sulfosalicylate, meclofenamic acid, meclofenoxate, meclonazepam, mecloqualone, mecloralurea, meclorisone dibutyrate, mecloxamine, mecobalamin, mecrylate, mecysteine, medazepam, medazomide, medetomidine, medibazine, medifoxamine, medorinone, medorubicin, medrogestone, medronic acid, medroxalol, medroxyprogestrone, medroxyprogestrone acetate, medrylamine, medrysone, mefeclorazine, mefenamic acid, mefenidil, mefenidramium metilsulfate, mefenorex, mefeserpine, mefexamide, mefloquine, mefruside, megalomicin, megestrol acetate, meglitinide, megucycline, meglumine, meglutol, meladrazine, melarsonyl, melarsoprol, melengestrol acetate, meletimide, melinamide, melitracen, melizame, meloxicam, melperone, melphalan, memantine, memotine, menabitan, menadiol, menadiol diphosphate, menadiol disulfate, menadione, menadione sodium bisulfite, menatetrenone, menbutone, menfegol, menglytate, menitrazepam, menoctone, menogaril, menthol, meobentine, meparfynol, mepazine, mepenzolate bromide, meperidine, mephenesin, mephenoxalone, mephentermine, mephenyton, mephobarbital, mepindolol, mepiprazole, mepiroxol, mepitiostane, mepivacaine, mepixanox, mepramidil, meprednisone, meprobamate, meproscillarin, meproxitol, meprylcaine, meptazinol, mequidox, mequinol, mequitazine, meralein, meralluride, merbarone, merbromin, mercaptamine, mercaptomerin, mercaptopurine, mercuderamide, mercufenol chloride, mercumatilin, mercurobutol, mergocriptine, merophan, mersalyl, mesabolone, mesalamine, meseclazone, mesna, mesocarb,mesohexestrol, mesoridazine, mesipirenone,mestanolone, mesterolone, mestranol,mesudipine, mesulergine, mesulfamide, mesulfen, mesuprine, metabromsalan, metacetamol, metaclazepam, metaglycodol, metahexamide, metamelfalan, metamfazone, metamfepramone, metampicillin, metanixin, metapramine, metaproterenol, metaraminol, metaterol, metaxalone, metazamide, metazide, metazocine, metbufen, meteneprost, metergoline, metergotamine, metescufylline, metesculetol, metethoheptazine, metformin, methacholine chloride, methacycline, methadone, methadyl acetate, methallenestril, methallibure, methalthiazide, methamphetamine, methandriol, methandrostenolone, methaniazide, methantheline bromide, methaphenilene, methapyrilene, methaqualone, metharbital, methastyridone, methazolamide, methdilazine, methenamine, methenolone acetate, methenolone enanthate, metheptazine, methestrol, methetoin, methicillin, methimazole, methiodal sodium, methioguanine, methiomeprazine, methionine, methisazone, methitural, methixene, methocarbamol, methohexital, methopholine, methoserpidine, methotrexate, methotrimeprazine, methoxamine, methoxsalen, methoxyflurane, methoxyphedrine, methoxyphenamine, methoxypromazine, methscopolamine bromide, methsuximide, methylclothiazide, N-methyladrealone hcl, methyl alcohol, methylatropine nitrate, methylbenactyzium bromide, methylbenzethonium, methylchromone, methyldesorphine, methyldihydromorphine, methyldopa, methyldopate, methylene blue, methylphedrine, methylergonovine, methylformamide, methyl nicotinate, 2-methyl-19-nortestosterone, 2-methyl-11-oxoprogestrone, methyl palmoxirate, methylparaben, methylphendiate, methylprednisolone, methylprednisolone aceponate, methylprednisolone acetate, methylprednisolone hemisuccinate, methylprednisolone phosphate, methylprednisolone suleptanate, methyl salicylate, methylprednisolne s amethyl testosterone, 7-methyltestosterone, 17-methyltestosterone, 7-methyltesosterone propionate, methylthionosine, 16-methylthioprogestone, methylthiouracil, methynodiol diacetate, methyprylon, methysergide, metiamide, metiapine, metiazinic acid, metibride, meticrane, metildigoxin, metindizate, metioprim, metioxate, metipirox, metipranolol, metiprenaline, metitepine, metizoline, metkephamid, metochalcone, metocinium iodide, metoclopramide, metocurine iodide, metofenazate, metogest, metolazone, metomidate, metopimazine, metopon, metoprine, metoprolol, metoquizine, metoserpate, metostilenol, metoxepin, metrafazoline, metralindole, metrazifone, metrenperone, metribolone, metrifonate, metrifudil, metrizamide, metrizoic acid, metronidazole, meturedepa, metyrapone, metyridine, metyrosine, mevastatin, mexafylline, mexazolam, mexenone, mexiletine, mexiprostil, mexoprofen, mexrenoate, mezacopride, mezepine, mezilamine, mezlocillin, mianserin, mibolerone, micinicate, miconazole, micronomicin, midaflur, midaglizole, midalcipran, midamaline, midazogrel, midazolam, midecamycin, midodrine, mifentidine, mifepristone, mifobate, miglitol, mikamycin, milacemide, milenperone, milipertine, miloxacin, milrinone, milverine, mimbane, minaprine, minaxolone, mindolilol, mindoperone, minepentate, minocromil, minocycline, minoxidil, mioflazine, mipimazole, mirincamycin, miristalkonium chloride, miroprofen, mirosamicin, misonidazole, misoprostol, mitindomide, mitobronitol, mitoclomine, mitoguazone, mitolactol, mitomycin, mitonafide, mitopodozide, mitoquidone, mitotane, mitotenamine, mitoxantrone, mitozolomide, mivacurium chloride, mixidine, misoprostol, mitindomide, mitobronitol, mitoclomine, mitoguazone, mitolactol, mitomycin, mitonafide, mitopodozide, mitoquidone, mitotane, mitotenamine, mitoxantrone, mitozolomide, mivacurium chloride, mixidine, mizoribine, mobecarb, mobenzoxamine, mocimycin, mociprazine, moclobemide, moctamide, modafinil, modaline, mofebutazone, mofloverine, mofoxime, molfarnate, molinazone, molindone, molracetam, molsidomine, mometasone furoate, monalazone disodium, monensin, monobenzone, monoethanolamine, monometacrine, monophosphothiamine, monothioglycerol, monoxerutin, montirelin, moperone, mopidamol, mopidralazine, moprolol, moquizone, morantel, morazone, morclofone, morforex, moricizine, morinamide, morniflumate, morocromen, moroxydine, morpheridine, morphine, morsuximide, motapizone, motrazepam, motretinide, moveltipril, moxadolen, moxalactam, moxaprindine, moxastine, moxaverine, moxazocine, moxestrol, moxicoumone, moxipraquine, moxisylyte, moxnidazole, moxonidine, mupirocin, murabutide, murocainide, muzolimine, mycophenolic acid, myfadol, myralact, myrophine, myrtecaine, nabazenil, nabilone, nabitan, naboctate, nabumetone, nadide, nadolol, nadoxolol, naepaine, nafamostat, nafazatrom, nafcaproic acid, nafcillin, nafenodone, nafenopin, nafetolol, nafimidone, nafiverine, naflocort, nafomine, nafoxadol, nafoxidine, nafronyl, naftalofos, naftazone, naftifine, naftopidil, naftoxate, naftypramide, nalbuphine, nalidixic acid, nalmefene, nalmexone, nalorphine, naltrexone, naminterol, namoxyrate, nanaprocin, nandrolone cyclotate, nandrolone decanoate, nandrolone phenpropionate, nanofin, nantradol, napactadine, napamezole, naphazoline, naphthonone, naprodoxime, naproxen, naproxol, naranol, narasin, natamycin, naxagolide, naxaprostene, nealbarbital, nebidrazine, nebivolol, nebracetam, nedocromil, nefazodone, neflumozide, nefopam, nelezaprine, neoarsphenamine, neocinchophen, neomycin, neostigmine bromide, nequinate, neraminol, nerbacadol, nesapidil, nesosteine, netilmicin, netobimin, neutramycin, nexeridine, niacin, niacinamide, nialamide, niaprazine, nibroxane, nicafenine, nicainoprol, nicametate, nicarbazin, nicarpidine, nicergoline, niceritrol, niceverine, niclofolan, niclosamide, nicoboxil, nicoclonate, nicocodine, nicocortonide, nicodicodine, nicofibrate, nicofuranose, nicofurate, nicogrelate, nicomol, nicomorphine, nicopholine, nicorandil, nicothiazone, nicotinyl alcohol, nicoxamat, nictiazem, nictindole, nodroxyzone, nifedipine, nifenalol, nifenazone, niflumic acid, nifluridide, nifuradene, nifuraldezone, nifuralide, nifuratel, nifuratrone, nifurdazil, nifurethazone, nifurfoline, nifurimide, nifurizone, nifurmazole, nifurmerone, nifuroquine, nifuroxazide, nifuroxime, nifurpipone, nifurpirinol, nifurprazine, nifurquinazole, nifursemizone, nifursol, nifurthiazole, nifurtimox, nifurtoinol, nifurvidine, nifurzide, niguldipine, nihydrazone, nikethamide, nileprost, nilprazole, niludipine, nilutamide, nilvadipine, nimazone, nimesulide, nimetazepam, nimidane, nimodipine, nimorazole, nimustine, niometacin, niperotidine, nipradilol, niprofazone, niridazole, nisbuterol, nisobamate, nisoldipine, nisoxetine, nisterime acetate, nitarsone, nitazoxanide, nithiamide, nitracrine, nitrafudam, nitralamine, nitramisole, nitraquazone, nitrazepam, nitrefazole, nitrendipine, nitricholine, nitrochlofene, nitrocycline, nitrodan, nitrofurantoin, nitrofurazone, nitroglycerin, nitromersol, nitromide, nitromifene, nitroscanate, nitrosulfathiazole, nitroxinil, nitroxoline, nivazol, nivimeldone, nixylic acid, nizatidine, nizofenone, noberastine, nocloprost, nocodazole, nofecainide, nogalamycin, nolinium bromide, nomegestrol, nomelidine, nomifensine, nonabine, nonaperone, nonapyrimine, nonoxynol-4, nonoxynol-9, noracymethadol, norbolethone, norbudrine, norclostebol, norcodeine, nordazepam, nordefrin, nordinone, norepinephrine, norethandrolone, norethindrone, norethindrone acetate, norethynodrel, noreximide, norfenefrine, norfloxacin, norfloxacin succinil, norflurane, norgesterone, norgestimate, norgestomet, norgestrel, norgestrienone, norletimol, norlevorphanol, normethadone, normethandrone, normorphine, norpipanone, nortestosterone propionate, nortetrazepam, nortriptyline, norvinisterone, nosantine, noscapine, nosiheptide, novobiocin, noxiptiline, noxytiolin, nuclomedone, nuclotixine, nufenoxole, nuvenzepine, nylestriol, nylidrin, nystatin, obidoxime, ociltide, ocrylate, octabenzone, octacaine, octafonium chloride, octamoxin, octamylamine, octanoic acid, octapinol, octastine, octaverine, octazamide, octenidine, octenidine saccharin, octicizer, octimibate, octorylene, octodrine, octopamine, octotiamine, octoxynol-9, octriptyline, octrizole, ofloxacin, ofornine, oftasceine, olaflur, olaquindox, oleanomycin, oletimol, oleyl alcohol, olivomycin a, olmidine, olpimedone, olsalazine, oltipraz, olvanil, omeprazole, omidoline, omoconazole, omonasteine, onapristone, ondansetron, ontianil, opiniazide, opipramol, orazamide, orbutopril, orconazole, orestrate, ormetoprim, ornidazole, ornipressin, ornithine, ornoprostil, orotic acid, orotirelin, orpanoxin, orphenadrine, ortetamine, osalmid, osmadizone, otilonium bromide, otimerate sodium, ouabain, oxabolone cipionate, oxabrexine, oxaceprol, oxacillin, oxadimedine, oxaflozane, oxaflumazine, oxagrelate, oxalinast, oxaliplatin, oxamarin, oxametacin, oxamisole, oxamniquine, oxanamide, oxandrolone, oxantel, oxapadol, oxapium iodide, oxapropanium iodide, oxaprotiline, oxaprozin, oxarbazole, oxatomide, oxazafone, oxazepam, oxazidione, oxazolam, oxazorone, oxcarbazepine, oxdralazine, oxeladin, oxendolone, oxepinac, oxetacillin, oxethazaine, oxetorone, oxfendazole, oxfenicine, oxibendazole, oxibetaine, oxiconazole, oxidopamine, oxidronic acid, oxifentorex, oxifungin, oxilorphan, oximonam, oxindanac, oxiniacic acid, oxiperomide, oxiracetam, oxiramide, oxisopred, oxisuran, oxitefonium bromide, oxitriptan, oxitriptyline, oxitropium bromide, oxmetidine, oxodipine, oxogestone phenpropionate, oxolamine, oxolinic acid, oxomemazine, oxonazine, oxophenarsine, oxoprostol, oxpheneridine, oxprenoate potassium, oxprenolol, oxtriphylline, oxybenzone, oxybutynin, oxychlorosene, oxycinchophen, oxyclozanide, oxycodone, oxydipentonium chloride, oxyfedrine, oxymesterone, oxymetazoline, oxymetholone, oxymorphone, oxypendyl, oxypertine, oxyphenbutazone, oxyphenonium bromide, oxypurinol, oxypyrronium bromide, oxyquinoline, oxyridazine, oxysonium iodide, oxytetracycline, oxytiocin, ozagrel, ozolinone, pacrinolol, pactamycin, padimate, pafenolol, palatrigine, paldimycin, palmidrol, palmoxiric acid, pamabrom, pamaquine, pamatolol, pamidronic acid, pancuronium bromide, panidazole, panomifene, patenicate, panthenol, pantothenic acid, panuramine, papaverine, papaveroline, parachlorophenol, paraflutizide, paraldehyde, paramethadione, paramethasone acetate, paranyline, parapenzolate bromide, parapropamol, pararosaniline, pararosaniline embonate, paraxazone, parbendazole, parconazole, pareptide, parethoxycaine, pargeverine, pargolol, pargyline, paridocaine, parodilol, paromomycin, paroxetine, paroxypropione, parsalmide, partricin, parvaquone, pasiniazid, paulomycin, paxamate, pazelliptine, pazoxide, pcnu, pecilocin, pecocycline, pefloxacin, pelanserin, pelretin, pelrinone, pemedolac, pemerid, pemoline, pempidine, penamecillin, penbutolol, pendecamaine, penfluridol, penflutizide, pengitoxin, penicillamine, penicillin procaine, penicillin, penimepicycline, penimocycline, penirolol, penmesterol, penoctonium bromide, penprostene, pentabamate, pentacynium chloride, pentaerythritol tetranitrate, pentafluranol, pentagastrin, pentagestrone, pentalamide, pentamethonium bromide, pentamethylmelamine, pentamidine, pentamoxane, pentamustine, pentapiperide, pentapiperium methylsulfate, pentaquine, pentazocine, pentetate calcium trisodium, pentetic acid, penthienate bromide, penthrichloral, pentiapine maleate, pentifylline, pentigetide, pentisomicin, pentisomide, pentizidone, pentobarbital, pentolinium tartrate, pentomone, pentopril, pentorex, pentosan polysulfate sodium, pentostatin, pentoxifylline, pentrinitrol, pentylenetrazole, peplomycin, pepstatin, peraclopone, peradoxime, perafensine, peralopride, peraquinsin, perastine, peratizole, perbufylline, perfluamine, perflunafene, pergolide, perhexilene, periciazine, perimetazine, perindopril,perindoprilat,perisoxal, perlapine, permethrin, perphenazine, persilic acid, petrichloral, pexantel, phanquone, phenacaine, phenacemide, phenacetin, phenacttropinium chloride, phenadoxone, phenaglycodol, phenamazoline, phenampromide, phenarsone sulfoxylate, phenazocine, phenazopyridine, phencarbamide, phencyclidine, phendimetrazine, phenelzine, pheneridine, phenesterin, penethicillin, phenformin, phenglutarimide, phenicarbazide, phenindamine, phenindione, pheniprazine, pheniramine, phenisonone, phenmetrazine, phenobarbital, phenobutiodil, phenolphtalein, phenolsulfonphthalein, phenomorphan, phenoperidine, phenothiazine, phenothrin, phenoxybenzamine, phenoxypropazine, phenprobamate, phenprocoumon, phenpromethamine, phensuximide, phentermine, phentolamine, phenylalanine, phenyl aminosalicylate, phenylbutazone, phenylrphrine, phenylethyl alcohol, phenylmercuric acetate, phenylmercuric borate, phenylmercuric chloride, phenylmercuric nitrate, phenylmethylbarbituric acid, phenylpropanolamine, phenylthilone, phenyltoloxamine, phenyramidol, phenytoin, phetharbital, pholcodine, pholedrine, phosphoramide mustard, phoxim, phthalofyne, phthalysulfacetamide, phthalylsulfamethizole, phthalylsulfathiazole, physostigmine, phytic acid, phytonadiol diphosphate, phytonadione, pibecarb, pibenzimol, pibecarb, pibenzimol, piberaline, picafibrate, picartamide, picenadol, picilorex, piclonidine, piclopastine, picloxydine, picobenzide, picodralazine, picolamine, piconol, picoperine, picoprazole, picotamide, picotrin diolamine, picumast, pidolic acid, pifarnine, pifenate, pifexole, piflutixole, pifoxime, piketoprofen, pildralazine, pilocarpine, pimoclone, pimefylline, pimelautde, pimetacin, pimethixene, pimetine, pimetremide, piminodine, pimobendan, pimondiazole, pimozide, pinacidil, pinadoline, pinafide, pinaverium bromide, pinazepam, pincainide, pindolol, pinolcaine, pinoxepin, pioglitazone, pipacycline, pipamazine, pipaperone, pipazethate, pipebuzone, pipecuronium bromide, pipemidic acid, pipenzolate bromide, pipequaline, piperacetazine, piperacillin, piperamide, piperazine, piperazinedione, piperidolate, piperilate, piperocaine, piperoxan, piperylone, pipobroman, pipoctanone, pipofezine, piposulfan, pipotiazine palmiate, pipoxizine, pipoxolan, pipradimadol, pipradol, pipramadol, pipratecol, piprinhydrinate, piprocurarium iodide, piprofurol, piprozolin, piquindone, piquizil, piracetam, pirandamine, pirarubicin, piraxelate, pirazmonam, pirazolac, pirbenicillin, pirbuterol, pirdonium bromide, pirenoxine, pirenperone, pirenzepine, pirepolol, piretanide, pirfenidone, piribedil, piridicillin, piridocaine, piridoxilate, piridronic acid, pirifibrate, pirindazole, pirinixic acid, pirinixil, piriprost, piriqualone, pirisudanol, piritramide, piritrexim, pirlimycin, pirlindole, pirmagrel, pirmenol, pirnabine, piroctone, pirogliride, piroheptine, pirolate, pirolazamide, piromidic acid, piroxantrone hcl, piroxicam, piroxicam cinnamate, piroxicillin, piroximone, pirozadil, pirprofen, pirquinozol, pirralkonium bromide, pirtenidine, pitenodil, pitofenone, pituxate, pivampicillin, pivenfrine, pivopril, pivoxazepam, pizotyline, plafibride, plaunotol, pleuromulin, plicamycin, podilfen, podophylloxoxin, poldine methylsulfate, polidocanol, ploymyxin, polythiazide, ponalrestat, ponfibrate, porfiromycin, poskine, potassium guaiacolsulfonate, potassium nitrazepate, potassium sodium tartrate, potassium sorbate, potassium thiocyanate, practolol, prajmalium, pralidoxime chloride, pramipexole, pramiracetam, pramiverine, pramoxime, prampine, pranolium chloride, pranoprofen, pranosal, prasterone, pravastatin, praxadine, prazepam, prazepine, praziquantel, prazitone, prazocillin, prazosin, preclamol, prednazate, prednazoline, prednicarbate, prednimustine, prednisolamate, prednisolone, prednisolone acetate, prednisolone hemisuccinate, prednisolone phosphate, prednisolone steaglate, prednisolone tebutate, prednisone, prednival, prednylidene, prefenamate, pregnenolone, pregnenolone succinate, premazepam, prenalterol, prenisteine, prenoverine, prenoxdiazine, prenylamine, pretamazium iodide, pretiadil, pribecaine, pridefine, prideperone, pridinol, prifelone, prifinium bromide, prifuroline, prilocaine, primaperone, primaquine, primidolol, primidone, primycin, prinomide, pristinamycin, prizidilol, proadifen, probarbital, probenecid, probicromil, probucol, procainamide, procaine, procarbazine, procaterol, prochlorperazine, procinolol, procinonide, proclonol, procodazole, procyclidine, procymate, prodeconium bromide, prodilidine, prodipine, prodolic acid, profadol, profexalone, proflavine, proflazepam, progabide, progesterone, proglumetacin, proglumide, proheptazine, proligestone, proline, prolintane, prolonium iodide, promazine, promegestone, promestriene, promethazine, promolate, promoxolane, pronetalol, propacetamol, propafenone, propamidine, propanidid, propanocaine, propantheline bromide, proparacaine, propatyl nitrate, propazolamide, propendiazole, propentofylline, propenzolate, properidine, propetamide, propetandrol, propicillin, propikacin, propinetidine, propiolactone, propiomazine, propipocaine, propiram, propisergide, propiverine, propizepine, propofol, propoxate, propoxycaine, propoxyphene, propranolol, propyl docetrizoate, propylene glycol, propylene glycol monostearate, propyl gallate, propylhexedrine, propyliodone, propylparaben, propylthiouracil, propyperone, propyphenazone, propyromazine bromide, proquazone, proquinolate, prorenoate potassium, proroxan, proscillaridin, prospidium chloride, prostalene, prosulpride, prosultiamine, proterguride, protheobromine, prothipendyl, prothixene, protiofate, protionamide, protirelin, protizinic acid, protokylol, protoveratine, protriptyline, proxazole, proxibarbal, proxibutene, proxicromil, proxifezone, proxorphan, proxyphylline, prozapine, pseudoephedrine, psilocybine, pumiteba, puromycin, pyrabrom, pyran copolymer, pyrantel, pyrathiazine, pyrazinamide, pyrazofurin, pyricarbate, pyridarone, pyridofylline, pyridostigmine bromide, pyridoxine, pyrilamine, pyrimethamine, pyrimitate, pyrinoline, pyrithione zinc, pyrithyldione, pyritidium bromide, pyritinol, pyronine, pyrophenindane, pyrovalerone, pyroxamine, pyrrobutamine, pyrrocaine, pyrroliphene, pyrrolnitrin, pyrvinium chloride, pytamine, quadazocine, quadrosilan, quatacaine, quazepam, quazinone, quazodine, quazolast, quifenadine, quillifoline, quinacainol, quinacillin, quinacrine, quinaldine blue, quinapril, quinaprilat, quinazosin, quinbolone, quincarbate, quindecamine, quindonium bromide, quindoxin, quinestradol, quinestrol, quinethazone, quinetolate, quinezamide, quinfamide, quingestanol acetate, quingestrone, quindine, quinine, quinocide, quinpirole, quinterenol, quintiofos, quinuclium bromide, quinupramine, quipazine, quisultazine, racefemine, racemethionine, racemethorphan, racemetirosine, raclopride, ractopamine, rafoxanide, ralitoline, raloxifene, ramciclane, ramefenazone, ramipril, ramiprilat, ramixotidine, ramnodignin, ranimustine, ranimycin, ranitidine, ranolazine, rathyronine, razinodil, razobazam, razoxane, reboxetine, recainam, reclazepam, relomycin, remoxipride, renanolone, rentiapril, repirinast, repromicin, reproterol, recimetol, rescinnamine, reserpine, resorantel, resorcinol, resorcinol monoacetate, retelliptine, retinol, revenast, ribavirin, riboflavin, riboflavin 5'-phosphate, riboprine, ribostamycin, ridazolol, ridiflone, rifabutin, rifamide, rifampin, rifamycin, rifapentine, rifaximin, rilapine, rilmazafone, rilmenidine, rilopirox, rilozarone, rimantadine, rimazolium metilsulfate, rimcazole, rimexolone, rimiterol, rimoprogin, riodipine, rioprostil, ripazepam, risocaine, risperidone, ristianol, ristocetin, ritanserin, ritiometan, ritodrine, ritropirronium bromide, ritrosulfan, robenidine, rocastine, rociverine, rodocaine, rodorubicin, rofelodine, roflurante, rokitamycin, roletamide, rolgamidine, rolicyclidine, rolicyprine, rolipram, rolitetracycline, rolodine, rolziracetam, romifenone, romifidine, ronactolol, ronidazole, ronifibrate, ronipamil, ronnel, ropitoin, ropivacaine, ropizine, roquinimex, rosaprostol, rosaramicin, rosaramicin butyrate, rosaramicin propionate, rosoxacin, rosterolone, rotamicillin, rotoxamine, rotraxate, roxarsone, roxatidine acetate, roxibolone, roxindole, roxithromycin, roxolonium metilsulfate, roxoperone, rufloxacin, rutamycin, rutin, ruvazone, sabeluzole, saccharin, salacetamide, salafibrate, salantel, salazodine, salazossulfadimedine, salazosulfamide, salazosulfathiazole, salethamide, salfluverine, salicin, salicyl alcohol, salicylamide, salicylanilide, salicylic acid, salinazid, salinomycin, salmefanol, salmeterol, salmisteine, salprotoside, salsalate, salverine, sancycline, sangivamycin, saperconazole, sarcolysin, sarmazenil, sarmoxicillin, sarpicillin, saterinone, satranidazole, savoxepin, scarlet red, scopafungin, scopolamine, seclazone, secnidazole, secobarbital, secoverine, securinine, sedecamycin, seganserin, seglitide, selegiline, selenium sulfide, selprazine, sematilide, semustine, sepazonium chloride, seperidol, sequifenadine, serfibrate, sergolexole, serine, sermetacin, serotonin, sertaconazole, sertraline, setastine, setazindol, setiptiline, setoperone, sevitropium mesilate, sevoflurane, sevopramide, siagoside, sibutramine, siccanin, silandrone, silibinin, silicristin, silidianin, silver sulfadiazine, simetride, simfibrate, simtrazene, simvastatin, sinefungin, sintropium bromide, sisomicin, sitalidone, sitofibrate, sitogluside, sodium benzoate, sodium dibunate, sodium ethasulfate, sodium formaldehyde sulfoxylate, sodium gentisate, sodium gualenate, sodium nitrite, sodium nitroprusside, sodium oxybate, sodium phenylacetate, sodium picofosfate, sodium picosulfate, sodium propionate, sodium stibocaptate, sodium stibogluconate, sodium tetradecyl sulfate, sodium thiosulfate, sofalcone, solasulfone, solpecainol, solypertine, somantadine, sopitazine, sopromidine, soquinolol, sorbic acid, sorbinicate, sorbinil, sorbitan monolaurate, sorbitan monooleate, sorbitan monopalmitate, sorbitan monostearate, sorbitan trioleate, sorbitan tristearate, sorbitol, sorndipine, sotalol, soterenol, spaglumic acid, sparfosic acid, sparsomycin, sparteine, spectinomycin, spiclamine, spiclomazine, spiperone, spiradoline, spiramide, spiramycin, spirapril, spiraprilat, spirendolol, spirgetine, spirilene, spirofylline, spirogermanium, spiromustine, spironolactone, spiroplatin, spirorenone, spirotriazine, spiroxasone, spiroxatrine, spiroxepin, spizofurone, stallimycin, stanolone, stanzolol, stearic acid, stearyl alcohol, stearylsulfamide, steffimycin, stenbolone acetate, stepronin, stercuronium iodide, stevaladil, stibamine glucoside, stibophen, stilbamidine, stilbazium iodide, stilonium iodide, stirimazole, stiripentol, stirocainide, stirifos, streptomycin, streptonicozid, streptonigrin, streptovarycin, streptozocin, strinoline, strychnine, styramate, subathizone, subendazole, succimer, succinylcholine chloride, succinylsulfathiazole, succisulfone, suclofenide, sucralfate, sucrose octaacetate, sudexanox, sudoxicam, sufentanil, sufosfamide, sufotidine, sulazepam, sulbactam, sulbactam pivoxil, sulbenicillin, sulbenox, sulbentine, sulbutiamine, sulclamide, sulconazole, sulfabenz, sulfabenzamide, sulfacarbamide, sulfacecole, sulfacetamide, sulfachlorpyridazine, sulfachrysoidine, sulfaclomide, sulfaclorazole, sulfaclozine, sulfacytine, sulfadiazine, sulfadicramide, sulfadimethoxine, sulfadoxine, sulfaethidole, sulfaguandide, sulfaguanole, sulfalene,sulfaloxic acid, sulfamazone, sulfamerazine, sulfameter, sulfamethazine, sulfamethizole, sulfamethoxazole, sulfamethoxypyridazine, sulfamethoxypyridazine acetyl, sulfametomidine, sulfametrole, sulfamonomethoxine, sulfamoxole, sulfanil amide, sulfanitran, sulfaperin,sulfaphenazole, sulfaproxyline, sulfapyridine, sulfaquinoxaline, sulfarsphenamine, sulfasalazine, sulfasomizole, sulfasuccinamide, sulfasymazine, sulfathiazole, sulfathiourea, sulfatolamide, sulfatroxazole, sulfatrozole, sulfazamet, sulfinalol, sulfinpyrazone, sulfiram, sulfisomidine, sulfisoxazole, sulfisoxazole, sulfobromophthalein, sulfonethylmethane, sulfonmethane, sulfonterol, sulforidazine, sulfoxone sodium, sulicrinat, sulindac, sulisatin, sulisobenzone, sulmarin, sulmazole, sulmepride, sulinidazole, sulocarbilate, suloctidil, sulosemide, sulotroban, suloxifen, sulpiride, sulprosal, sulprostone, sultamicillin, sulthiame, sultopride, sultosilic acid, sultroponium, sulverapride, sumacetamol, sumatriptan, sumetizide, sunagrel, suncillin, supidimide, suproclone, suprofen, suramin, suricainide, suriclone, suxemerid, suxethonium chloride, suxibuzone, symclosene, symetine, synephrine, syrisingopine, taclamine, tacrine, taglutimide, talampicillin, talastine, talbutal, taleranol, talinolol, talipexole, talisomycin, talmetacin, talmetoprim, talniflumate, talopram, talosalate, taloximine, talsupram, taltrimide, tameridone, tameticillin, tametraline, tamitinol, tamoxipen, tampramine, tandamine, taprostene, tartaric acid, tasuldine, taurocholic acid, taurolidine, tauromustine, tauroselcholic acid, taurultam, taxol, tazadolene, tazanolast, tazaburate, tazeprofen, tazifylline, taziprinone, tazolol, tebatizole, tebuquine, teclothiazide, teclozan, tedisamil, tefazoline, tefenperate, tefludazine, teflurane, teflutixol, tegafur, telenzepine, temafloxacin, temarotene, temazepam, temefos, temelastine, temocillin, temodox, temozolomide, temurtide, tenamfetamine, tenilapine, teniloxazine, tenilsetam, teniposide, tenocyclidine, tenonitrozole, tenoxicam, tenylidone, teopranitol, teoprolol, tepirindole, tepoxalin, terazosin, terbinafine, terbucromil, terbufibrol, terbuficin, terbuprol, terbutaline, terciprazine, terconazole, terfenadine, terfluranol, terguride, terizidone, ternidazole, terodiline, terofenamate, teroxalene, teroxirone, terpin hydrate, tertatolol, tesicam, tesimide, testolactone, testosterone, testosterone cypionate, testosterone enanthate, testosterone ketolaurate, testosterone phenylacetate, testosterone propionate, tetrabarbital, tetrabenazine, tetracaine, tetrachloroethylene, tetracycline, tetradonium bromide, tetraethylammonium chloride, tetrahydrozoline, tetramethrin, tetramisole, tetrandrine, tetrantoin, tetrazepam, tetriprofen, tetronasin 5930, tetroquinone, tetroxoprim, tetrydamine, texacromil, thalicarpine, thalidomide, thebacon, thebaine, thenalidine, thenium closylate, thenyldiamine, theobromine, theodrenaline, theofibrate, theophylline, thiabendazole, thiacetarsamide, thialbarbital, thiambutosine, thiamine, thiamiprine, thiamphenicol, thiamylal, thiazesim, thiazinamium chloride, thiazolsulfone, thiethyperazine, thihexinol methylbromide, thimerfonate, thimerosal, thiocarbanidin, thiocarzolamide, thiocolchioside, thiofuradene, thioguanine, thioguanine alpha-deoxyriboside, thioguanine beta-deoxyriboside, thioguanosine, thiohexamide, thioinosine, thiopental, thiopropazate, thioproperazine, thioridazine, thiosalan, thiotepa, thiotetrabarbital, thiothixene, thiouracil, thiphenamil, thiphencillin, thiram, thonzonium bromide, thonzylamine, thozalinone, threonine, thymidine, thymol, thymol iodide, thymopentin, thyromedan, thyropropic acid, tiacrilast, tiadenol, tiafibrate, tiamenidine, tiametonium iodide, tiamulin, tianafac, tianeptine, tiapamil, tiapirinol, tiapride, tiaprofenic acid, tiaprost, tiaramide, tiazofurin, tiazuril, tibalosin, tibenalast sodium, tibenzate, tibezonium iodide, tibolone, tibric acid, tibrofan, tic-mustard, ticabesone propionate, ticarbodine, ticarcillin, ticarcillin cresyl, ticlatone, ticlopidine, ticrynafen, tidiacic, tiemoium iodide, tienocarbine, tienopramine, tienoxolol, tifemoxone, tiflamizole, tiflorex, tifluadom, tiflucarbine, tiformin, tifurac, tigemonam, tigestol, tigloidine, tilbroquinol, tiletamine, tilidine, tiliquinol, tilisolol, tilmicosin, tilomisole, tilorone, tilozepine, tilsuprost, timefurone, timegadine, timelotem, timepidium bromide, timiperone, timobesone acetate, timofibrate, timolol, timonacic, timoprazole, tinabinol, tinazoline, tinidazole, tinisulpride, tinofedrine, tinoridine, tiocarlide, tioclomarol, tioconazole, tioctilate, tiodazosin, tiodonium chloride, tiomergine, tiomesterone, tioperidone, tiopinac, tiopronin, tiopropamine, tiospirone, tiotidine, tioxacin, tioxamast, tioxaprofen, tioxidazole, tioxolone, tipentosin, tipepidine, tipetropium bromide, tipindole, tipredane, tiprenolol, tiprinast, tipropidil, tiprostanide, tiprotimod, tiquinamide, tiquizium bromide, tiratricol, tiropramide, tisocromide, tisopurine, tisoquone, tivandizole, tixadil, tixanox, tixocortol pivalate, tizabrin, tianidine, tizolemide, tizoprolic acid, tobramycin, tobuterol, tocainide, tocamphyl, tocofenoxate, tocofibrate, tocophersolan, todralazine, tofenacin, tofetridine, tofisoline, tofisopam, tolamolol, tolazamide, tolazoline, tolboxane, tolbutamide, tolciclate, toldimfos, tolfamide, tolfenamic acid, tolgabide, tolimidone, tolindate, toliodium chloride, toliprolol, tolmesoxide, tolmetin, tolnaftate, tolnapersine, tolnidamine, toloconium metilsulfate, tolonidine, tolonium chloride, toloxatone, toloxychlorinol, tolpadol, tolpentamide, tolperisone, toliprazole, tolpronine, tolpropamine, tolpyrramide, tolquinzole, tolrestat, toltrazuril, tolufazepam, tolycaine, tomelukast, tomoglumide, tomoxetine, tomoxiprole, tonazocine, topiramate, toprilidine, tonazocine, topiramate, toprilidine, topterone, toquizine, torasemide, toebafylline, toremifene, tosifen, tosufloxacin, tosulur, toyocamycin, toyomycin, traboxepine, tracazolate, tralonide, tramadol, tramazoline, trandolapril, tranexamic acid, tranilast, transcainide, trantelinium bromide, tranylcypromine, trapencaine, trapidil, traxanox, trazilitine, trazium esilate, trazodone, trazolopride, trebenzomine, trecadrine, treloxinate, trenbolone acetate, trengestone, trenizine, trosulfan, trepibutone, trepipam, trepirium iodide, treptilamine, trequensin, trestolone acetate, trethinium tosilate, trethocanoic acid, tretinoin, tretoquinol, triacetin, triafungin, triamcinolone, triamcinolone acetonide, triamcinolone acetonide-phosphate, triamcinolone benetonide, triamcinolone diacetate, triamcinolone furetonide, triamcinolone hexacetonide, triampyzine, triamterene, triazinate, triaziquone, triazolam, tribendilol, tribenoside, tribromoethanol, tribromsalan, tribuzone, triacetamide, trichlormethiazide, trichlormethine, trichloroacetic acid, trichloroethylene, tricribine phosphate, triclabendazole, triclacetamol, triclazate, triclobisonicum chloride, triclocarban, triclodazol, triclofenol, piperazine, triclofos, triclofylline, triclonide, triclosan, tricyclamol chloride, tridihexethyl chloride, trientine, triethylenemelamine, triethylenephosphoramide, trifenagrel, trifezolac, triflocin, triflubazam, triflumidate, trifluomeprazine, trifluoperazine, trifluperidol, triflupromazine, trifluridine, triflusal, trigevolol, trihexyphenidyl, triletide, trilostane, trimazosin, trimebutine, trimecaine, trimedoxime bromide, trimeperidine, trimeprazine, trimetazidine, trimethadione, trimethamide, trimethaphan camsylate, trimethidinium methosulfate, trimethobenzamide, trimethoprim, trimetozine, trimetrexate, trimexiline, trimipramine, trimoprostil, trimoxamine, trioxifene, trioxsalen, tripamide, triparanol, tripelennamine, tripotassium dicitratobismuthate, triprolidine, tritiozine, tritoqualine, trityl cysteine, trixolane, trizoxime, trocimine, troclosene potassium, trofosfamide, troleandomycin, trolnitrate, tromantadine, tromethamine, tropabazate, tropanserin, tropapride, tropatepine, tropenziline bromide, tropicamide, tropigline, tropiprine, tropodifene, trospectomycin, trospium chloride, troxerutin, troxipide, troxolamide, troxonium tosilate, troxypyrrolium tosilate, troxypyrrolium tosilate, truxicurium iodide, truxipicurium iodide, tryparsamide, tryptophan, tryptophane mustard, tuaminoheptane, tubercidine, tubocurarine chloride, tubulozole, tuclazepam, tulobutrol, tuvatidine, tybamate, tylocrebin, tylosin, tyramine, tyropanic acid, tyrosine, ubenimex, ubidecarenone, ubisindine, ufenamate, ufiprazole, uldazepam, ulobetasol, undecoylium chloride, undecyclenic acid, uracil mustard, urapidil, urea, uredepa, uredofos, urefibrate, urethane, uridine, ursodeoxycholic acid, ursucholic acid, vadocaine, valconazole, valdetamide, valdipromide, valine, valnoctamide, valofane, valperinol, valproate pivoxil, valproic acid, valpromide, valtrate, vancomycin hcl, vaneprim, vanillin, vanitolide, vanyldisulfamide, vapiprost, vecuronium bromide, velnacrine maleate, venlafaxine, veradoline, veralipride, verapamil, verazide, verilopam, verofylline, vesnarinone, vetrabutine, vidarabine, vidarabine phophate, vigabatrin, viloxazine, viminol, vinbarbital, vinblastine, vinburnine, vincamine, vincanol, vincantril, vincofos, vinconate, vincristine, vindrburnol, vindesine, vindepidine, vinformide, vinglycinate, vinorelbine, vinpocetine, vinpoline, vinrosidine, vintiamol, vintriptol, vinylbital, vinylether, vinzolidine, viomycin, viprostol, viqualine, viquidil, virginiamycin factors, viroxime, visnadine, visnafylline, vitamin e, volazocine, warfarin, xamoterol, xanoxic acid, xanthinol niacinate, xanthiol, xantifibrate, xantocillin, xenalipin, xenazoic acid, xenbucin, xenipentone, xenthiorate, xenygloxal, xenyhexenic acid, xenytropium bromide, xibenolol, xibornol, xilobam, ximoprofen, xinidamine, xinomiline, xipamide, xipranolol, xorphanol, xylamidine, xylazine, xylocoumarol, xylometazoline, xyloxemine, yohimbic acid, zabicipril, zacopride, zafuleptine, zaltidine, zapizolam, zaprinast, zardaverine, zenazocine mesylate, zepastine, zeranol, zetidoline, zidapamide, zidometacin, zidovudine, zilantel, zimeldine, zimidoben, zinc acetate, zinc phenolsulfonate, zinc undecylenate, zindotrine, zindoxifene, zinoconazole, zinterol, zinviroxime, zipeprol, zocainone, zofenopril, zoficonazole, zolamine, zolazepam, zolenzepine, zolertine, zolimidine, zoliprofen, zoloperone, zolpidem, zomebazam, zomepirac, zometapine, zonisamide, zopiclone, zorubicin, zotepine, zoxazolamine, zuclomiphene, zuclophenthixol, zylofuramine.

The following non-limitative examples serve to illustrate the concept of multiple receptor specificity. Other combinations of vectors, spacers and reporters and conjugation technologies leading to multiple vector incorporation are also considered relevant to this invention. Confirmation of the microparticulate nature of products is performed using microscopy as described in WO-A-9607434. Ultrasonic transmission measurements may be made using a broadband transducer to indicate suspensions of products giving an increased sound beam attenuation compared to a standard. Flow cytometric analysis of products can be used to confirm attachment of antibodies thereto. The ability of targeted agents to bind specifically to cells expressing a target may be studied by microscopy and/or using a flow chamber containing immobilised cells, for example employing a population of cells expressing the target structure and a further population of cells not expressing the target. Radioactive, fluorescent or enzyme-labelled streptavidin/avidin may be used to analyse biotin attachment.

EXAMPLE 1

Preparation and Biological Evaluation of Multiple-specific Gas-containing Microbubbles of DSPS 'Doped' with a Lipopeptide Consisting of a Heparin Sulphate Binding Peptide (KRKR) (SEQ ID NO:1) and a Fibronectin Peptide (WOPPRARI) (SEQ ID NO. 2).

This example is directed at the preparation of targeted microbubbles comprising multiple peptidic vectors arranged in a linear sequence.

a) Synthesis of a Lipopeptide Consisting of a Heparin Sulphate Binding Peptide (KRKR) (SEQ ID NO:1) and Fibronectin Peptide (WOPPRARI) (SEQ ID NO:2).

The simultaneous removal of peptide from the resin and side-chain protecting groups was carried out in TFA containing 5% phenol, 5% EDT, 5% anisole and 5% $H_2O$ for 2 hours giving a crude product yield of 150 mg. Purification by preparative HPLC (Vydac 218TP1022 column) of a 40 mg aliquot of crude material was carried out using a gradient of 70 to 100% B over 40 min (A=0.1% TFA/water and B=MeOH) at a flow rate of 9 mL/min. After lyophilization 16 mg of pure material was obtained (Analytical HPLC; Gradient, 70–100% B where B=MeOH, A=0.01% TFA/water: column–vydac 218TP54: Detection–UV 260 and fluorescence, $Ex_{280}$, $Em_{350}$–product retention time=19.44 min). Further product characterization was carried out using MALDI mass spectrometry; expected, M+H at 2198, found, at 2199.

b) Preparation of Gas-containing Microbubbles of DSPS 'Doped' with a Multiple-specific Lipopeptide Consisting of a Heparin Sulphate Binding Peptide (KRKR) (SEQ ID NO:1) and Fibronectin Peptide (WOPPRARI) (SEQ ID NO:2).

DSPS (Avanti, 4.5 mg) and lipopeptide from a) (0.5 mg) were weighed into each of 2 vials and 0.8 mL of a solution of 1.4% propylene glycol/2.4% glycerol was added to each vial. The mixture was warmed to 80° C. for 5 minutes (vials shaken during warming). The samples were cooled to room temperature and the head space flushed with perfluorobutane

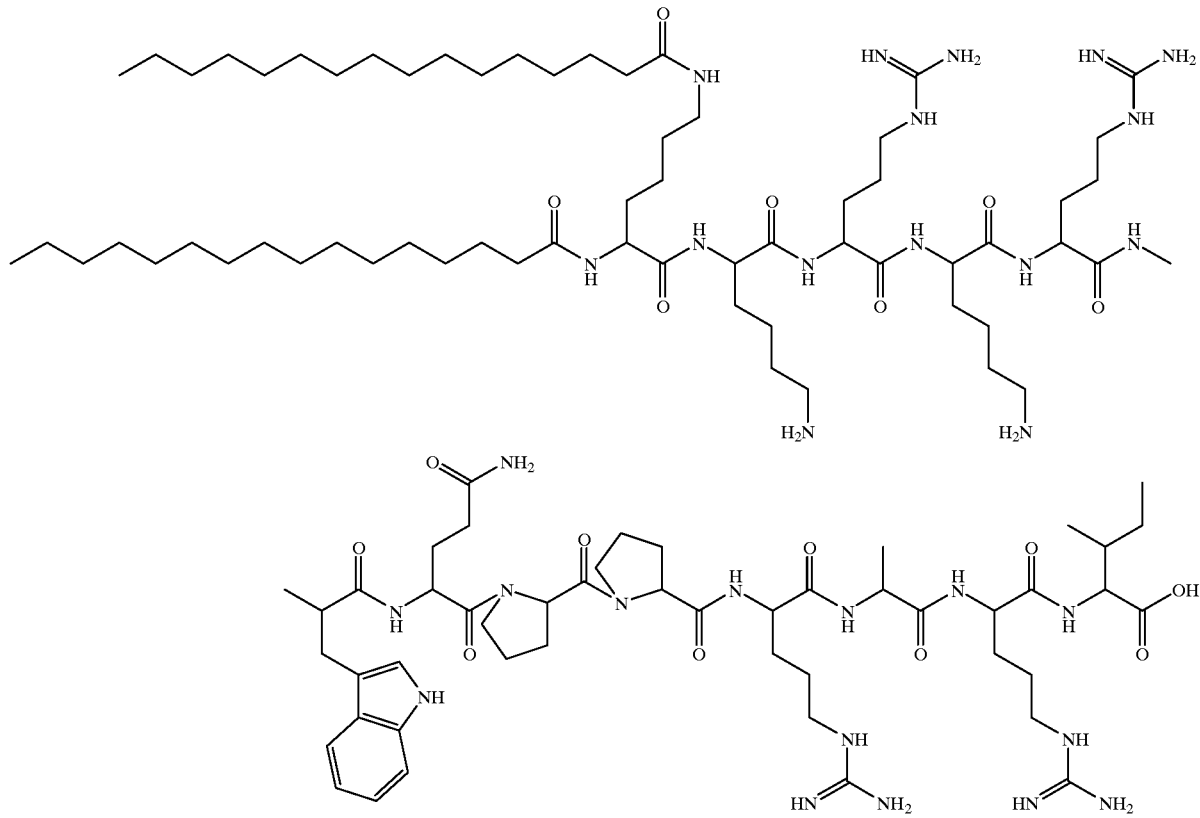

SEQ ID NO: 3

The lipopeptide was synthesised on a ABI 433A automatic peptide synthesiser starting with Fmoc-Ile-Wang resin (Novabiochem) on a 0.1 mmol scale using 1 mmol amino acid cartridges. All amino acids and palmitic acid were preactivated using HBTU before coupling.

gas. The vials were shaken in a cap mixer for 45 s and the microbubbles rolled overnight. Bubbles were washed several times with deionised water and analysed by Coulter counter (Size: 1–3 micron (87%), 3–5 micron (11.5%)) and acoustic attenuation (frequency max att.: 3.5 MHz). The microbubbles were stable at 120 mm Hg. MALDI mass spectral analysis was used to confirm incorporation into DSPS microbubbles as follows; ca. 0.05–0.1 mL of microbubble suspension was transferred to a clean vial and 0.05–0.1 mL methanol added. The suspension was sonicated for 30 s and the solution analysed by MALDI MS. Positive mode gave M+H at 2200, expected for lipopeptide, 2198.

c) In Vitro Study of Gas-containing Microbubbles of DSPS 'Doped' with a Multiple-specific Lipopeptide Consisting of a Heparin Sulphate Binding Peptide (KRKR) (SEQ ID NO:1) and Fibronectin Peptide (WOPPRARI) (SEQ ID NO:2): Binding to Endothelial Cells Under Flow Conditions The human endothelial cell line ECV 304, derived from a normal umbilical cord (ATCC CRL-1998) was cultured in 260 mL Nunc culture flasks (chutney 153732) in RPMI 1640 medium (Bio Whittaker) to which L-Glutamine 200 mM, Penicillin/ Streptomycin (10.000 U/mL and 10.000 mcg/mL) and 10% Fetal Bovine Serum (Hyclone Lot no. AFE 5183) were added.

The cells were subcultured with a split ratio of 1:5 to 1:7 when reaching confluence. Cover-glasses, 22 mm in diameter (BDH, Cat no. 406/0189/40) were sterilised and placed on the bottom of 12 well culture plates (Costar) before cells in 0,5 mL complete medium with serum was added on top. When the cells reached confluence the coverslips were placed in a custom made flow-chamber. The chamber consists of a groove carved into a glass plate upon which the cover slip with cells was placed with the cells facing the groove forming a flow channel.

Ultrasound microbubbles from section b) were passed from a reservoir held at 37 degree Celsius through the flow chamber and back to the reservoir using a peristaltic pump. The flow rate was adjusted to simulate physiological relevant shear rates. The flow chamber was placed under a microscope and the interaction between the microspheres and cells viewed directly. A camera mounted on the microscope was connected to a colour video printer and a monitor.

A gradual accumulation of the microbubbles on the cells took place which was dependant on the flow rate. By increasing the flow rate the cells started to become detached from the coverslip, the microbubbles were still bound to the cells. Control bubbles not carrying the vector did not adhere to the endothelial cells and disappeared from the cells under minimal flow conditions.

d) In Vivo Experiment in Dog

Case 1)

A 22 kg mongrel dog was anaesthetized with pentobarbital and mechanically ventilated. The chest was opened by a midline sternotomy, the anterior pericardium was removed, and a 30 mm gelled silicone rubber spacer was inserted between the heart and a P5–3 transducer of an ATL HDI-3000 ultrasound scanner. The scanner was set for intermittent short axis imaging once in each end-systole by delayed EGC triggering.

A net volume of 2 mL of microbubbles from b) were injected as a rapid intravenous bolus. 3 seconds later, the imaged right ventricle was seen to contain contrast material, another 3 seconds later, the left ventricle was also filled, and a transient attenuation shadow that obscured the view of the posterior parts of the left ventricle was observed. A substantial increase in brightness of the myocardium was seen, also in the portions of the heart distal to the left ventricle when the attenuation shadow subsided.

After passage of the inital bolus, the ultrasound scanner was set to continuous, high frame rate high output power imaging, a procedure known to cause destruction of utrasound contrast agent bubbles in the imaged tissue regions. After a few seconds, the scanner was adjusted back to its initial setting. The myocardium was then darker, and closer to the baseline value. Moving the imaged slice to a new position resulted in re-appearance of contrast effects, moving the slice back to the initial position again resulted in a tissue brightness again close to baseline.

Case 2) [comparative]

A net volume of 2 mL microbubbles prepared in an identical manner to b) above with the exception that no lipopeptide was included in the preparation was injected, using the same imaging procedure as above. The myocardial echo enhancement was far less intense and of shorter duration than observed in case 1. At the completion of the left ventricular attenuation phase, there was also almost complete loss of myocardial contrast effects, and a myocardial echo increases in the posterior part of the left ventricle as in case 1 was not observed.

EXAMPLE 2

Multiple-specific Gas-containing Microbubbles of DSPS 'Doped' with RGDC-(SEQ ID NO:4)-Mal-PEG$_{2000}$-DSPE and a Lipopeptide Consisting of a Heparin Sulphate Binding Peptide (KRKR) (SEQ ID NO:1, and Fibronectin Peptide (WOPPRARI) (SEQ ID NO:2)

This example is directed at the preparation of targeted microbubbles comprising multiple peptidic vectors.

a) Synthesis of 3-Maleimidopropionylamido-PEG$_{2000}$-acyl Distearoyl Phosphatidylethanolamine (PE-PEG-MAL)

A mixture of distearoyl phosphatidyl ethanolamine (DSPE), (37.40 mg, 0.005 mmol), N-hydroxysuccinimido-PEG$_{2000}$-maleimide, NHS-PEG-MAL, (100 mg, 0.25 mmol) and triethylamine (35 μl, 0.25 mmol) in a solution of chloroform/methanol (3:1) was stirred at room temperature for 24 hours. After evaporation of the solvents under reduced pressure, the residue was purified by flash chromatography (chloroform/methanol, 8:2). The product was obtained as a white wax, 92 mg (66%) and structure was verified by NMR and maldi-MS.

b) Synthesis of RGDC (SEQ ID NO:4)

The RGDC (SEQ ID NO:4) peptide was synthesised on a ABI 433A automated peptide synthesiser (0.25 mmol scale, Fmoc-Cys(Trt)-Wang resin, (Novabiochem). All amino acids were activated using HBTU. The crude peptide was removed from the resin and simultaneously deprotected in TFA containing 5% EDT, 5% phenol and 5% water. Following evaporation of the excess cleavage solution the peptide was precipitated and triturated several times with diethyl ether before air drying. The crude peptide was purified by preparative hplc and fractions containing pure product combined and freeze dried. Final characterisation was performed using analytical hplc and MALDI MS.

c) Preparation of Multiple-specific Gas-filled Microbubbles Encapsulated by Phosphatidylserine and 'Doped' with RGDC-(SEQ ID NO:4)-Mal-PEG$_{3400}$-DSPE and a Lipopeptide Comprising a Heparin Sulphate Binding Peptide (KRKR) (SEQ ID NO:1) and Fibronectin Peptide (WOPPRARI) (SEQ ID NO:2).

DSPS (Avanti, 5.0 mg), lipopeptide (0.5 mg) from example 1a)and PE-PEG-MAL (0.5 mg) from section a) was weighed into a clean vial and 1.0 mL of a solution of 1.4% propylene glycol/ 2.4% glycerol added. The mixture was sonicated for 3–5 mins, warmed to 80° C. for 5 minutes then filtered through a 4.5 micron filter. The mixture was cooled to room temperature and the head space flushed with perfluorobutane gas. The vials were shaken in a cap mixer for 45 s and the microbubbles centrifuged at 1000 rpm for 3 minutes. The infranatant was exchanged with 1 mL of PBS containing 1 mg of the peptide RGDC (SEQ ID NO:4) and the pH adjusted to 8. The conjugation reaction was allowed to proceed for 2 h. The bubbles were washed in PBS then with water until all unreacted RGDC (SEQ ID NO:4) had been removed from the infranatant as observed by MALDI-MS. The microbubbles were further analysed by Coulter counter (98% between 1 and 7 micron).

d) In Vitro Binding Assay.

The binding of microbubbles to endothelial cells was carried out under flow conditions using the in vitro assay described in example 1. c). A gradual accumulation of the microbubbles on the cells took place which was dependant on the flow rate. Control bubbles not carrying the vectors did not adhere to the endothelial cells detaching from the cells under minimal flow conditions.

EXAMPLE 3

Preparation of Multiple-specific Gas-containing Microbubbles encapsulated with DSPS and Thiolated anti-CD62-Mal-$PEG_{2000}$-PE and Thiolated-anti-ICAM-1-Mal-$PEG_{2000}$-PE This example is directed at the preparation of microbubbles comprising multiple antibody vectors for targeted ultrasound.

a) Preparation of Gas-containing Microbubbles Encapsulated with DSPS and PE-$PEG_{2000}$-MAL DSPS (Avanti, 4.5 mg) and PE-$PEG_{2000}$-Maleimide from example 2a)(0.5 mg) were weighed into a clean vial and 1 mL of a solution of 1.4% propylene glycol/2.4% glycerol added. The mixture was warmed to 80° C. for 5 minutes then filtered through a 4.5 micron filter. The sample was cooled to room temperature and the head space flushed with perfluorobutane gas. The vials were shaken in a cap mixer for 45 s and the microbubbles washed three times with distilled water.

b) Thiolation of Anti-CD62 and Anti-ICAM-1 Antibodies

To 0.3 mg each of anti-CD62 and anti-ICAM-1 antibodies dissolved in PBS buffer (pH 7, 0.5 mL) was added Traut's reagent and the solutions stirred at room temperature . for 1 h. Excess reagent was separated from the modified protein on a NAP-5 column (Pharmacia).

c) Conjugation of Thiolated Anti-CD62 and Anti-ICAM-1 Antibodies to Gas-containing Microbubbles Encapsulated with DSPS and DSPE-$PEG_{2000}$-MAL 0.5 mL of the mixed thiolated antibody preparation from b) was added to an aliquot of microbubbles from a) and the conjugation reaction allowed to proceed for 30 min on a roller table. Following centrifugation at 2000 rpm for 5 min the infranatant was removed. The microbubbles were washed a further three times with water.

The PEG spacer length may also be varied to include longer e.g. $PEG_{3400}$ and $PEG_{5000}$ or shorter e.g. $PEG_{600}$ or $PEG_{800}$ chains. Addition of a third antibody such as thiolated-anti-CD34 is also envisaged.

EXAMPLE 4

Targeted Multiple-specific Gas-containing Microbubbles of DSPS Coated Non-covalently with Polylysine and a Fusion Peptide Comprising a PS Binding Component and a Fibronectin Peptide Sequence $NH_2$.F.N.F.R.L.K.A.G.O.K.I.R.F.G.G.G.G.W.O.P.P.R.A.I. OH. (SEQ ID NO:5)

a) Synthesis of PS Binding/Fibronectin Fragment Fusion Peptide $NH_2$.F.N.F.R.L.K.A.G.O.K.I.R.F.G.G.G.G.W.O.P.P.R.A.I. OH. (SEQ ID NO:5)

The peptide was synthesised on an ABI 433A automatic peptide synthesiser starting with Fmoc-Ile-Wang resin (Novabiochem) on a 0.1 mmol scale using 1 mmol amino acid cartridges. All amino acids were preactivated using HBTU before coupling.

The simultaneous removal of peptide from the resin and side-chain protecting groups was carried out in TFA containing 5% phenol , 5% EDT and 5% $H_2O$ for 2 hours giving a crude product yield of 302 mg. Purification by preparative HPLC (Vydac 218TP1022 column) of a 25 mg aliquot of crude material was carried out using a gradient of 20 to 40% B over 40 min (A=0.1% TFA/water and B=0.1% TFA/acetonitrile) at a flow rate of 9 mL/min. After lyophilization 10 mg of pure material was obtained (Analytical HPLC; Gradient, 20 to 50% B where B=0.1% TFA/acetonitrile, A=0.01% TFA/water: column–vydac 218TP54:Detection–UV 214 and 260 nm–product retention time=12.4 min). Further product characterization was carried out using MALDI mass spectrometry; expected, M+H at 2856, found, at 2866.

b) Preparation of Microbubbles of DSPS Coated Non-covalently with Polylysine and the PS Binding/Fibronectin Fragment Fusion Peptide $NH_2$.F.N.F.R.L.K.A.G.O.K.I.R.F.G.G.G.G.W.O.P.P.R.A.I. OH. (SEQ ID NO:5)

DSPS (5 mg, Avanti) was weighed into a clean vial along with poly-L-lysine (Sigma, 0.2 mg) and peptide from a) above (0.2 mg). To the vial was added 1.0 mL of a solution of 1.4% propylene glycol/ 2.4% glycerol. The mixture was warmed to 80° C. for 5 minutes. The sample was cooled to room temperature and the head space flushed with perfluorobutane gas. The vials were shaken in a cap mixer for 45 s and the microbubbles centrifuged at 1000 rpm for 3 minutes.

Following extensive washing with water, PBS and water the final solution was examined for polylysine and peptide content using MALDI MS. No polypeptide material was observed in the final wash solution.

Acetonitrile (0.5 mL) was then added and the microbubbles destroyed by sonication. Analysis of the resulting solution for polylysine and PS-binding/fibronectin fusion peptide was then carried out using MALDI MS. The results were as follows:

|  | MALDI expected | MALDI found |
| --- | --- | --- |
| Poly-L-lysine | 786, 914, 1042, 1170 | 790, 919, 1048, 1177 |
| DSPS-bindng peptide | 2856 | 2866 |

The spacer element contained within the PS binding/Fibronectin fusion peptide (-GGG-) can also be replaced with other spacers such as $PEG_{2000}$ or poly alanine (-AAA-). It is also envisaged that a form of pre-targeting may be employed, whereby the DSPS binding/Fibronectin fragment fusion peptide is firstly allowed to associate with cells via the fibronectin peptide binding. This is followed by administration of PS microbubbles which then bind to the PS binding peptide.

EXAMPLE 5

Multiple-specific Gas-containing Microbubbles Encapsulated with Phosphatidylserine and Biotin-$PEG_{3400}$-alanyl-cholesterol and Functionalised with Streptavidin/biotinyl-endothelin-1 Peptide (biotin-D-Trp-Leu-Asp-Ile-Ile-Trp.OH) (SEQ ID NO:6) and Biotinyl-fibrin-anti-polymerant Peptide (biotin-GPRPPERHOS.$NH_2$) (SEQ ID NO:7)

This example is directed at the preparation of targeted ultrasound microbubbles whereby streptavidin is used as a linker between biotinylated reporter(s) and vector(s).

a) Synthesis of Biotin-PEG$_{3400}$-β-Alanine Cholesterol

To a solution of cholesteryl-β-alanine hydrochloride (15 mg, 0.03 mmol) in 3 mL chloroform/wet methanol (2.6:1), was added triethylamine (42 mL, 0.30 mmol). The mixture was stired for 10 minutes at room temperature and a solution of biotin-PEG$_{3400}$-NHS (100 mg, 0.03 mmol) in 1,4-dioxan (1 mL) was added dropwise. After stirring at room temperature for 3 h, the mixture was evaporated to dryness and the residue purified by flash chromatography to give white crystals, yield ; 102 mg (89%). The structure was verified by MALDI-MS and NMR.

b) Synthesis of Biotinylated Endothelin-1 Peptide (biotin-D-Trp-Leu-Asp-Ile-Ile-Trp.OH) (SEQ ID NO:6)

The peptide was synthesised on a ABI 433A automatic peptide synthesiser starting with Fmoc-Trp(Boc)-Wang resin (Novabiochem) on a 0.1 mmol scale using 1 mmol amino acid cartridges. All amino acids were preactivated using HBTU before coupling.

The simultaneous removal of peptide from the resin and side-chain protecting groups was carried out in TFA containing 5% anisole and 5% H$_2$O for 2 hours giving a crude product yield of 75 mg. Purification by preparative HPLC (Vydac 218TP1022 column) of a 20 mg aliquot of crude material was carried out using a gradient of 30 to 80% B over 40 min (A=0.1% TFA/water and B=0.1% TFA/acetonitrile) and a flow rate of 9 mL/min. After lyophilization of the pure fractions 2 mg of pure material was obtained (Analytical HPLC; Gradient, 30–80% B where B=0.1% TFA/acetonitrile, A=0.01% TFA/water: column–vydac 218TP54:Detection–UV 214 nm–product retention time= 12.6 min). Further product characterization was carried out using MALDI mass spectrometry; expected, M+H at 1077, found, 1077.

c) Synthesis of Biotinyl-fibrin-anti-polymerantPBeptide (Biotin-GPRPPERHOS.NH$_2$) (SEQ ID NO:7)

This peptide was synthesised and purified using similar protocols to those described in section b) above. The pure product was characterised by hplc and MALDI MS.

d) Preparation of Multiple-specific Gas-filled Microbubbles Encapsulated with Phosphatidylserine and Biotin-PEG$_{3400}$-β-Alanine Cholesterol DSPS (Avanti, 4.5 mg) and biotin-PEG$_{3400}$-β-Alanine cholesterol from section a) (0.5 mg) were weighed into a vial and 0.8 mL of a solution of 1.4% propylene glycol/ 2.4% glycerol added. The mixture was warmed to 80° C. for 5 minutes (vials shaken during warming). The sample was cooled to room temperature and the head space flushed with perfluorobutane gas. The vial was shaken in a cap mixer for 45 s and the microbubbles rolled overnight. The microbubble suspension was washed several times with deionised water and analysed by Coulter counter and acoustic attenuation.

e) Conjugation with Fluorescein Labelled Streptavidin and Biotinylated Peptides from Section b) and c).

To the microbubble preparation from d) was added fluorescein conjugated streptavidin (0.2 mg) dissolved in PBS (1 mL). The bubbles were placed on a roller table for 3 h at room temperature. Following extensive washing with water and analysis by fluorescence microscopy the microbubbles were incubated in 1 mL of PBS containing biotinyl-Endothelin-1 peptide (0.5 mg) and biotinyl-Fibrin-anti-polymerant peptide (0.5 mg) from sections b) and c) respectively for 2 h. Extensive washing of the microbubbles was performed to remove unconjugated peptide.

EXAMPLE 6

Multiple-specific Gas-filled Microbubbles Encapsulated with Phosphatidylserine and a Biotinylated Lipopeptide used to Prepare a Streptavidin 'Sandwich' with a Mixture of Biotinyl-endothelin-1 Peptide (biotin-D-Trp-Leu-Asp-Ile-Ile-Trp.OH) (SEQ ID NO:6) and Biotinyl-fibrin-anti-polymerant peptide (biotin-GPRPPERHOS.NH$_2$) (SEQ ID NO:7)

a) Synthesis of Lipopeptide Dipalmitoyl-lysinyl-tryptophanyl-lysinyl-lysinyl-lysinyl(biotinyl)-glycine (SEQ ID NO:8)

The lipopeptide was synthesised on a ABI 433A automatic peptide synthesiser starting with Fmoc-Gly-Wang resin (Novabiochem) on a 0.1 mmol scale using 1 mmol amino acid cartridges. All amino acids and palmitic acid were preactivated using HBTU before coupling.

The simultaneous removal of peptide from the resin and side-chain protecting groups was carried out in TFA containing 5% phenol , 5% EDT, 5% anisole and 5% H$_2$O for 2 hours giving a crude product yield of 150 mg. Purification by preparative HPLC (Vydac 218TP1022 column) of a 40 mg aliquot of crude material was carred out using a gradient of 70 to 100% B over 40 min (A=0.1% TFA/water and B=MeOH) at a flow rate of 9 mL/min. After lyophilization 14 mg of pure material (Analytical HPLC; Gradient, 70–100% B where B=MeOH, A=0.01% TFA/water: column–vydac 218TP54: Detection–UV 260 and fluorescence, Ex280, Em350–product retention time=22 min). Further product characterization was carried out using MALDI mass spectrometry; expected, M+H at 1478, found, 1471.

b) Preparation of Gas-containing Microbubbles of DSPS 'Doped' with the Biotinylated Lipopeptide Sequence from Section a)

DSPS (Avanti, 4.5 mg) and lipopeptide from a) (0.5 mg) were weighed into each of 2 vials and 0.8 mL of a solution of 1.4% propylene glycol/2.4% glycerol was added to each vial. The mixture was warmed to 80° C. for 5 minutes (vials shaken during warming). The samples were cooled to room temperature and the head space flushed with perfluorobutane gas. The vials were shaken in a cap mixer for 45 s and the microbubbles formed rolled overnight. The microbubbles were washed several times with deionised water and analysed by Coulter counter and acoustic attenuation. MALDI mass spectral analysis was used to confirm incorporation into DSPS microbubbles as described in example 1b).

c) Preparation of Multiple-specific Gas-filled Microbubbles Encapsulated with Phosphatidylserine and a Biotinylated Lipopeptide and Functionalised with Streptavidin/biotinyl-endothelin-1 Peptide (biotin-D-Trp-Leu-Asp-Ile-Ile-Trp.OH) (SEQ ID NO:6)/Biotinyl-Fibrin-Anti-Polymerant Peptide (biotin-GPRPPERHOS.NH$_2$) (SEQ ID NO:7)

The microbubble preparation from b) above was treated in an analogous manner to that described in example 5 section e).

EXAMPLE 7

Multiple-specific Gas-filled Microbubbles Encapsulated with Phosphatidylserine and Biotin-DPPE used to Prepare a Streptavidin 'Sandwich' with a Mixture of Biotinyl-endothelin-1 Peptide (biotin-D-Trp-Leu-Asp-Ile-Ile-Trp.OH) (SEQ ID NO:6) and Biotinyl-fibrin-anti-polymerant Peptide (biotin-GPRPPERHOS.NH$_2$) (SEQ ID NO:7)

a) Preparation of Biotin Containing Microbubbles.

To a mixture of phosphatidylserine (5 mg, Avanti) and biotin-DPPE (0.6 mg, Pierce) in a clean vial was added 5% propyleneglycol-glycerol in water (1 mL). The dispersion was heated to 80° C. for 5 minutes and then cooled to ambient temperature. The head space was then flushed with perfluorobutane and the vial shaken in a cap-mixer for 45 seconds. After centrifugation the infranatant was removed and the microbubbles formed washed extensively with water.

b) Conjuaation of Gas-filled Microbubbles Encapsulated with Phosphatidylserine and Biotin-DPPE with Streptavidin and a Mixture of Biotinyl-Endothelin-1 (biotin-D-Trp-Leu-Asp-Ile-Ile-Trp.OH) (SEQ ID NO:6) and Biotinyl-Fibrin-anti-polymerant Peptide (biotin-GPRPPERHOS.NH$_2$) (SEQ ID NO:7)

The procedure detailed in example 5 section e) was followed.

EXAMPLE 8

Multiple-specific Gas-filled Microbubbles Encapsulated with Phosphatidylserine, Streptavidin-Succ-PEG-DSPE and a Mixture of Biotinylated Human Endothelium IaG Antibody and Biotinylated Transferrin a) Synthesis of Succ-PEG$_{3400}$-DSPE NH$_2$-PEG$_{3400}$-DSPE is carboxylated using succinic anhydride, e.g. by a similar method to that described by Nayar, R. and Schroit, A. J. in *Biochemistry* (1985) 24, 5967–71.

b) Preparation of Gas-filled Microbubbles Encapsulated with Phosphatidylserine and Succ-PEG$_{3400}$-DSPE To a mixture (5 mg) of phosphatidylserine (90–99.9 mol %) and Succ-PEG$_{3400}$-DSPE (10–0.1 mol %) is added 5% propyleneglycol-glycerol in water (1 mL). The dispersion is heated to not more than 80° C. for 5 minutes and then cooled to ambient temperature. The dispersion (0.8 mL) is transferred to a vial (1 mL) and the head space is flushed with perfluorobutane. The vial is shaken in a cap-mixer for 45 seconds, whereafter the sample is put on a roller table. After centrifugation the infranatant is exchanged with water and the washing is repeated.

c) Coupling of Streptavidin to Gas-filled Microbubbles Encapsulated with Phosphatidylserine and Succ-PEG$_{3400}$-DSPE Streptavidin is covalently bound to Succ-PEG$_{3400}$-DSPE in the membrane by standard coupling methods using a water-soluble carbodiimide. The sample is placed on a roller table during the reaction. After centrifugation the infranatant is exchanged with water and the washing is repeated. The functionality of the attached streptavidin is analysed by binding, e.g. to fluorescently labeled biotin, biotinylated antibodies (detected with a fluorescently labeled secondary antibody) or biotinylated and fluorescence- or radioactively-labeled oligonucleotides. Analysis is performed by fluorescence microscopy or scintillation counting.

d) Preparation of Multiple-specific Gas-filled Microbubbles Encapsulated with Phosphatidylserine and Streptavidin-Succ-PEG$_{3400}$-DSPE Non-covalently Functionalised with Biotinylated Human Transferrin and Human Endothelium IgG Antibody Microbubbles from section c) are incubated in a solution containing human transferrin and human endothelium IgG antibody biotinylated using the method described by Bayer et al., Meth. Enzymol., 62, 308. The vector-coated microbubbles are washed as described above.

EXAMPLE 9

Multiple-specific Gas-filled Microbubbles Encapsulated with Phosphatidylserine/streptavidin-Succ-PEG-DSPE and the Oligonucleotides Biotin-GAAAGGTAGTGGGGTCGTGTGCCGG (SEQ ID NO:9) and Biotin-GGCGCTGATGATGTTGTTGATTCTT (SEQ ID NO:10)

a) Synthesis of Succ-PEG$_{3400}$-DSPE

Described in example 8 a)

b) Preparation of Gas-filled Microbubbles Encapsulated with Phosphatidylserine and Succ-PEG$_{3400}$-DSPE Described in example 8b).

c) Coupling of Streptavidin to Gas-filled Microbubbles Encapsulated with Phosphatidylserine and Succ-PEG$_{3400}$-DSPE Described in example 8 c).

d) Preparation of Gas-filled Microbubbles Encapsulated with Phosphatidylserine/streptavidin-Succ-PEG-DSPE and the Oligonucleotides Biotin-GAAAGGTAGTGGGGTCGTGTGCCGG (SEQ ID NO:9) and Biotin-GGCGCTGATGATGTTGTTGATTCTT (SEQ ID NO:10)

Microbubbles from section c) are incubated in a solution containing a mixture of biotin-GAAAGGTAGTGGGGTCGTGTGCCGG (SEQ ID NO:9) and biotin-GGCGCTGATGATGTTGTTGATTCTT (SEQ ID NO:10). The oligonucleotide-coated microbubbles are washed as described above. Binding of the oligonucleotide to the bubbles is detected e.g. by using fluorescent-labeled oligonucleotides for attachment to the bubbles, or by hybridising the attached oligonucleotide to a labeled (fluorescence or radioactivity) complementary oligonucleotide. The functionality of the oligonucleotide-carrying microbubbles is analysed, e.g. by hybridising the bubbles with immobilized DNA-containing sequences complementary to the attached oligonucleotide.

Other useful examples include an oligonucleotide complementary to ribosomal DNA (of which there are many copies per haploid genome) and an oligonucleotide complementary to an oncogene (e.g. ras of which there is one copy per haploid genome) are used.

EXAMPLE 10

Multiple-specific Gas-filled Microbubbles Encapsulated with Phosphatidylserine and Phosphatidylethanolamine Covalently Functionalised with the Fibronectin and Transferrin Proteins a) Microbubbles Preparation.

DSPS (Avanti, 4.5 mg) and DSPE (Avanti, 1.0 mg) were weighed into a clean vial and 1 mL of a solution of 1.4% propylene glycol/2.4% glycerol added. The mixture was warmed to 80° C. for 5 minutes then filtered through a 4.5 micron filter. The sample was cooled to room temperature and the head space flushed with perfluorobutane gas. The vial was shaken in a cap mixer for 45 s and the microbubbles washed two times with distilled water then resuspended in 0.1 M sodium borate buffer pH 9.

b) Modification of Fibronectin/Transferrin.

Fibronectin (0.5 mg) and transferrin (1.3 mg) were mixed in PBS and a solution containing NHS-fluorescin in DMSO added. The mixture was stirred at room temperature for 1 hour then the protein purified on a Superdex 200 column. The fluorescein-labelled protein mixture in phosphate buffer pH 7.5 was freeze dried.

c) Microbubble Modification.

The freeze-dried product from b) was re-dissolved in 0.5 mL water and to the fluorescein labelled fibronectin/transferrin mixture was added 0.1 mmol of the crosslinker SDBP (Pierce). The solution was incubated on ice for 2 hours, charged on a NAP-5 column and eluted with PBS. To this was added 1 mL of the microbubble suspension from a) and incubation allowed to proceed for 2 h at room temperature on a roller table. Unreacted material was removed by allowing the microbubbles to float then replacing the buffer with water, this process was repeated 3 times.

EXAMPLE 11

Preparation of Multiple-specific Hollow Polymer Particles Incorporating Avidin in the Polymer Wall Conjugated with the Oligonucleotide Biotin-GGCGCTGATGATGTTGTTGATTCTT (SEQ ID NO:10) and the Endothelin-1 Peptide Biotin-D-Trp-Leu-Asp-Ile-Ile-Trp.OH (SEQ ID NO:6)

This example is directed at the preparation of polymeric ultrasound contrast agents comprising multiple vectors attached to non-surfactant for targeting/therapeutic applications.

a) Preparation of Polymer Particles Incorporating Avidin in the Polymer Wall

Hollow polymer particles of P73 (as described in patent WO 96/07434) containing avidin were prepared by a process involving the freeze-drying of an oil-in-water emulsion using the following procedure: An oil solution was prepared by dissolving 0.25 g of the biodegradable polymer P73 [poly(ethylidene bis(16-hydroxyhexadecanoate) co (adipic acid)] in 5 mL of camphene at 60° C. To 0.2 mL of the oil solution was added 2 mg avidin. An aqueous solution was then prepared by dissolving 0.4 g of the polymer, a-(16-hexadecanoyloxyhexadecanoyl)-w-methoxypolyoxyethylene ester, in 20 mL of water at 60° C. The oil solution (0.2 mL) was then mixed with of the aqueous solution (0.8 mL) in a vibromixer (Capmix) for 15 s to form the oil-in-water emulsion. The emulsion was frozen in dry ice and methanol then dried at a pressure of 200 mTorr for 24 h to remove excess solvent. The powder was reconstituted as a suspension of hollow particles by addition of 1.0 mL water. The resulting ultrasound contrast agent was confirmed by microscopy observation, Coulter size distribution, acoustic attenuation and resistance to external pressure.

b) Synthesis of Biotin-D-Trp-Leu-Asp-Ile-Ile-Trp.OH (SEQ ID NO:6)

Described in example 5b).

c) Conjuaation of Polymer Particles Incorporating Avidin.

The particles from a) were centrifuged and the supernatant replaced with 1 mL of PBS buffer pH 7.5 containing 0.2 mg of biotin-GGCGCTGATGATGTTGTTGATTCTT (SEQ ID NO:10) and 0.2 mg of biotin-D-Trp-Leu-Asp-Ile-Ile-Trp.OH (SEQ ID NO:6) from b) above. After incubation for 24 h the particles were washed extensively with PBS and water.

EXAMPLE 12

Functionalisation of Gas-filled Albumin Microspheres (GAM) with Biotin for Multiple-specific Targeting a) Preparation of Biotinylated Albumin Microspheres A homogeneous suspension of GAM ($6 \times 10^8$ particles/mL) in 5 mg/mL albumin was used, with all manipulations being carried out at room temperature. Two 10 mL aliquots were centrifuged (170×g, 5 minutes) to promote floatation of the microspheres and 8 mL of the underlying infranatant was removed by careful suction and replaced by an equal volume of air-saturated phosphate buffered saline, the preparations being rotated for 15–20 minutes to resuspend the microspheres. This procedure was repeated twice, whereafter only negligible amounts of free non-microsphere-associated albumin were assumed to remain. 50 µl of NHS-biotin (10 mM in dimethylsulphoxide) was added to one of the aliquots (final concentration 50 µM); the other (control) aliquot received 50 µl of dimethylsulphoxide. The tubes containing the samples were rotated for 1 hour whereafter 20 µl portions of 50% aqueous glutaraldehyde were added to each tube to crosslink the microspheres. After rotation for another hour the tubes were positioned vertically overnight to allow floatation of the microspheres. The next day, the suspensions were washed twice with phosphate buffered saline containing 1 mg/mL human serum albumin (PBS/HSA) and were resuspended in PBS/HSA after the last centrifugation.

In order to determine the presence of microsphere-associated biotin, streptavidin conjugated to horseradish peroxidase (strep-HRP) was added to both suspensions and the tubes were rotated for 1 hour to allow for reaction. The microspheres were then washed three times, resuspended in 100 mM citrate-phosphate buffer (pH 5) containing 0.1 mg/mL phenylenediamine dihydrochloride and 0.01% hydrogen peroxide, and rotated for 10 minutes. Development of a yellow-green colour was indicative of the presence of enzyme. The following results were obtained:

| Sample | Colour development |
| --- | --- |
| Biotinylated spheres + strp-HRP | 2+ |
| Control spheres + strp-HRP | + |
| This confirms that GAM were biotinylated. | | b) Multiple-specific Gas-containing Microparticles

The biotinylated microspheres are then used to prepare multiple-specific targeting products in an analogous manner to those exemplified in examples 5), 6) and 7).

EXAMPLE 13

Multiple-specific Gas-containing Microbubbles of DSPS Functionalised with Heparin Sulphate Binding Peptide/Fibronectin Peptide/RGD Peptide and Fluorescein.

a) Synthesis of a Lipopeptide Containing the RGD Sequence and a Fluorescein Reporter Group: Dipalmitoyl-Lys-Lys-Lys-Lys[Acetyl-Ara-Gly-Asp-Lys (Fluorescein)] Gly.OH (SEQ ID NO:11)

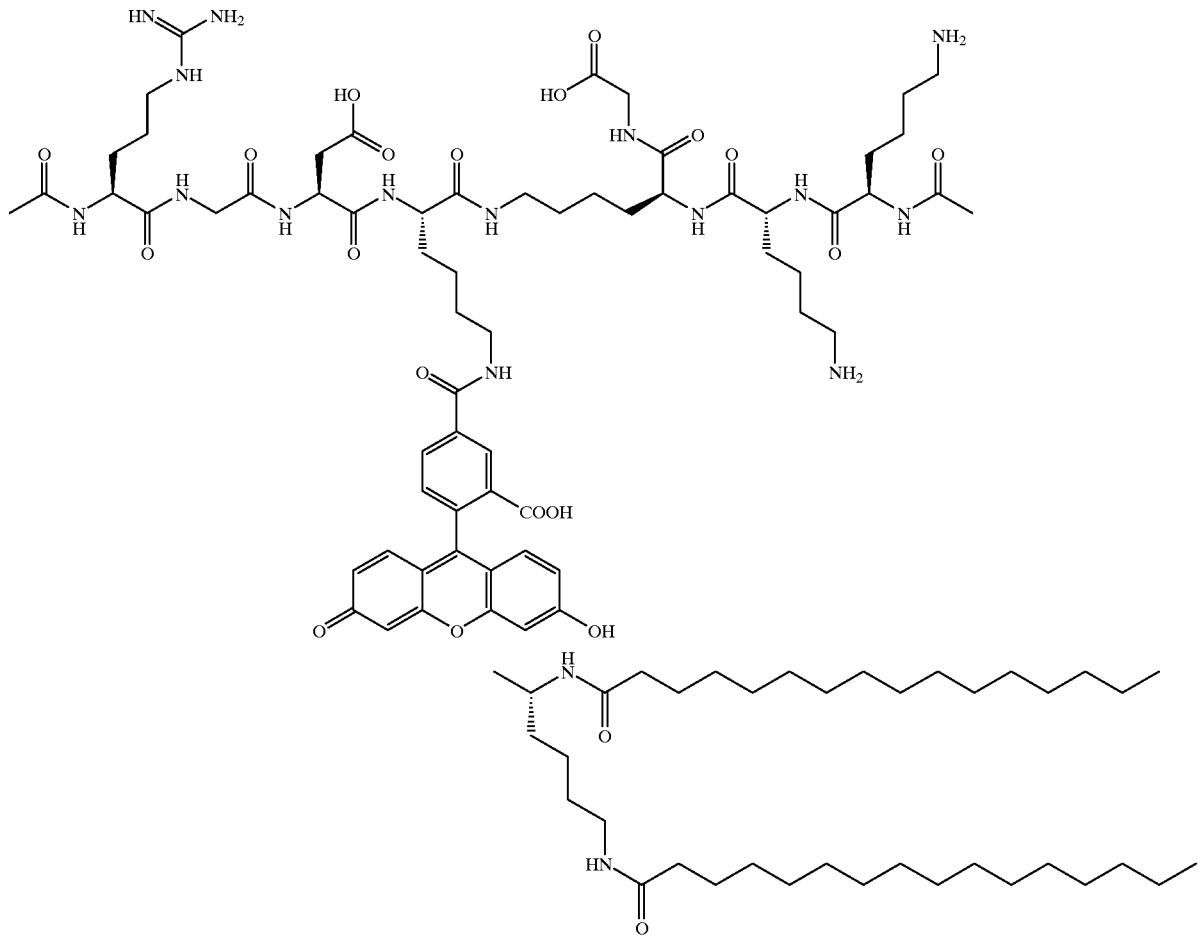

The lipopeptide was synthesised as described in example 1) using commercially available amino acids and polymers. The lipopeptide was cleaved from the resin in TFA containing 5% water, 5% phenol, 5% EDT for 2 h.

Following evaporation in vacuo the crude product was precipitated and triturated with diethyl ether. Purification by preparative HPLC (Vydac 218TP1022 column) of a 40 mg aliquot of crude material was carried out using a gradient of 60 to 100% B over 40 min (A=0.1% TFA/water and B=0.1% TFA/acetonitrile) at a flow rate of 9 mL/min. After lyophilization 10 mg of pure material (Analytical HPLC; Gradient, 60–100% B where B=0.1% TFA/acetonitrile), A=0.01% TFA/water: column–vydac 218TP54:Detection–UV 260–product retention time=20–22 min). Further product characterization was carried out using MALDI mass spectrometry; expected, M+H at 1922, found, at 1920.

b) Synthesis of a Lipopeptide Containing a Heparin Sulphate Binding Sequence and a Fibronectin Peptide Synthesis and purification described in example 1 a).

c) Preparation of Multiple-specific Gas-containing Microbubbles of DSPS Functionalised with a Heparin Sulphate Binding Peptide a Fibronectin Peptide Acetyl-RGD Peptide and Fluorescein.

DSPS (Avanti, 4 mg) and lipopeptide from a) (0.5 mg, 0.2 mmol) and lipopeptide from b) (0.5 mg) were weighed into each of 2 vials and 0.8 mL of a solution of 1.4% propylene glycol/2.4% glycerol was added to each vial. The mixture was warmed to 80° C. for 5 minutes (vials shaken during warming). The samples were cooled to room temperature and the head space flushed with perfluorobutane gas. The vials were shaken in a cap mixer for 45 s and the microbubbles formed rolled overnight. The microbubbles were washed several times with deionised water and analysed by MALDI mass spectrometry as described in example 1b). The microbubbles following analysis by microscopy were seen to consist of a range of sizes between 1 and 5 micron. Furthermore the microbubbles were fluorescent.

EXAMPLE 14

Multiple-specific Gas Containing Microbubbles of DSPS Covalently Modified with CD71 FITC-labelled Anti-transferrin Receptor Antibody and 'Doped' with a Lipopeptide with Affinity for Endothelial Cells.

This example is directed at the preparation of multiple vector targeted ultrasound agents.

a) Synthesis of an Endothelial Cell Binding Lipopeptide: 2-n-hexadecylstearyl-Lys-Leu-Ala-Leu-Lys-Leu-Ala-Leu-Lys-Ala-Leu-Lys-Ala-Ala-Leu-Lys-Leu-Ala-$NH_2$. (SEQ ID NO;12)

The lipopeptide shown below was synthesised on a ABI 433A automatic peptide synthesiser starting with a Rink amide resin on a 0.1 mmol scale using 1 mmol amino acid cartridges.

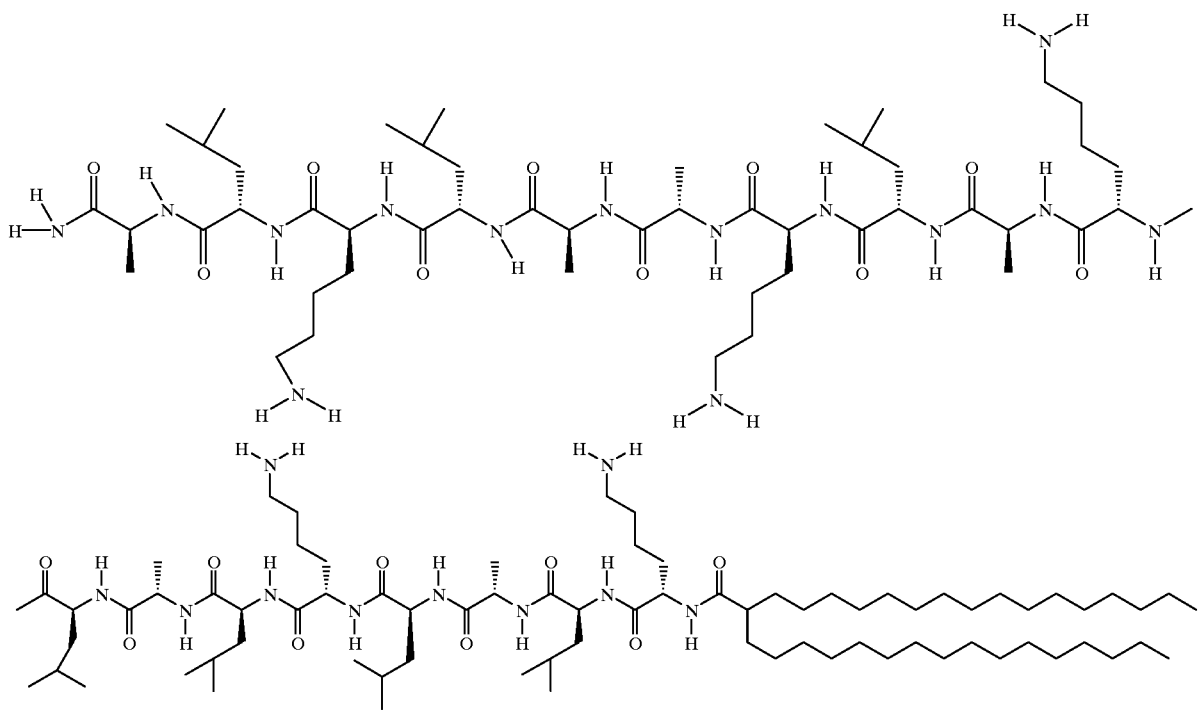
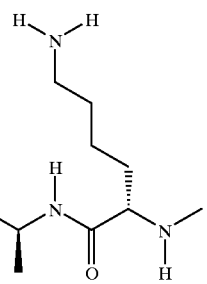

All amino acids and 2-n-hexadecylstearic acid were pre-activated using HBTU before coupling. The simultaneous removal of peptide from the resin and side-chain protecting groups was carried out in TFA containing 5% EDT, and 5% $H_2O$ for 2 hours giving a crude product yield of 150 mg. Purification by preparative HPLC (Vydac 218TP1022 column) of a 40 mg aliquot of crude material was carried out using a gradient of 90 to 100% B over 50 min (A=0.1% TFA/water and B=MeOH) at a flow rate of 9 mL/min. After lyophilization 10 mg of pure material was obtained (Analytical HPLC; Gradient, 90–100% B where B=MeOH, A=0.01% TFA/water: column–vydac 218TP54: Detection–UV 214 nm–product retention time=23 min). Further product characterization was carried out using MALDI mass spectrometry; expected, M+H at 2369, found, at 2373.

b) Preparation of Gas-containing Microbubbles of DSPS 'Doped' with a Endothelial Cell Binding Lipopeptide and PE-PEG$_{2000}$-MAL DSPS (Avanti, 4.5 mg) and lipopeptide from a) (0.5 mg) along with PE-PEG$_{2000}$-Maleimide from example 2 (0.5 mg) were weighed into a clean vial and 1 mL of a solution of 1.4% propylene glycol/2.4% glycerol added. The mixture was warmed to 80° C. for 5 minutes then filtered through a 4.5 micron filter. The sample was cooled to room temperature and the head space flushed with perfluorobutane gas. The vials were shaken in a cap mixer for 45 s and the microbubbles washed three times with distilled water.

c) Thiolation of FITC-labelled Anti-transferrin Receptor Antibody.

FITC labelled CD71 anti-transferrin receptor Ab (100 mg/mL, Becton Dickinson), 0.7 mL, in PBS was modified with Traut's reagent (0.9 mg, Pierce) at room temperature for 1 h. Excess reagent was separated from modified protein on a NAP-5 column (Pharmacia).

d) Conjugation of Thiolated FITC-labelled Anti-transferrin Receptor Antibody to Gas-containing Microbubbles of DSPS 'Doped' with an Endothelial Cell Binding Lipopeptide and DSPE-PEG$_{2000}$-MAL A 0.5 mL aliquot of the protein fraction (2 mL in total) from c) above was added to the microbubbles from b) and the conjugation reaction allowed to proceed for 10 min on a roller table. Following centrifugation at 1000 rpm for 3 min the protein solution was removed and the conjugation repeated a further two times with 1 mL and 0.5 mL aliquots of protein solution respectively. The bubbles were then washed four times in distilled water and a sample analysed for the presence of antibody by flow cytometry and microscopy. A fluorescent population of >92% was observed. (See FIG. 1).

Incorporation into the microbubbles of lipopeptide was confirmed by MALDI mass spectrometry as described in Example 1b).

EXAMPLE 15

Preparation of Multiple-sepecific Transferrin/Avidin Coated gas-filled Microbubbles for Targeted Ultrasound Imaging.

This example is directed to the preparation of microbubbles containing multiple protein vectors for targeted ultrasound/therapy.

a) Synthesis of a Thiol Functionalised Lipid Molecule: Dipalmitoyl-Lys-Lys-Lys-Aca-Cys.OH (SEQ ID NO:13)

(SEQ ID NO: 13)

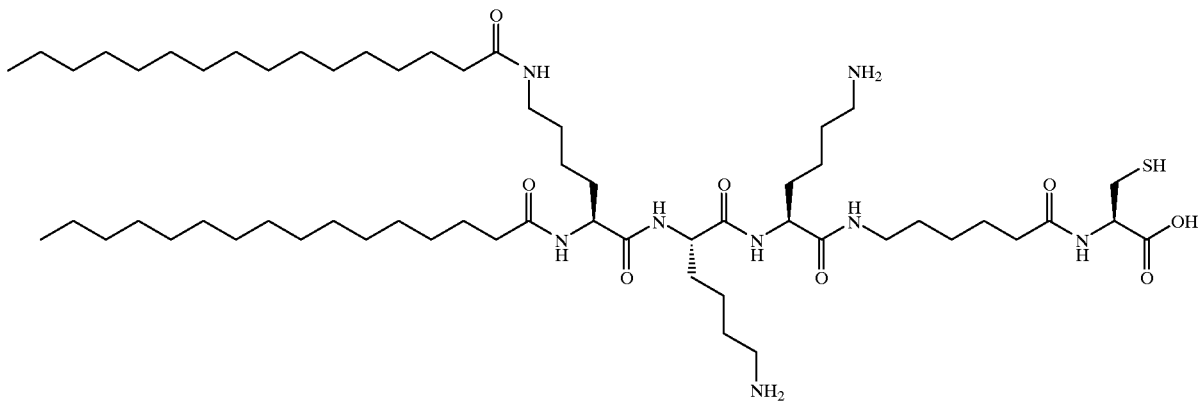

The lipid structure shown above was synthesised on a ABI 433A automatic peptide synthesiser starting with Fmoc-Cys (Trt)-Wang resin (Novabiochem) on a 0.25 mmol scale using 1 mmol amino acid cartridges. All amino acids and palmitic acid were preactivated using HBTU coupling chemistry.

The simultaneous removal of peptide from the resin and deprotection of side-chain protecting groups was carried out in TFA containing 5% EDT, and 5% H$_2$O for 2 hours giving a crude product yield of 250 mg. Purification by preparative HPLC (Vydac 218TP1022 column) of a 40 mg aliquot of crude material was carried out using a gradient of 90 to 100% B over 50 min (A=0.1% TFA/water and B=MeOH) at a flow rate of 9 mL/min. After lyophilization 24 mg of pure material was obtained (Analytical HPLC; Gradient, 70–100% B where B=0.1% TFA/ acetonitrile, A=0.01% TFA/water: column–vydac 218TP54: Detection–UV 214 nm-product retention time=23 min). Further product characterization was carried out using MALDI mass spectrometry; expected, M+H at 1096, found, at 1099.

b) Preparation of Gas-containing Microbubbles of DSPS 'Doped' with a Thiol Containing Lipid Structure:

DSPS (Avanti, 4.5 mg) and the lipid structure from a) above (0.5 mg) were weighed into a clean vial and 0.8 mL of a solution containing 1.4% propylene glycol/ 2.4% glycerol in water added. The mixture was warmed to 80° C. for 5 minutes (vials shaken during warming) and filtered while still hot through a 40 micron filter. The samples were cooled to room temperature and the head space flushed with perfluorobutane gas. The vials were shaken in a cap mixer for 45 s and the microbubbles placed on roller table overnight. Bubbles were washed several times with deionised water and analysed for thiol group incorporation using Ellmans Reagent.

c) Modification of Transferrin and Avidin with Fluorescein-NHS and Sulpho-SMPB.

To a mixture of 2 mg of transferrin (Holo, human, Alpha Therapeutic Corp) and 2 mg of avidin (Sigma) in PBS (1 mL) was added 0.5 mL DMSO solution containing 1 mg Sulpho-SMPB (Pierce) and 0.5 mg Fluorescein-NHS (Pierce). The mixture was stirred for 45 minutes at room temperature then passed through a Sephadex 200 column using PBS as eluent. The protein fraction was collected and stored at 4° C. prior to use.

d) Microbubble Conjugation with Modified Transferrin/Avidin.

To the thiol containing microbubbles from b) was added 1 mL of the modified transferrin/avidin protein solution c). After adjusting the pH of the solution to 9 the conjugation reaction was allowed to proceed for 2 h at room temperature. Following extensive washing with deionised water the microbubbles were analysed by Coulter counter (81% between 1 and 7 micron) and fluorescence microscopy (highly fluorescent microbubbles were observed).

EXAMPLE 16

Preparation of Functionalised Gas-filled Microbubbles for Taraeted Ultrasound Imaging.

This example is directed to the preparation of microbubbles having a reactive group on the surface for non-specific targeting, principally utilising disulphide exchange reactions to effect binding to a multiplicity of cellular targets.

DSPS (Avanti, 5.0 mg) and the thiol containing lipid structure from example 15a)(1.0 mg) were weighed into a clean vial and 0.8 mL of a solution containing 1.4% propylene glycol/ 2.4% glycerol in water added. The mixture was warmed to 80° C. for 5 minutes (vials shaken during warming) and filtered while still hot through a 40 micron filter. The samples were cooled to room temperature and the head space flushed with perfluorobutane gas. The vials were shaken in a cap mixer for 45 s and the microbubbles placed on roller table overnight. Bubbles were washed several times with deionised water and analysed for thiol group incorporation using Ellmans Reagent.

EXAMPLE 17

Multiple-specific Gas-containing Microbubbles of DSPS Comprising a Lipopeptide for Endothelial Cell Targeting and a Captopril Containing Molecule.

This example is directed to the preparation of ultrasound agents for combined targeting and therapeutic applications.

a) Synthesis of a Lipopeptide Functionalised with Captopril: (SEQ ID NO:14)

(SEQ ID NO: 14)

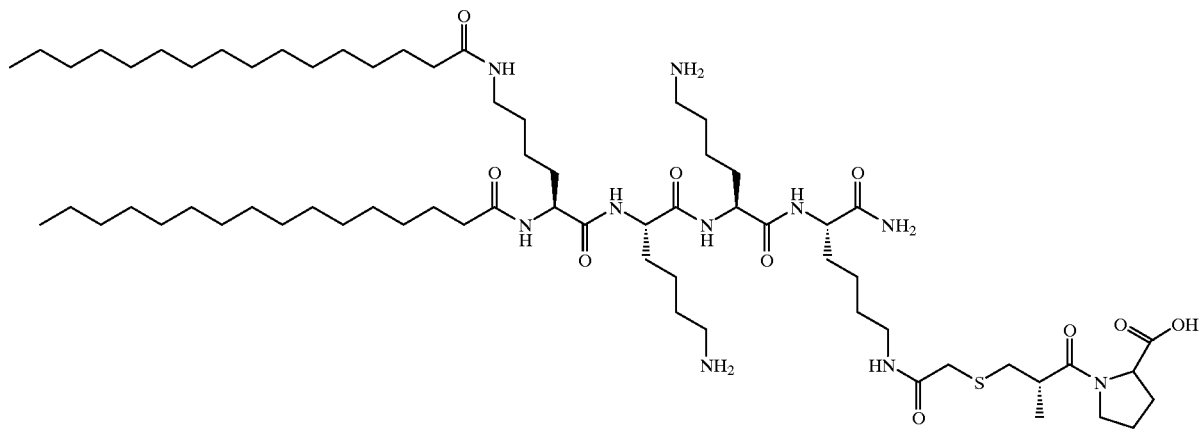

The structure shown above was synthesised using a manual nitrogen bubbler apparatus starting with Fmoc protected Rink Amide MBHA resin (Novabiochem) on a 0.125 mmol scale. All amino acids were purchased from Novabiochem and palmitic acid from Fluka. Coupling was carried out using standard TBTU/HOBt/DIEA protocols. Bromoacetic acid was coupled through the side-chain of Lys as a symmetrical anhydride using DIC preactivation. Captopril (Sigma) dissolved in DMF was introduced on the solid-phase using DBU as base.

Simultaneous removal of the peptide from the resin and deprotection of side-chain protecting groups was carried out in TFA containing 5% EDT, 5% water and 5% ethyl methyl sulphide for 2 h. An aliquot of 10 mg of the crude material was purified by preparative liquid chromatography (Vydac 218TP1022 column) using a gradient of 70 to 100% B over 60 min (A=0.1% TFA/water and B=0.1% TFA/acetonitrile) at a flow rate of 10 mL/min. After lyophilization a yield of 2 mg of pure material was obtained (analytical HPLC: gradient 70–100% B over 20 min, A=0.1% TFA/water and B=0.1% TFA/acetonitrile; flow rate 1 mL/min; column Vydac 218TP54; detection UV 214 nm; retention time 26 min). Further characterisation was carried out using MALDI mass spectrometry, giving M+H at 1265 as expected.

b) Synthesis of a Lipopeptide with Affinity for Endothelial Cells: Dipalmitoyl-Lys-Lys-Lys-Aca-Ile-Ara-Arg-Val-Ala-Ara-Pro-Pro-Leu-NH$_2$ (SEQ ID NO:15)

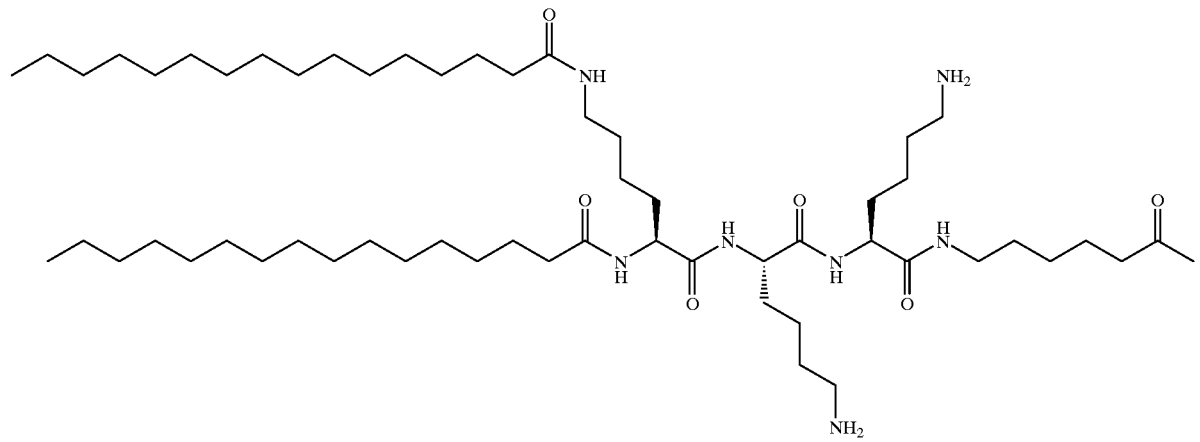

-continued

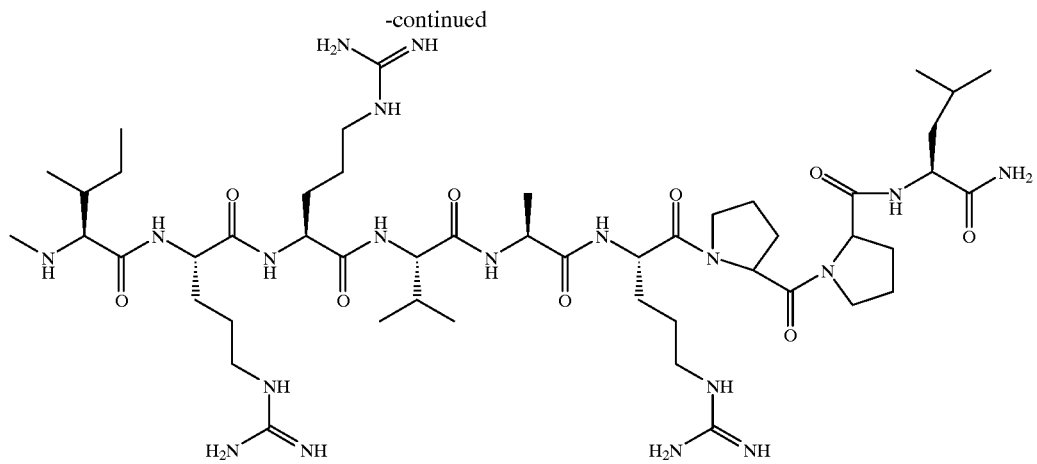

The lipopeptide was synthesised on a ABI 433A automatic peptide synthesiser starting with Rink amide resin (Novabiochem) on a 0.1 mmol scale using 1 mmol amino acid cartridges. All amino acids and palmitic acid were preactivated using HBTU before coupling. The simultaneous removal of peptide from the resin and side-chain protecting groups was carried out in TFA containing 5% phenol, 5% EDT and 5% $H_2O$ for 2 hours giving a crude product yield of 160 mg. Purification by preparative HPLC (Vydac 218TP1022 column) of a 35 mg aliquot of crude material was carried out using a gradient of 70 to 100% B over 40 min (A=0.1% TFA/water and B=MeOH) at a flow rate of 9 mL/min. After lyophilization 20 mg of pure material was obtained (Analytical HPLC; Gradient, 70–100% B where B=MeOH, A=0.01% TFA/water: column–vydac 218TP54: Detection–UV 214 and 260 nm–product retention time=16 min). Further product characterization was carried out using MALDI mass spectrometry; expected, M+H at 2050, found, at 2055.

c) Preparation of Gas-containing Microbubbles of DSPS Comprising a Lipopeptide for Endothelial Cell Targeting and a Captopril Containing Molecule for Drug Delivery DSPS (Avanti, 4.5 mg), product from a) (0.5 mg) and product from b) (0.5 mg) were weighed into a vial and 1.0 mL of a solution of 1.4% propylene glycol/ 2.4% glycerol was added to each vial. The mixture was warmed to 80° C. for 5 minutes (vials shaken during warming). The samples were cooled to room temperature and the head space flushed with perfluorobutane gas. The vials were firstly shaken in a cap mixer for 45 s then rolled for 1 h followed by extensive washing with deionised water. No detectable levels of starting material were found in the final wash solution as evidenced by MALDI MS. MALDI mass spectral analysis was used to confirm incorporation of the products from section a) and b) into the microbubbles as described in example 1b).

d) In Vitro Study of Gas-containing Microbubbles of DSPS Comprising a Lipopepitde for Endothelial Cell Targeting and a Captopril Containing Molecule for Therapeutic Applications.

The in vitro assay described in example 1c) was used to examine cell binding under flow conditions. A gradual accumulation of the microbubbles on the cells took place which was dependant on the flow rate. By increasing the flow rate the cells started to become detached from the coverslip, the microbubbles were still bound to the cells. Control bubbles not carrying the vector did not adhere to the endothelial cells and disappeared from the cells under minimal flow conditions.

EXAMPLE 18

Preparation of Multiple-specific Gas-containing Microbubbles of DSPS loaded with a Lipopeptide Comprising a Helical Peptide with Affinity for Cell Membranes and the Peptide Antibiotic Polymixin B Sulphate.

This example is directed at the preparation of targeted microbubbles comprising multiple peptidic vectors having a combined targeting and a therapeutic application.

a) Synthesis of a Lipopeptide Comprising a Helical Peptide with Affinity for Cell Membranes:hexadecylstearyl-Lys-Leu-Ala-Leu-Lys-Leu-Ala-Leu-Lys-Ala-Leu-Lys-Ala-Ala-Leu-Lys-Leu-Ala-$NH_2$ (SEQ ID NO:12).

Described in example 14a).

b)—Preparation of Multiple-specific Gas-containing Microbubbles.

DSPS (Avanti, 5.0 mg), lipopeptide from a)(0.3 mg)and polymixin B sulphate (Sigma,0.5 mg) were weighed into a clean vial and 1.0 mL of a solution of 1.4% propylene glycol/ 2.4% glycerol added. The mixture was sonicated for 3–5 mins, warmed to 80° C. for 5 minutes then filtered through a 4.5 micron filter. The mixture was cooled to room temperature and the head space flushed with perfluorobutane gas. The vial was shaken in a cap mixer for 45 s and the microbubbles centrifuged at 1000 rpm for 3 minutes. The microbubbles were washed in water until no polymixin B sulphate or lipopeptide could be detected in the infranatant by MALDI-MS. Microscopy showed that the size distribution of the bubble population was between 1–8 micron as desired. To the washed bubbles (ca. 0.2 mL) was added methanol (0.5 mL) and the mixture placed in a sonic bath for 2 min. The resulting clear solution, following analysis by MALDI-MS, was found to contain both lipopeptide and polymixin B sulphate (expected 1203, found 1207).

EXAMPLE 19

Preparation of Multiple-specific Gas-containing Microbubbles of DSPS 'Doped' with a Lipopeptide Comprising a IL-1 Receptor Binding Sequence and Modified with a Branched Structure Containing the Drug Methotrexate.

This example is directed at the preparation of targeted microbubbles comprising multiple vectors for targeted/ therapeutic /drug release applications.

Synthesis of a Lipopeptide Comprising an Interleukin-1 Receptor Binding Peptide: Dipalmitoyl-Lys-Gly-Asp-Trp-Asp-Gln-Phe-Gly-Leu-Trp-Ara-Gly-Ala-Ala.OH (SEQ ID NO:16)

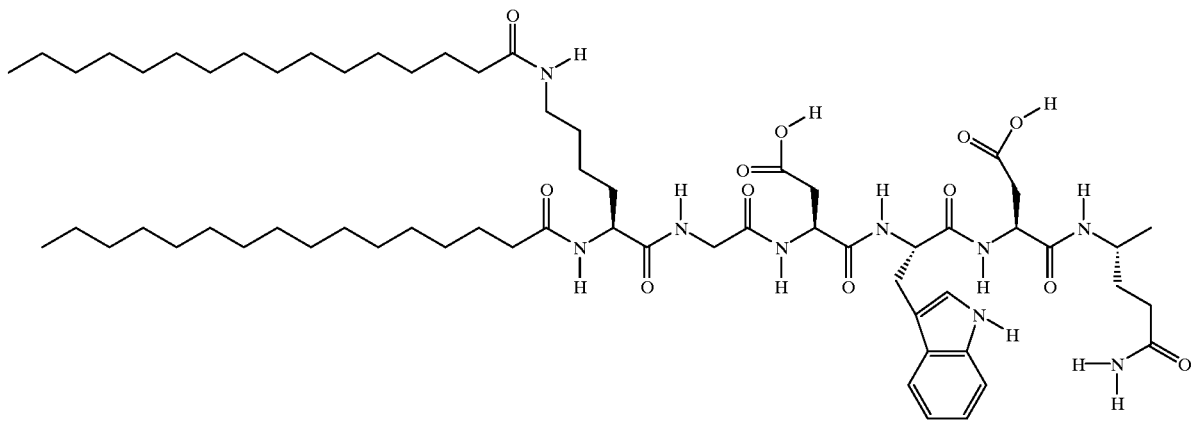

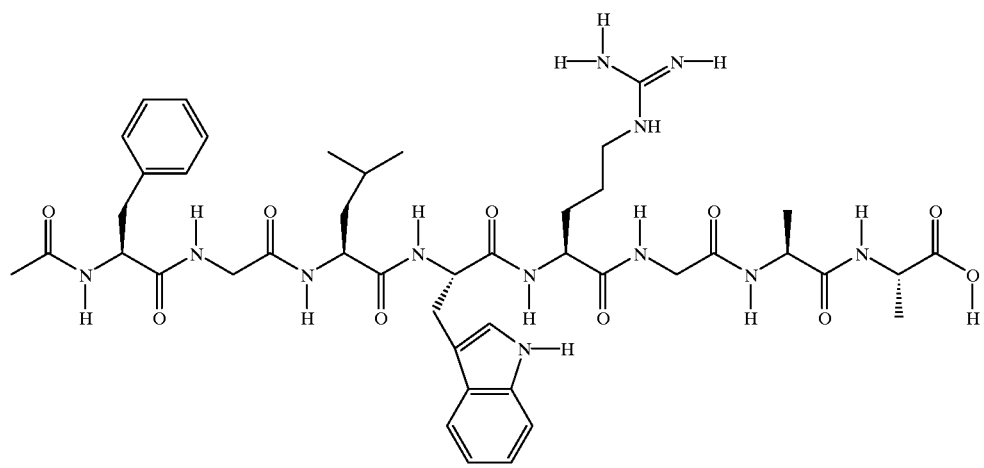

The lipopeptide was synthesised on a ABI 433A automatic peptide synthesiser starting with Fmoc-Ala-Wang resin (Novabiochem) on a 0.1 mmol scale using 1 mmol amino acid cartridges. All amino acids and palmitic acid were preactivated using HBTU before coupling. The simultaneous removal of lipopeptide from the resin and side-chain protecting groups was carried out in TFA containing 5% $H_2O$, 5% anisole, 5% phenol and 5% EDT for 2 hours giving a crude product yield of 150 mg. Purification by preparative HPLC (Vydac 218TP1022 column) of a 30 mg aliquot of crude material was carried out using a gradient of 90 to 100% B over 40 min (A=0.1% TFA/water and B=MeOH) at a flow rate of 9 mL/min. After lyophilization 4 mg of pure material was obtained (Analytical HPLC; Gradient, 90–100% B over 20 min where B=MeOH, A=0.01% TFA/water: column–vydac 218TP54: Detection–UV 214 nm; product retention time 23 min). Further product characterization was carried out using MALDI mass spectrometry; expected, M+H at 2083, found, at 2088.

b) Synthesis of a Branched Methotrexate Core Structure Containing a Thiol Moiety.

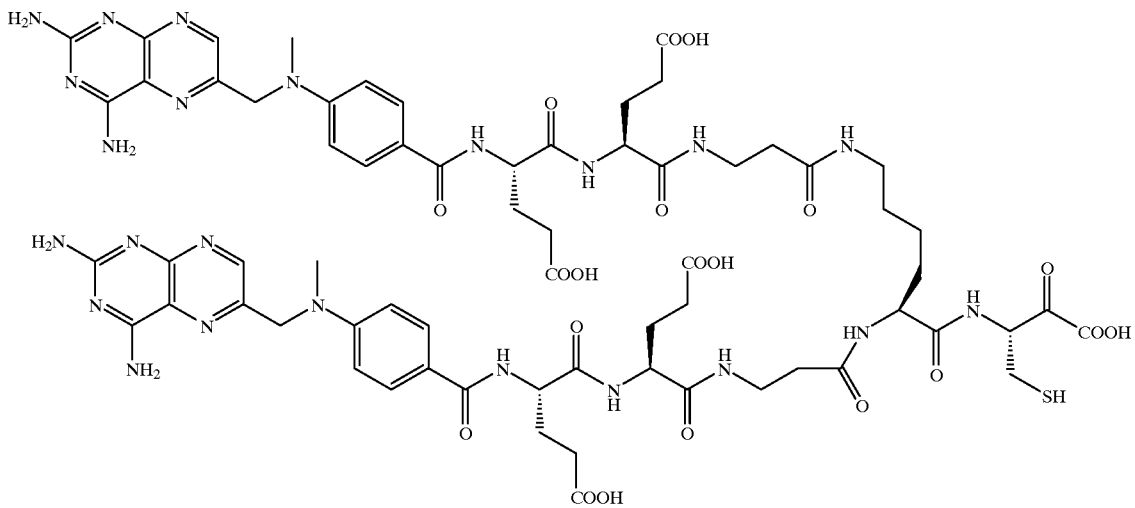

The methotrexate structure was synthesised on a ABI 433A automatic peptide synthesiser starting with Fmoc-Cys (Trt) Tentagel resin on a 0.1 mmol scale. The simultaneous removal of product from the resin and deprotection of protecting groups was carried out in TFA containing 5% EDT and 5% H$_2$O for 2 hours giving a crude product yield of 160 mg. Purification by preparative HPLC (Vydac 218TP1022 column) of a 30 mg aliquot of crude material was carried out using a gradient of 10 to 30% B over 40 mm (A 0.1% TeA/water and B=0.1% TCA/acetonitrile) and a flow rate of 9 mL/min. After lyophilization of the pure fractions 9 mg of pure material was obtained (Analytical HPLC; Gradient, 5–50% B where B=0.1% TFA/acetonitrile, A=0.01% TFA/water: column–vydac 218TP54: Detection–UV 214 nm–product retention time=9.5 min). Further product characterization was carried out using MALDI mass spectrometry; expected, M+H at 1523, found, 1523.

c)—Preparation of Multiple-specific Gas-containing Microbubbles.

DSPS (Avanti, 4.5 mg) and thiol containing lipopeptide from example 15a) (0.5 mg) and lipopeptide from a) (0.2 mg) above were weighed into a clean vial and 1.0 mL of a solution of 1.4% propylene glycol/ 2.4% glycerol added. The mixture was sonicated for 3–5 mins, warmed to 80° C. for 5 minutes then filtered through a 4.5 micron filter. The mixture was cooled to room temperature and the head space flushed with perfluorobutane gas. The vials were shaken in a cap mixer for 45 s and the microbubbles centrifuged at 1000 rpm for 3 minutes following which the infranatant was discarded.

d) Conjugation of Methotrexate Branched Structure to Thiolated Microbubbles.

The methotrexate structure from b) above (0.5 mg) was dissolved in PBS pH 8.0. The solution was then added to the thiol containing bubbles from c) and disulphide bond formation allowed to proceed for 16 h. Following extensive washing with PBS and water the bubbles were analysed by microscopy and MALDI MS.

It is also considered relevant that the disulphide bond linking the methotrexate structure to the microbubble may be reduced in vivo liberating the free drug molecule. This in combination with a tumour specific vector is a drug delivery system. A physiologically relevant reducing agent such as glutathione may be used to bring about drug release.

EXAMPLE 20

Preparation of Microbubbles Coated with Poly-L-lysine Complexed to Fluorescein Labeled DNA Fragments from Plasmid pBR322

This example is directed to the preparation of microbubbles for gene therapy/anti-sense applications. It is envisaged that specific targeting may be achieved by further doping of microbubble membranes with vector modified lipid structures as described in example 1.

a) Preparation of DSPS Gas-containing Microbubbles

DSPS (Avanti, 4.5 mg) was weighed into a clean vial. 1.0 mL of a solution of 1.4% propylene glycol/ 2.4% glycerol was added and the mixture sonicated for 2 min then warmed to 80° C. for 5 minutes. Immediately following warming the solution was filtered through a 4 micron filter. The sample was cooled to room temperature and the head space flushed with perfluorobutane gas. The vial was shaken in a cap mixer for 45 s. Bubbles were then washed once with deionised water and the infranatant discarded. The microbubbles were then resuspended in 0.5 mL water.

b) Preparation of Poly-L-lysine/DNA Complex and Loading of DSPS Microbubbles

To 1 mg of poly-L-lysine (70–150 kD) in a clean vial was added 0.1 mL of a fluorescein labeled digest of plasmid pBR322 (Biorad) dissolved in TE buffer (10 mM tris-HCl, pH 8). The solution was made up to a total of 0.6 mL by addition of water and the pH adjusted to 8. Complexation was allowed to proceed for 1 h then 0.05 mL of the polylysine-DNA solution was added to the microbubble suspension from a) above. After 1 h microscopy was used to show that the bubbles were fluorescent confirming the presence of DNA.

EXAMPLE 21

Preparation of Multiple-specific Gas-filled Microbubbles Containing a Branched Core Peptide Comprising a Dabsylated-atherosclerotic Plaque Binding Sequence and RGDS (SEQ ID NO:21).

This example is directed to the preparation of microbubbles having a thiol group on the surface for modification with thiol containing vectors for targeting/drug delivery and drug release.

a) Synthesis of the Branched Peptide Dabsyl-Tyr-Arg-Ala-Leu-Val-Asp-Thr-leu-Lys-Lys(NH2-Ara-Gly-Asp-Ser)-Gly-Cys.OH (SEQ ID NO:17)

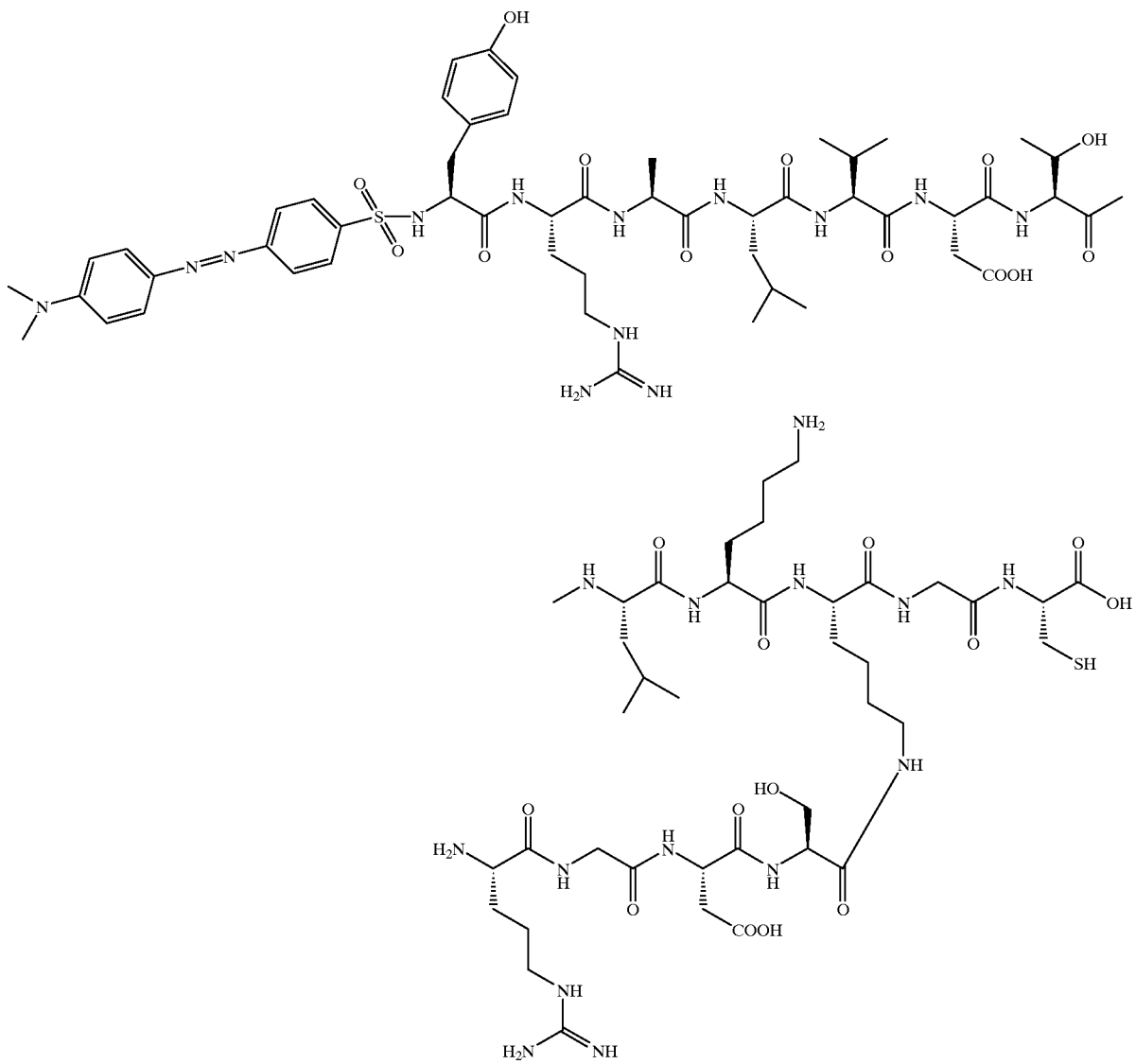

The peptide was synthesised on a ABI 433A automatic peptide synthesiser starting with Fmoc-Cys(Trt)-Tentagel resin on a 0.1 mmol scale using 1 mmol amino acid cartridges. All amino acids were preactivated using HBTU before coupling. The simultaneous removal of peptide from the resin and side-chain protecting groups was carried out in TFA containing 5% phenol , 5% EDT and 5% $H_2O$ for 2 hours giving a crude product yield of 160 mg. Purification by preparative HPLC (Vydac 218TP1022 column) of a 30 mg aliquot of crude material was carried out using a gradient of 10 to 60% B over 40 min (where A=0.1% TFA/water and B=acetonitrile) at a flow rate of 9 mL/min. After lyophilization 2.5 mg of pure material was obtained (Analytical HPLC; Gradient, 10–50% B over 20 min where B=0.1% TFA/acetonitrile and A=0.01% TFA/water: column–vydac 218TP54: Detection–UV 214 and 435 nm–product retention time=21 min). Further product characterization was carried out using MALDI mass spectrometry; expected, M+H at 2070, found, at 2073.

b) Preparation of Thiol Containing Gas-filled Microbubbles.
As described in example 15a) and b).

c) Oxidative Coupling of Thiolated Microbubbles with Multiple-specific Peptide via Disulphide Bond Formation.

The infranatant from the microbubbles from b) above was discarded and replaced with a solution of dabsyl-peptide from a) (1 mg) in 0.7 mL dil. ammonia solution (pH 8). To this was added 0.2 mL of a stock solution containing 6 mg of potassiumferricyanate dissolved in 2 mL of water. The vial was placed on a roller table and thiol oxidation allowed to proceed for 2 h. The bubbles were then washed extensively with water until the infranatant was free of the dabsyl-peptide as evidenced by hplc and MALDI MS.

Detection of microbubble bound peptide was carried out by reduction of the disulphide bond using the water souble reducing agent tris-(2-carboxyethyl)-phosphine. Following reduction the infranatant was found to contain free dabsyl-peptide as evidenced by hplc and MALDI MS.

Other physiological relevant reducing agents such as reduced glutathione are also considered useful for initiating release.

EXAMPLE 22

Gas-containing Microparticles Comprising Polymer from Ethylidene Bis(16-hydroxyhexadecanoate) and Adipoyl Chloride and Biotin-amidocaproate-Ala Covalently attached to the Polymer a) Synthesis of Z-Ala-polymer (3-O-(carbobenzyloxy-L-alanyl)-polymer)

The polymer is prepared from ethylidene bis(16-hydroxyhexadecanoate) and adipoyl chloride as described in WO-A-9607434, and a polymer fraction with molecular weight 10000 is purified using gel permeation chromatography (GPC). 10 g of the material (corresponding to 1 mmol OH groups), Z-alanine (5 mmol) and dimethylaminopyridine (4 mmol) are dissolved in dry dimethylformamide/tetrahydrofuran and dicyclohexylcarbodiimide is then added. The reaction mixture is stirred at ambient temperature overnight. Dicyclohexylurea is filtered off and the solvent is removed using rotary evaporation. The product is purified by chromatography, fractions containing the title compound are combined and the solvent is removed using rotary evaporation. The structure of the product is confirmed by NMR.

b) Synthesis of Ala-polymer (3-O-(L-alanyl)-polymer)

Z-Ala-polymer (0.1 mmol) is stirred in toluene/tetrahydrofuran and glacial acetic acid (15% of the total volume) and hydrogenated in the presence of 5% palladium on charcoal for 2 hours. The reaction mixture is filtered and concentrated in vacuo.

c) Synthesis of Biotinamidocaproate-Ala-polymer

A solution of biotinamidocaproate N-hydroxysuccinimide ester in tetrahydrofuran is added to $H_2N$-Ala-polymer dissolved in a mixture of tetrahydrofuran and dimethylformamide and 0.1 M sodium phosphate buffer having a pH of 7.5. The reaction mixture is heated to 30° C. and stirred vigorously; the reaction is followed by TLC to completion. The solvent is evaporated and the crude product is used without further purification.

d) Gas-containing Particles Comprising Biotin-amidocaproate-Ala-polymer and PEG 10000 Methyl Ether 16-hexadecanoyloxyhexadecanoate 10 mL of a 5% w/w solution of biotin-amidocaproate-Ala-polymer in (−)-camphene maintained at 60° C. is added to 30 mL of an 1% w/w aqueous solution of PEG 10000 methyl ether 16-hexadecanoyloxyhexadecanoate (prepared as described in WO-A-9607434) at the same temperature. The mixture is emulsified using a rotor stator mixer (Ultra Turax® T25) at a slow speed for several minutes, and thereafter is frozen in a dry ice/methanol bath and lyophilized for 48 hours, giving the title product as a white powder.

e) Acoustic Characterisation and Microscopy of the Product

Confirmation of the microparticulate nature of the product is performed using light microscopy as described in WO-A-9607434. Ultrasonic transmission measurements using a 3.5 MHz broadband transducer indicate that a particle suspension of <2 mg/mL gives a sound beam attenuation of at least 5 dB/cm.

f) Multiple-specific Microparticles

The biotinylated microspheres are then used to prepare multiple-specific targeting products similar to those exemplified in examples 5), 6) and 7).

EXAMPLE 23

Preparation of Multiple-specific Gas-containing Microbubbles Encapsulated with DSPS and Biotin-$PEG_{3400}$-acyl-phosphatidylethanolamine and Functionalised with Streptavidin, Oligonucleotide Biotin-GAAAGGTAGTGGGGTCGTGTGCCGG (SEQ ID NO:9) and Biotinylated Fibrin-anti-polymerant Peptide (Biotin-GPRPPERHOS.$NH_2$) (SEQ ID NO:7).

a) Synthesis of Biotin-$PEG_{3400}$-acyl-phosphatidyl Ethanolamine

A mixture of dipalmitoyl phosphatidyl ethanolamine, (21.00 mg, 0.03 mmol), biotin-PEG-$CO_2$-NHS, (100 mg, 0.03 mmol) and triethylamine (42 µl, 0.30 mmol) in a solution of chloroform/methanol (3:1) was stirred at room temperature for 2 hours. After evaporation of the solvents under reduced pressure, the residue was flash chromatographed (methylene chloride/methanol/water, 40:8:1). The product was obtained as a yellow gum, 112 mg (94%) and structure verified by NMR and MALDI-MS.

b) Binding of Fluorescein-conjugated Streptavidin to Gas Filled Microbubbles

Gas-containing microbubbles were prepared by mixing DSPS and biotin-$PEG_{3400}$-acyl-phosphatidyl ethanolamine as described in example 5a).

The microbubble suspension was divided into 0.2 mL aliquots and fluorescein conjugated streptavidin added as shown in the table below. The samples were incubated on a roller table for 15 or 30 minutes at ambient temperature before removal of excess protein by washing in PBS.

Results:

| Aliquot no. | Added Streptavidin (µg/200:1 sample) | Incubation time (amb. temp.) | % Fluorescent particles | Particle median diameter (microns) |
|---|---|---|---|---|
| 1 | 0 | | 2.0 | — |
| 2 | 0 | | — | 12 (foam) |
| 3 | 0.2 ($3 \times 10^{-9}$ mmol) | 30 min | 7.8 | 3.9 |
| 4 | 2 ($3 \times 10^{-8}$ mmol) | 30 min | 26.2 | 4.2 |
| 5 | 10 ($1.5 \times 10^{-7}$ mmol) | 15 min | 30.5 | na |
| 6 | 20 ($3 \times 10^{-7}$ mmol) | 30 min | 97.9 | 5.2 |
| 7 | 40 ($6 \times 10^{-7}$ mmol) | 15 min | 96.7 | 5.1 |
| 8 DSPS control | 20 ($3 \times 10^{-7}$ mmol) | 15 min | 0.6 | 3.7 |

The samples were analysed by flow cytometry and Coulter Counter. The results are summarized in the table above.

c) Conjugation of Streptavin Coated Microbubbles with the Oligonucleotide Biotin-GAAAGGTAGTGGGGTCGTGTGCCGG (SEQ ID NO:9) and Biotinylated Fibrin-anti-polymerant Peptide Biotin-GPRPPERHOS (SEQ ID NO:7)

The particles from aliquot no. 6 above were centrifuged and the supernatant replaced with 1 mL of PBS buffer pH 7.5 containing 0.2 mg of biotin-GAAAGGTAGTGGGGTCGTGTGCCGG (SEQ ID NO:9) and 0.2 mg of biotin-GPRPPERHQS (SEQ ID NO:7) (Example 5c). After incubation for 24 h the particles were washed extensively with PBS and water.

It is envisaged that other biotinylated vectors or therapeutic agents may be conjugated to streptavidin or avidin coated microbubbles using this procedure.

EXAMPLE 24

Preparation of Microbubbles Encapsulated with DSPS and Functionalised with a Thrombi-taraeting Lipopeptide and the Thrombolytic Enzyme Tissue Plasminogen Activator. This example is directed at the preparation of thrombus targeted US agents comprising a therapeutic thromolytic agent. a) Synthesis of a lipopeptide with affinity for thrombi (Dipalmitoyl-Lys-Asn-Asp-Gly-Asp-Phe-Glu-Glu-Ile-Pro-Glu-Glu-Tyr-Leu-Gln.NH$_2$) (SEQ ID NO:18)

min then purification carried out on a Superdex 200 column. The product was eluted in PBS and the modified protein fraction collected.

c) Preparation of Microbubbles Encapsulated with DSPS/ thrombi-binding Lipopeptide and Thiol Containing Lipoeptide and Conjugation to Modified Tissue Plasminogen Activator.

DSPS (Avanti, 5.0 mg) was weighed into a clean vial along with 0.5 mg of the lipopeptide from a) and 0.5 mg of the thiol containing lipopeptide from example 15a).

To this was added 1.0 mL of a solution of 1.4% propylene glycol/ 2.4% glycerol and the mixture sonicated for 2 min (SEQ ID NO: 18)

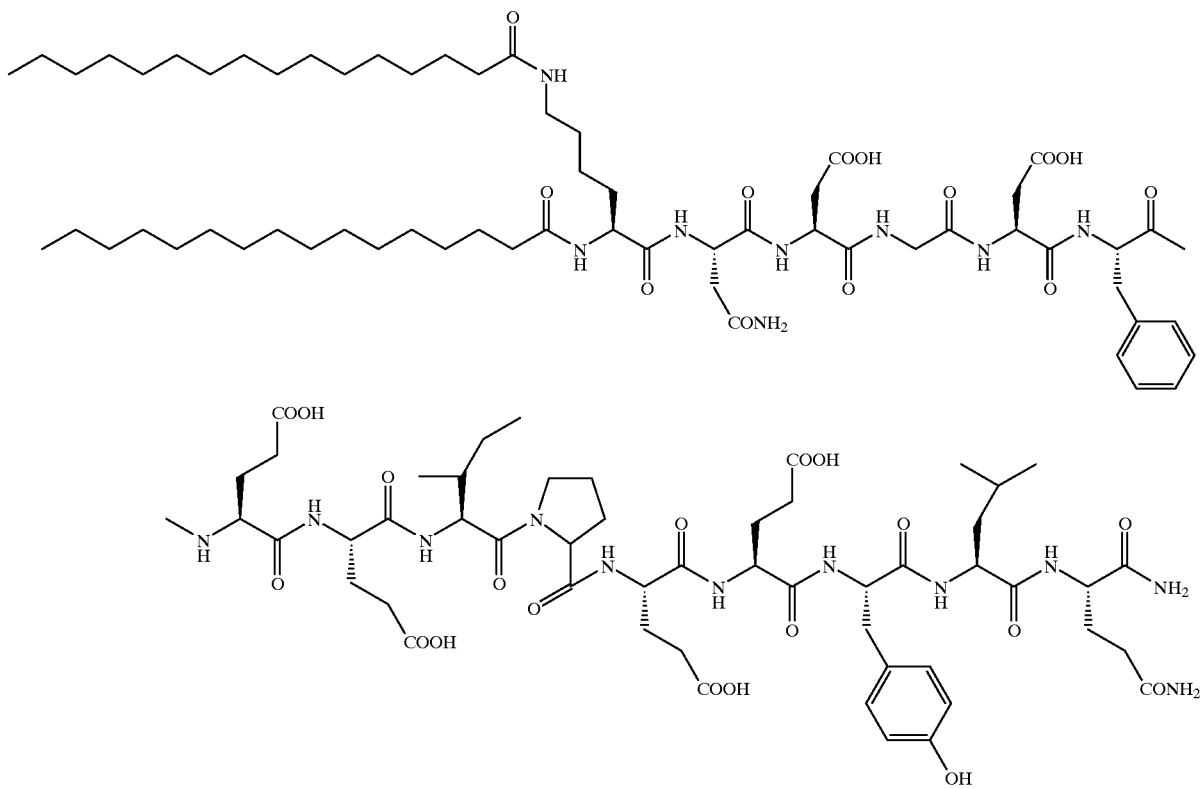

The lipopeptide was synthesised on a ABI 433 A automatic peptide synthesiser starting with Rink amide resin (Novabiochem) on a 0.1 mmol scale using 1 mmol amino acid cartridges. All amino acids and palmitic acid were preactivated using HBTU before coupling. The simultaneous removal of peptide from the resin and side-chain protecting groups was carried out in TFA containing 5% phenol, 5% EDT, 5% anisole and 5% H$_2$O for 2 h giving a crude product yield of 80 mg. Purification by preparative HPLC (Vydac 218TP1022 column) of a 20 mg aliquot of the crude material was carried out. After lyophilization 6 mg of pure material was obtained. The product was characterized by MALDI mass spectrometry and analytical HPLC.

b) Modification of Issue Plasminogen Activator with Sulpho-SMPB.

A solution of 0.1 mL of ammonium carbonate buffer containing 0.1 mg of t-PA (Sigma) was made up to 0.2 mL by the addition of water. To this solution was added 0.4 mg of Sulpho-SMPB (Pierce) dissolved in 0.05 mL DMSO. The protein solution was left standing at room temperature for 45 then warmed to 80° C. for 5 minutes. Immediately following warming the solution was filtered through a 4 micron filter. The sample was cooled to room temperature and the head space flushed with perfluorobutane gas. The vials were shaken in a cap mixer for 45 s and the microbubbles washed 2 times with deionised water. The infranatant was discarded and replaced with a 1 mL aliquot of the protein solution from b) above. The conjugation reaction was allowed to proceed for 1 h. The bubbles were centrifuged and infranatant exchanged with a further 1 mL of protein solution. The incubation step was repeated until all protein solution was used up. The microbubbles were then washed extensively with water and analysed by Coulter counter. The microbubbles were tested in the flow chamber assay described in Example 1c). Microbubbles modified with protein were found to bind in higher numbers than those comprising either lipopeptide/DSPS or DSPS alone.

It is envisaged that the targeting/therapeutic/ultrasound activities of these microbubbles be evaluated in models of in vitro and in vivo thrombogenisis.

EXAMPLE 25

Multiple-specific PFB Gas-filled Microbubbles Encapsulated with DSPS and a Lipopeptide Comprising a Heparin Sulphate Binding peptde (KRKR) (SEq ID NO:1) and a Fibronectin Peptide (WOPPRARI) (SEQ ID NO:2) for Targeting and a Lipopeptide Containing Atenolol for Therapeutic Applications a) Synthesis of a Lipopeptide Consisting of a Heparin Sulphate Binding Peptide (KRKR) (SEQ ID NO:1) and a Fibronectin Peptide (WOPPRARI) (SEQ ID NO:2).

Synthesis and purification described in example 1a).

b) Synthesis of a Protected Atenolol Derivative Suitable for Solid Phase Coupling i) Synthesis of methyl 4-[(2,3-epoxy)propoxy] phenylacetate A mixture of methyl 4-hydroxyphenylacetate (4.98 g, 0.03 mol), epichlorohydrin (23.5 ml, 0.30 mol) and pyridine (121 μl, 1.5 mmol) was stirred at 85° C. for 2 h. The reaction mixture was cooled, and excess epichlorohydrin was distilled off (rotavapor). The residue was taken up in ethyl acetate, washed with brine and dried (Na$_2$SO$_4$) The solution was filtered and concentrated. The dark residue was chromatographed (silica, hexane/ethyl acetate 7:3) to give 2.25 g (34%) of a colourless oil. $^1$H (300 MHz) and $^{13}$C NMR (75 MHz) spectra were in accordance with the structure.

ii) Synthesis of methyl 4-[2-hydroxy-3-[(1-methylethyl) amino]-propoxy]phenylacetate A mixture of methyl 4-[(2,3-epoxy)propoxy] phenylacetate (2.00 g, 9.00 mmol), isopropylamine (23 ml, 0.27 mol) and water (1.35 ml, 74.7 mmol) was stirred at room temperature overnight. The reaction mixture was concentrated (rotavapor) and the oily residue was dissolved in chloroform and dried (Na$_2$SO$_4$). Filtration and concentration gave quantitative yield of a yellow oil that was used in the next step without further purification. The structure was verified by $^1$H and $^{13}$C NMR analysis.

iii) Synthesis of 4-[2-hydroxy-3-[(1-methylethyl) amino]-propoxyl]phenylacetic acid hydrochloride A solution of methyl 4-[2-hydroxy-3-[(1-methylethyl) amino]-propoxy]phenylacetate (563 mg, 2.00 mmol) in 6 M hydrochloric acid (15 ml) was heated at 100° C. for 4h. The reaction mixture was concentrated (rotavapor) and the residue was taken up in water and lyophilised. $^1$H and $^{13}$C NMR spectra were in accordance with the strucure and MALDI mass spectrometry gave a M+H at 268 as expected.

iv) Synthesis of N-Boc-4-[2-hydroxy-3-[(1-methylethyl) amino]-propoxy]phenylacetic acid A solution of the 4-[2-hydroxy-3-[(1-methylethyl) amino]-propoxy]phenylacetic acid hydrochloride (2.0 mmol) in water (2 ml) was added to a solution of sodium bicarbonate (0.60 g, 7.2 mmol) in water/dioxane (2:1, 15 ml). A solution of di-tert-butyl dicarbonate (0.48 g, 2.2 mmol) in dioxane (5 ml) was added. Progress of the reaction was monitored by TLC analysis (silica, CHCl$_3$/MeOH/AcOH 85:10:5), and portions of di-tert-butyl dicarbonate were added until conversion was complete. The reaction mixture was poured onto water saturated with potassium hydrogensulphate and organic material was extracted into ethyl acetate. The organic phase was washed with water and brine, dried (Na$_2$SO$_4$) and filtered to give 0.6 g of crude material. The product was purified by chromatography (silica, CHCl$_3$/MeOH/AcOH 85:10:5). The solution was concentrated and the residue was taken up in glacial acetic acid and lyophilised. Yield 415 mg (56%), white solid. The structure was confirmed by $^1$H and $^{13}$C NMR analysis.

c) Synthesis of a Lipopeptide Functionalised with Atenolol (SEQ ID NO:19)

(SEQ ID NO: 19)

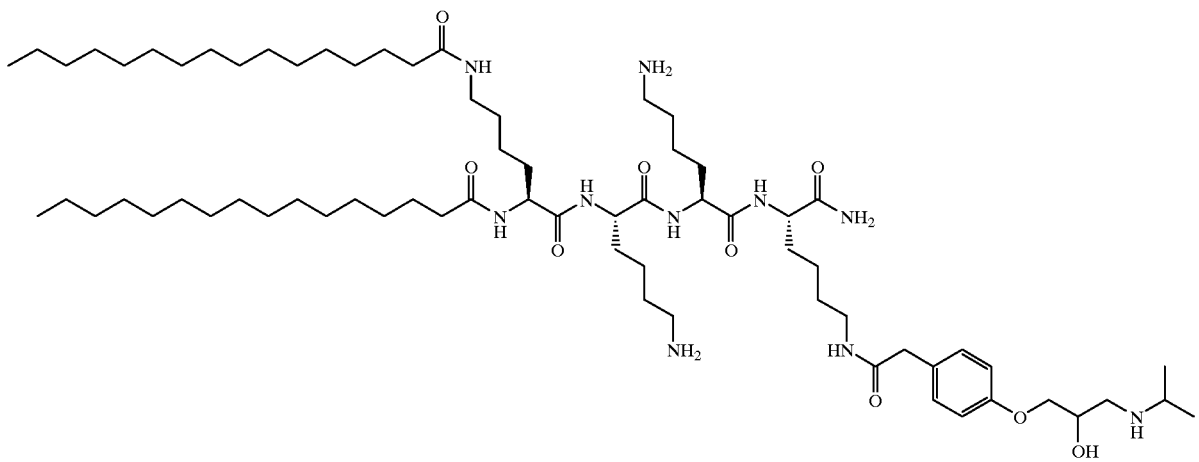

The structure shown above was synthesised on a manual nitrogen bubbler starting with Fmoc protected Rink Amide MBHA resin (Novabiochem) on a 0.125 mmol scale, using amino acids from Novabiochem, palmitic acid from Fluka and the compound from a). Coupling was carried out using standard TBTU/HOBt/DIEA protocols.

Simultaneous removal of the peptide from the resin and deprotection of side-chain protecting groups was carried out in TFA containing 5% EDT and 5% water for 2h. Crude material was precipitated from ether and purified by preparative liquid chromatography (Vydac 218TP1022 column) using a gradient of 70 to 100% B over 60 min (A=0.1% TFA/water and B=0.1% TFA/acetonitrile) at a flow rate of 10 ml/min. After lyophilisation a yield of 38 mg of pure material was obtained (analytical HPLC: gradient 70–100% B over 20 min, A=0.1% TFA/water and B =0.1% TFA/acetonitrile, flow rate 1 ml/min, column Vydac 218TP54, detection UV 214 nm, retention time 25 min). Further characterisation was carried out using MALDI mass spectrometry (ACH matrix), giving M+H at 1258, expected 1257.

d) Preparation of Gas-filled Microbubbles of DSPS Comprising a Lipopeptide Consisting of a Heparin Sulphate Binding Peptide (KRKR) (SEQ ID NO:1) and a Fibronectin Peptide (WOPPRARI) (SEQ ID NO:2) and a Lipopeptide Containing Atenolol A solution of 1.4% propylene glycol/2.4% glycerol (1.0 ml) was added to a mixture of DSPS (Avanti, 5.0 mg), product from a) (0.5 mg) and product from c) (0.5 mg) in a vial. The mixture was sonicated for 5 min and then heated at 80° C. for 5 min (vial was shaken during warming). The solution was filtered and cooled. Head space was flushed with perfluorobutane gas and the vial was shaken in a cap mixer for 45s followed by extensive washing with deionised water.

Incorporation of atenolol containing lipopeptide into the bubbles was confirmed by MALDI-MS as described in example 1b).

e) In Vitro Study of Multiple-specific Gas-filled Microbubbles.

In vitro analysis of the microbubble suspension was carried out as described in example 1c). A gradual accumulation of the microbubbles on the cells took place which was dependant on the flow rate. By increasing the flow rate the cells started to become detached from the coverslip, the microbubbles were still bound to the cells. Control bubbles not carrying the vector did not adhere to the endothelial cells and disappeared from the cells under minimal flow conditions.

EXAMPLE 26

PFB Gas-filled Microbubbles of DSPS Containing a Cholesterol Ester of Chlorambucil for Diagnostic and Therapeutic Applications This example is directed at non-specific modification of a multiplicity of cell receptors on endothelial cells.

a) Synthesis of Cholesterol 4-[4-[bis(2-chloroethyl)amino]-phenyl]butanoate

DIC (170 μl, 1.10 mmol) was added to a solution of chlorambucil (Sigma, 669 mg, 2.20 mmol) in dry dichloromethane (15 ml). The mixture was stirred at room temperature for 0.5 h and added to a solution of cholesterol (Aldrich, 387 mg, 1.00 mmol) and DMAP (122 mg, 1.00 mmol) in dichloromethane (10 ml). The reaction mixture was stirred overnight and then poured onto 5% sodium bicarbonate. The phases were separated and the organic phase was washed with brine and dried (MgSO4). The solution was filtered and concentrated and the product was purified by column chromatography (silica, chloroform) to give 560 mg (83%) yield of colouless oil. The product was characterised by MALDI mass spectrometry, giving M+H at 674 as expected. Further characterisation was carried out using $^1H$ (500 MHz) and $^{13}C$ (125 MHz) NMR analysis, giving spectra in accordance with the structure.

b) Preparation of Gas-containing Microbubbles of DSPS Comprising a Cholesteryl Ester of Chloambucil for Diagnostic and/or Therapeutic Applications A solution of 1.4% propylene glycol/2.4% glycerol (1.0 ml) was added to a mixture of DSPS (Avanti, 4.5 mg) and product from a) (0.5 mg) in a vial. The mixture was sonicated for 5 min and then heated at 80° C. for 5 min (vial was shaken during warming) and cooled. Head space was flushed with perfluorobutane gas and the vial was shaken in a cap mixer for 45s followed by extensive washing with deionised water. MALDI mass spectrometry showed no detectable level of compound from a) in the final wash solution. Incorporation of chlorambucil cholesteryl ester into the bubbles was confirmed by MALDI-MS as follows: ca 50 μl of microbubbles were transferred to a clean vial containing ca 100 μl of 90% methanol. The mixture was sonicated for 30 s and analysed by MALDI-MS, giving a M+H peak at 668 corresponding to structure from a).

In combination with a tumour specific vector these microbubbles are considered useful as targeted drug delivery agents.

EXAMPLE 27

Multiple-specific Gas-filled Microbubbles of DSPS Comprising a Lipopeptide Containing Atenolol and a Cholesterol Derivative of Chlorambucil for Diagnostic and Therapeutic Applications a) Synthesis of a Protected Atenolol Derivative Suitable for Solid Phase Coupling
As described in example 25 section b).

b) Synthesis of a Lipopeptide Functionalised with Atenolol
As described in example 25 section c).

c) Synthesis of Cholesteryl 4-[4-[bis(2-chloroethyl)amino] phenyl] butanoate
As described in example 25 section d).

d) Preparation of Microbubbles of DSPS Comprising a Lipopeptide Containing Atenolol and a Cholesteryl Ester of Chloambucil A solution of 1.4% propylene glycol/2.4% glycerol (1.0 ml) was added to a mixture of DSPS (Avanti, 5.0 mg), product from b) (0.5 mg) and c) (0.5 mg) and in a vial. The mixture was sonicated for 5 min and then warmed to 80° C. for 5 min (vial was shaken during warming). The solution was filtered and cooled. Head space was flushed with perfluorobutane gas and the vial was shaken in a cap mixer for 45 s followed by extensive washing with deionised water. Incorporation of atenolol containing lipopeptide and chlorabucil analogue into the bubble membrane was confirmed by MALDI-MS as described in example 1c).

e) In Vitro Study of Multiple-specific PFB Gas-containing Microbubbles of DSPS Comprising a Lipopeptide Containing Atenolol and a Cholesterol Derivative of Chlorambucil for Diagnostic and Therapeutic Applications The in vitro assay described in example 1c) was used to assess cellular binding under flow conditions. A gradual accumulation of the microbubbles on the cells took place which was dependant on the flow rate. By increasing the flow rate the cells started to become detached from the coverslip, the microbubbles were still bound to the cells. Control bubbles not carrying the vector did not adhere to the endothelial cells and disappeared from the cells under minimal flow conditions.

EXAMPLE 28

Multiple-specific Gas-filled Microbubbles of DSPS Comprising a Lipopeptide Containing Atenolol for Cell Targeting and a Lipophilic Thiol Ester of Captopril for Therapeutic use.

a) Synthesis of a Protected Atenolol Derivative Suitable for Solid Phase coupling
As described in example 25 section b).

b) Synthesis of a Lipopeptide Functionalised with Atenolol
As described in example 25 section c).

c) Synthesis of Cholanic Acid Thiol Ester of Captopril

A mixture of 5-β-cholanic acid (Sigma, 361 mg, 1.00 mmol) and DIC (77 µl, 0.50 mmol) in dichloromethane (5 ml) was stirred for 10 min and then added to a solution of captopril (Sigma, 130 mg, 0.600 mmol) and DBU (180 µl, 1.20 mmol) in dichloromethane (10 ml). The reaction mixture was stirred overnight and then poured onto dilute hydrochloric acid. Chloroform (30 ml) was added. The phases were separated and the organic phase was washed with water and brine and dried (MgSO$_4$). After filtration and concentration the crude material was chromatographed (silica, chloroform/methanol/acetic acid 95:4:1). The product was lyophilised from a acetonitrile/water/ethanol mixture. Yield 137 mg (49%) of off-white solid. The structure was verified by $^1$H (500 MHz) and $^{13}$C (125 MHz) NMR spectroscopy. Further characterisation was carried out using MALDI mass spectrometry, giving a M+Na peak in positive mode at m/z 584.

d) Preparation of Gas-filled Microbubbles of DSPS Comprising a Lipopeptide Containing Atenolol for Cell Targeting and a Liiophilic Thiol Ester of Captopril for Therapeutic use.

A solution of 1.4% propylene glycol/2.4% glycerol (1.0 ml) was added to a mixture of DSPS (Avanti, 5.0 mg) and product from b) (0.5 mg) and c) (0.5 mg) in a vial. The mixture was sonicated for 5 min and then heated at 80° C. for 5 min (vial was shaken during warming) and cooled. Head space was flushed with perfluorobutane gas and the vial was shaken in a cap mixer for 45s followed by extensive washing with deionised water. MALDI mass spectrometry showed no detectable level of compound from b) and c) in the final wash solution. Incorporation of compounds from b) and from c) into the bubbles was confirmed by MALDI-MS as follows. Ca. 50 µl of microbubbles were transferred to a clean vial containing ca 100 µl of 90% methanol. The mixture was sonicated for 30s and analysed by MALDI-MS (ACH-matrix),giving peaks according to structures from b) and c), respectively.

e) In Vitro Study of Gas-containing Microbubbles from d)

The in vitro assay described in example 1c) was used to assess cellular binding under flow conditions. A gradual accumulation of the microbubbles on the cells took place which was dependant on the flow rate. By increasing the flow rate the cells started to become detached from the coverslip, the microbubbles were still bound to the cells. Control bubbles not carrying the vector did not adhere to the endothelial cells and disappeared from the cells under minimal flow conditions.

EXAMPLE 29

Gas-filled Microbubbles of Phosphatidylserine Comprising Biotinamide-PEG-B-Ala-Cholesterol and a Cholesterol Ester of Chlorambucil for Diagnostic and Therapeutic Applications a) Synthesis of Cholesterol N-Boc-β-alaninate DIC (510 µl) was added to a solution of Boc-β-Ala-OH (1.25 g, 6.60 mmol) in dichloromethane (15 ml) under an inert atmosphere. The reaction mixture was stirred for 30 min and then transferred to a flask containing a solution of cholesterol (1.16 g, 3.00 mmol) and DMAP (367 mg, 3.00 mmol) in dichloromethane (15 ml). The reaction mixture was stirred for 2 h and then mixed with an aqueous solution of potassium hydrogensulphate. The phases were separated and the aqueous phase extracted with chloroform. The combined organic phases were washed with aqueous potassium hydrogensulphate and water and dried over MgSO$_4$.

After filtration and evaporation the crude product was chromatographed (silica, chloroform/methanol 99:1) to give 1.63 g (97%) of white solid. The structure was confirmed by $^1$H NMR (500 MHz).

b) Synthesis of Cholesterol β-alaninate Hydrochloride

A solution of compound from a) (279 mg, 0.500 mmo1) in 1 M hydrochloric acid in 1,4-dioxan (5 ml) was stirred at room temperature for 4 h. The reaction mixture was concentrated to give a quantitative yield of cholesteryl β-alaninate hydrochloride. The structure was confirmed by 1H NMR (500 MHz) analysis and by MALDI mass spectrometry, giving a M+Na peak at 482, expected 481.

c) Biotin-PEG$_{3400}$-β-Ala-Cholesterol

To a solution of cholesteryl β-alaninate hydrochloride (15 mg, 0.03 mmol) in chloroform/wet methanol (2.6:1, 3 ml) was added triethylamine (42 µl, 0.30 mmol). The mixture was stirred for 10 minutes at room temperature and a solution of biotin-PEG3400-NHS (100 mg, 0.03 mmol) in 1,4-dioxane (1 ml) was added dropwise. After stirring at room temperature for 3 hours, the mixture was evapourated to dryness and the residue purified by flash chromatography to give white crystals, yield ; 102 mg (89%). The structure was verified by MALDI-MS and by NMR analysis.

d) Synthesis of Cholesteryl 4-[4-[bis(2-chloroethyl)amino] phenyl]butanoate

DIC (170 µl, 1.10 mmol) was added to a solution of chlorambucil (Sigma, 669 mg, 2.20 mmol) in dry dichloromethane (15 ml). The mixture was stirred at room temperature for 0.5 h and added to a solution of cholesterol (Aldrich, 387 mg, 1.00 mmol) and DMAP (122 mg, 1.00 mmol) in dichloromethane (10 ml). The reaction mixture was stirred overnight then poured into a solution of 5% sodium bicarbonate. The organic phase was washed with brine and dried over MgSO$_4$. The solution was filtered and concentrated and the product was purified by column chromatography (silica, chloroform) to give 560 mg (83%) yield of colouless oil. The product was characterised by MALDI mass spectrometry, giving M+H at 674 as expected. Further characterisation was carried out using $^1$H (500 MHz) and $^{13}$C (125 MHz) NMR analysis, giving spectra in accordance with the structure.

e) Preparation of Gas-filled Microbubbles

A solution of 1.4% propylene glycol/2.4% glycerol (1.0 ml) was added to a mixture of DSPS (Avanti, 5 mg) and product from c) (0.5 mg) and d) (0.5 mg) in a vial. The mixture was sonicated for 5 min and then heated at 80° C. for 5 min (vial was shaken during warming) and cooled. Head space was flushed with perfluorobutane gas and the vial was shaken in a cap mixer for 45s followed by extensive washing with deionised water. MALDI mass spectrometry showed no detectable level of compound from c and d) in the final wash solution.

Incorporation of compounds from c) and d) into the bubbles was confirmed by MALDI-MS as described in example 1b).

EXAMPLE 30

Gas-filled Microbubbles of DSPS Comprising a Lipopeptide Containing Chlorambucil for Diagnostic and Therapeutic Applications This example is directed at the preparation of functionalised microbubbles with non-specific affinity for a multiplicity of cell surface molecules.

a) Synthesis of a Lipopeptide Containing Chlorambucil (SEQ ID NO:20)

(SEQ ID NO: 20)

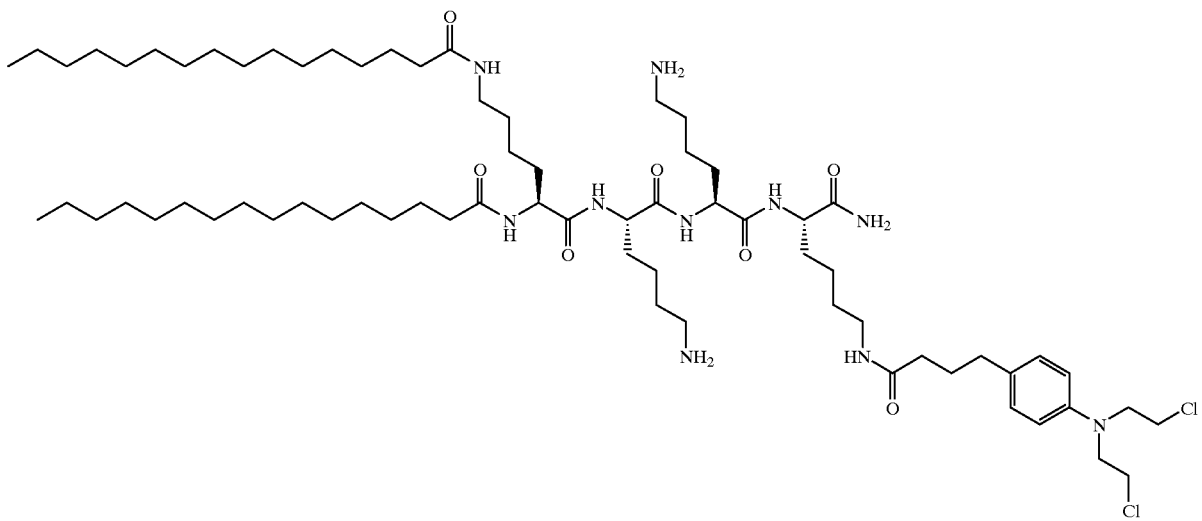

The structure shown above was synthesised on a manual nitrogen bubbler starting with Fmoc protected Rink Amide MBHA resin (Novabiochem) on a 0.125 mmol scale. Standard amino acids were purchased from Novabiochem and palmitic acid from Fluka. Coupling was carried out using standard TBTU/HOBt/DIEA protocol. Chlorambucil (Sigma) was coupled through the side-chain of Lys as a symmetrical anhydride using DIC preactivation.

Simultaneous removal of the peptide from the resin and deprotection of side-chain protecting groups was carried out in TFA containing 5% EDT, 5% water and 5% ethyl methyl sulphide for 2 h. An aliqout of 10 mg of the crude material was purified by preparative liquid chromatography (Vydac 218TP1022 column) using a gradient of 70 to 100% B over 60 min (A=0.1% TFA/water and B=0.1% TFA/acetonitrile) at a flow rate of 10 ml/min. After lyophilisation a yield of 30 mg of pure material was obtained (analytical HPLC: gradient 70–100% B over 20 min, A=0.1% TFA/water and B=0.1% TFA/acetonitrile; flow rate 1 ml/min; column Vydac 218TP54; detection UV 214 nm; retention time 26.5 min). Further characterisation was carried out using MALDI mass spectrometry, giving M+H at 1295, expected 1294.

b) Preparation of Qas-filled Microbubbles Comprising a Lipopeptide Containing Chlorambucil for Diagnostic and Therapeutic Applications A solution of 1.4% propylene glycol/2.4% glycerol (1.0 ml) was added to a mixture of DSPS (Avanti, 4.5 mg) and product from a) (0.5 mg) in a vial. The mixture was sonicated for 5 min and then heated at 80° C. for 5 min (vial was shaken during warming) and cooled. Head space was flushed with perfluorobutane gas and the vial was shaken in a cap mixer for 45s followed by extensive washing with deionised water. MALDI mass spectrometry showed no detectable level of compound from a) in the final wash solution.

Incorporation of chlorambucil containing lipopeptide into the bubbles was confirmed by MALDI-MS as follows. Ca 50 μl of microbubbles were transferred to a clean vial containing ca 100 μl of 90% methanol. The mixture was sonicated for 30s and analysed by MALDI-MS (ACH-matrix), giving a M+H peak at 1300, expected at 1294 and a M+Na peak at 1324, expected 1317.

c) In Vitro Study of Gas-containing Microbubbles of DSPS 'Doped' with a Lipopeptide Containing Chlorambucil for Diagnostic and Therapeutic Applications The microbubbles were evaluated using the in vitro flow assay described in example 1c). A gradual accumulation of the microbubbles on the cells took place which was dependant on the flow rate. By increasing the flow rate the cells started to become detached from the coverslip, the microbubbles were still bound to the cells. Control bubbles not carrying the vector did not adhere to the endothelial cells and disappeared from the cells under minimal flow conditions.

EXAMPLE 31

Gas-filled Microbubbles of DSPS Comprising a Lipopeptide Containing Atenolol and a Lipophilic Derivative of Captopril for Diagnostic and Therapeutic Applications a) Synthesis of a Protected Atenolol Derivative Suitable for Solid Phase Coupling As described in example 25) b)

b) Synthesis of N-[(S)-3-hexadecylthio-2-methylpropionyl] proline

DIEA (188 μl, 1.10 mmol) was added to a solution of 1-iodohexadecane (176 mg, 0.500 mmol), captopril (120 mg, 0.550 mmol) and DBU (165 μl, 1.10 mmol) in tetrahydrofuran (5 ml). The mixture was heated at 70° C. for 2h and then concentrated. The residue was poured onto water saturated with potassium hydrogensulphate and organic material was extracted into chloroform. The organic phase was washed with water and dried (MgSO$_4$). The product purified by chromatography (silica, CHCl$_3$/MeOH/AcOH 85:10:5) and lyophilised to give 105 mg (48%) of white solid material. The structure was verified by 1H (500 MHz) and 13C (125 MHz) analysis and further characterised by MALDI mass spectrometry, giving M-H in negative mode at m/z 440 as expected.

c) Preparation of Gas-filled Microbubbles of DSPS Comprising a Lipopeptide Containing Atenolol and a Lipophilic Derivative of Captopril for Diagnostic and Therapeutic Applications A solution of 1.4% propylene glycol/2.4% glycerol (1.0 ml) was added to a mixture of DSPS (Avanti, 4.5 mg), product from b) (0.5 mg) and c) in a vial. The mixture was sonicated for 5 min and then heated at 80° C. for 5 min (vial was shaken during warming) and cooled. Head space was flushed with perfluorobutane gas and the vial was shaken in a cap mixer for 45s followed by extensive washing with deionised water. MALDI mass spectrometry showed no detectable level of compound from b)or c) in the final wash solution. Incorporation of compound b) and c) containing lipopeptide into the bubbles was confirmed by MALDI-MS as described in example 1b).

d) In Vitro Study of Gas-containing Microbubbles of DSPS Comprising a Lipopeptide Containing Atenolol and a Lipophilic Derivative of Captopril for Diagnostic and Therapeutic Applications The microbubbles were evaluated using the in vitro flow assay described in example 1c). A gradual accumulation of the microbubbles on the cells took place which was dependant on the flow rate. By increasing the flow rate the cells started to become detached from the coverslip, the microbubbles were still bound to the cells. Control bubbles not carrying the vector did not adhere to the endothelial cells and disappeared from the cells under minimal flow conditions.

EXAMPLE 32

Floatation of Endothelial Cells by DSPS Microbubbles Comprising a Multiple-specific Lipopeptide that binds to the Endothelial Cells This example was carried out to show that the invention could also be used for cell separation.

The human endothelial cell line ECV 304, derived from a normal umbilical cord (ATCC CRL-1998) was cultures in Nunc culture flasks (chutney 153732) in RPMI 1640 medium (Bio Whitaker) to which L-Glutamine 200 mM, Penicillin/Streptomycin (10.000 U/ml and 10.00 mcg/ml) and 10% Fetal Calf Serum (Hyclone Lot no AFE 5183) were added. The cells were subcultured following trypsination with a split ratio of 1:5 to 1:7 when reaching confluence. 2 mill. cells from trypsinated confluent cultures were added to a set of 5 centrifuge tubes followed by either control microbubbles of DSPS, microbubbles from example 1 or microbubbles of DSPS doped with the endothelial cell binding lipopeptide from example 14a) at a concentration of 2, 4, 6 ,8 or 10 mill bubbles per tube. The cells at the bottom of the tubes after centrifugation at 400 g for 5 minutes were counted by Coulter counter. It was found that binding of four or more microbubbles to a cell brought about floatation. Furthermore all cells were floated by the endothelial cell binding lipopeptide bubbles while around 50% were floated with microbubbles from example 1).

EXAMPLE 33

Gene Transfer by PFB Gas-filled Microbubbles

This example is directed at the preparation of targeted microbubbles for gene transfer.

a) Preparation of DSPS Lipopeptide Bubbles/PFB Gas, Coated with Polyl-L-lysine

DSPS (4,5 mg) and lipopeptide from 17b)(0.5 mg) were weighed in two 2-ml vials. To each vial, 0.8 ml propyleneglycol/glycerol (4%) in water was added. The solution was heated at 80° C. for 5 minutes and shaken. The solution was then cooled to ambient temperature and the headspace flushed with perfluorobutane. The vials were shaken on a Capmix (Espe Capmix, 4450 oscillations/min) for 45 seconds and put on a roller table for 5 minutes. The content of the vials were mixed and the sample washed by centrifugation at 2000 rpm for 5 minutes. The infranatant was removed and the same volume of distilled water added. The washing procedure was repeated once.

poly-L-lysine HBr (Sigma, 20.6 mg) was dissolved in 2 mL water then an aliquot (0.4 mL) made up to 2 mL water. To 1.2 mL of the diluted poly-L-lysine solution was added 0.12 mL of the DSPS-lipopeptide bubble suspension. Following incubation excess polylysine was removed by extensive washing with water.

b) Transfection of Cells

Endothelial cells (ECV 304) were cultured in 6 well plates to a uniform subconfluent layer. A transfection mixture consisting of 5 $\mu$g DNA (an Enhanced Green Fluorescent Protein vector from CLONTECH) and 50 $\mu$l of microbubble suspension from a) in RPMI medium at a final volume of 250 $\mu$l was prepared. The mixture was left standing for 15 min at room temperature then 1 mL of complete RPMI medium added. The medium was removed from the cell culture dish, and the DNA-microbubble mixture added to the cells. The cells were incubated in a cell culture incubator (37° C.).

c) Ultrasonic Treatment

After 15 minutes incubation, selected wells were exposed to continious wave ultrasound of 1 MHz, 0.5 W/cm$^2$, for 30 seconds.

d) Incubation and Examination

The cells were further incubated in the cell culture incubator (37° C.) for approximately 4½ hours. The medium containing DNA-microbubbles was then removed by aspiration, and 2 ml complete RPMI medium was added. The cells were incubated for 40–70 hours before examination. Most of the medium was then removed, and the cells were examined by fluorescence microscopy. The results were compared to the results from control experiments were DNA or DNA-polylysine were added to the cells.

What is claimed is:

1. A targetable diagnostic and/or therapeutically active agent comprising a suspension in an aqueous carrier liquid of a reporter comprising gas-containing material in the form of phospholipid-stabilized gas microbubbles, said reporter being conjugated to more than one type of vector, the vectors binding to different targets on the same or different cells.

2. An agent as claimed in claim 1 wherein the gas is selected from the group consisting of air, nitrogen, oxygen, carbon dioxide, hydrogen, an inert gas, a sulphur fluoride, selenium hexafluoride, a low molecular weight hydrocarbon, a ketone, an ester, a halogenated low molecular weight hydrocarbon or a mixture of any of the foregoing.

3. An agent as claimed in claim 2 wherein the gas is selected from the group consisting of a perfluorinated ketone, perfluorinated ether and a perfluorocarbon.

4. An agent as claimed in claim 2 wherein the gas is selected from the group consisting of sulphur hexafluoride, perfluoropropane, perfluorobutane and perfluoropentane.

5. An agent as claimed in claim 1 wherein at least 75% of the phospholipid comprises phospholipid molecules individually bearing net overall charge.

6. An agent as claimed in claim 5 wherein at least 75% of the phospholipids are selected from the group consisting of phosphatidylserines, phosphatidylglycerols, phosphatidylinositols, phosphatidic acids and cardiolipins.

7. An agent as claimed in claim 6 wherein at least 80% of said phospholipids are phosphatidylserines.

8. An agent as claimed in claim 1, wherein said gas-containing material further comprises moieties capable of binding to a receptor system so as to induce a therapeutic response.

9. An agent as claimed in claim 1 wherein the vectors are selected from the group consisting of antibodies; cell adhesion molecules; cell adhesion molecule receptors; cytokines; growth factors; peptide hormones; non-bioactive binders of receptors for cell adhesion molecules, cytokines, growth factors and peptide hormones; oligonucleotides and modified oligonucleotides; DNA-binding drugs; protease substrates/inhibitors; and proteins and peptides which bind to cell-surface proteoglycans.

10. An agent as claimed in claim 1 wherein the vectors have affinity for targets at a level such that the agent interacts with but does not fixedly bind to said targets.

11. An agent as claimed in claim 10 wherein the vectors are selected from ligands for cell adhesion proteins and cell adhesion proteins which have corresponding ligands on endothelial cell surfaces.

12. An agent as claimed in claim 1 wherein the vectors are sited such that they are not readily exposed to the target.

13. An agent as claimed in claim 1 wherein the vectors are coupled or linked to the reporter by means of avidin-biotin and/or streptavidin-biotin interactions.

14. An agent as claimed in claim 1 wherein the vectors may be covalently or non-covalently coupled or linked to the reporter.

15. An agent as claimed in claim 1 wherein the vectors are coupled or linked to the reporter by means of electrostatic charge interaction.

16. An agent as claimed in claim 1 which further contains moieties which are radioactive or are effective as X-ray contrast agents, light imaging probes or spin labels.

17. An agent as claimed in claim 1 further comprising a therapeutic compound.

18. An agent as claimed in claim 17 wherein said therapeutic compound is an antineoplastic agent, blood product, biological response modifier, antifungal agent, hormone or hormone analogue, vitamin, enzyme, antiallergic agent, tissue factor inhibitor, platelet inhibitor, coagulation protein target inhibitor, fibrin formation inhibitor, fibrinolysis promoter, antiangiogenic, circulatory drug, metabolic potentiator, antitubercular, antiviral, vasodilator, antibiotic, antiinflammatory, antiprotozoan, antirheumatic, narcotic, opiate, cardiac glycoside, neuromuscular blocker, sedative, local anaesthetic, general anaesthetic or genetic material.

19. An agent as claimed in claim 17 wherein said therapeutic compound is covalently coupled or linked to the reporter through disulphide groups.

20. An agent as claimed in claim 17 wherein a lipophilic or lipophilically-derivatised therapeutic compound is linked to the reporter through hydrophobic interactions.

21. A process for the preparation of a targetable diagnostic and/or therapeutically active agent as defined in claim 1 which comprises coupling or linking more than one type of vector to the reporter comprising gas-containing material wherein the vectors bind to different targets on the same or different cells.

22. A process as claimed in claim 21 wherein a therapeutic compound is also combined with the reporter.

* * * * *

SEQUENCE LISTING

```
<160> NUMBER OF SEQ ID NOS:  27

<210> SEQ ID NO 1
<211> LENGTH: 4
<212> TYPE: PRT
<213> ORGANISM: Artificial Sequence
<220> FEATURE:
<223> OTHER INFORMATION: Description of Artificial Sequence:Heparin
      sulphate binding peptide

<400> SEQUENCE: 1

Lys Arg Lys Arg
```

-continued

```
<210> SEQ ID NO 2
<211> LENGTH: 8
<212> TYPE: PRT
<213> ORGANISM: Artificial Sequence
<220> FEATURE:
<223> OTHER INFORMATION: Description of Artificial Sequence:Fibronectin
      peptide

<400> SEQUENCE: 2

Trp Gln Pro Pro Arg Ala Arg Ile
  1               5

<210> SEQ ID NO 3
<211> LENGTH: 13
<212> TYPE: PRT
<213> ORGANISM: Artificial Sequence
<220> FEATURE:
<223> OTHER INFORMATION: Description of Artificial Sequence:Lipopeptide
      consisting of heparin sulphate binding peptide and
      fibronectin peptide
<221> NAME/KEY: MOD_RES
<222> LOCATION: (1)
<223> OTHER INFORMATION: Dipalmitoyl-lysine

<400> SEQUENCE: 3

Lys Lys Arg Lys Arg Trp Gln Pro Pro Arg Ala Arg Ile
  1               5                  10

<210> SEQ ID NO 4
<211> LENGTH: 4
<212> TYPE: PRT
<213> ORGANISM: Artificial Sequence
<220> FEATURE:
<223> OTHER INFORMATION: Description of Artificial Sequence:Synthetic
      RGDC sequence

<400> SEQUENCE: 4

Arg Gly Asp Cys
  1

<210> SEQ ID NO 5
<211> LENGTH: 24
<212> TYPE: PRT
<213> ORGANISM: Artificial Sequence
<220> FEATURE:
<223> OTHER INFORMATION: Description of Artificial Sequence:Synthetic
      fusion peptide comprising a PS binding component
      and a fibronectin  peptide sequence

<400> SEQUENCE: 5

Phe Asn Phe Arg Leu Lys Ala Gly Gln Lys Ile Arg Phe Gly Gly Gly
  1               5                  10                  15

Gly Trp Gln Pro Pro Arg Ala Ile
             20

<210> SEQ ID NO 6
<211> LENGTH: 6
<212> TYPE: PRT
<213> ORGANISM: Artificial Sequence
<220> FEATURE:
<223> OTHER INFORMATION: Description of Artificial Sequence:Biotinylated
      endothelin-1 peptide
<221> NAME/KEY: MOD_RES
<222> LOCATION: (1)
<223> OTHER INFORMATION: Biotin-D-Trp

<400> SEQUENCE: 6
```

```
Trp Leu Asp Ile Ile Trp
 1               5
```

<210> SEQ ID NO 7
<211> LENGTH: 10
<212> TYPE: PRT
<213> ORGANISM: Artificial Sequence
<220> FEATURE:
<223> OTHER INFORMATION: Description of Artificial Sequence:Biotinylated
      fibrin-antipolymerant peptide
<221> NAME/KEY: MOD_RES
<222> LOCATION: (1)
<223> OTHER INFORMATION: Biotin-Gly
<221> NAME/KEY: MOD_RES
<222> LOCATION: (10)
<223> OTHER INFORMATION: AMIDATION

<400> SEQUENCE: 7

```
Gly Pro Arg Pro Pro Glu Arg His Gln Ser
 1               5                  10
```

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence:Lipopeptide
<221> NAME/KEY: MOD_RES
<222> LOCATION: (5)
<223> OTHER INFORMATION: Biotinylated-lys
<221> NAME/KEY: MOD_RES
<222> LOCATION: (1)
<223> OTHER INFORMATION: Dipalmitoyl-lysine

<400> SEQUENCE: 8

```
Lys Trp Lys Lys Lys Gly
 1               5
```

<210> SEQ ID NO 9
<211> LENGTH: 25
<212> TYPE: DNA
<213> ORGANISM: Artificial Sequence
<220> FEATURE:
<223> OTHER INFORMATION: Description of Artificial Sequence:Biotinylated
      synthetic oligonucleotide
<221> NAME/KEY: misc_feature
<222> LOCATION: (1)
<223> OTHER INFORMATION: Biotinylated

<400> SEQUENCE: 9
gaaaggtagt ggggtcgtgt gccgg                                      25

<210> SEQ ID NO 10
<211> LENGTH: 25
<212> TYPE: DNA
<213> ORGANISM: Artificial Sequence
<220> FEATURE:
<223> OTHER INFORMATION: Description of Artificial Sequence:Biotinylated
      synthetic oligonucleotide
<221> NAME/KEY: misc_feature
<222> LOCATION: (1)
<223> OTHER INFORMATION: Biotinylated

<400> SEQUENCE: 10
ggcgctgatg atgttgttga ttctt                                      25

<210> SEQ ID NO 11
<211> LENGTH: 5
<212> TYPE: PRT

```
<213> ORGANISM: Artificial Sequence
<220> FEATURE:
<223> OTHER INFORMATION: Description of Artificial Sequence:Lipopeptide
      containing the RGD sequence and a fluorescein
      reporter group
<221> NAME/KEY: MOD_RES
<222> LOCATION: (1)
<223> OTHER INFORMATION: Dipalmitoyl-lys
<221> NAME/KEY: MOD_RES
<222> LOCATION: (4)
<223> OTHER INFORMATION: Acetyl-RGD-K-fluorescein side chain

<400> SEQUENCE: 11

Lys Lys Lys Lys Gly
 1               5

<210> SEQ ID NO 12
<211> LENGTH: 18
<212> TYPE: PRT
<213> ORGANISM: Artificial Sequence
<220> FEATURE:
<223> OTHER INFORMATION: Description of Artificial Sequence:Synthetic
      endothelial cell binding lipopeptide
<221> NAME/KEY: MOD_RES
<222> LOCATION: (1)
<223> OTHER INFORMATION: 2-n-hexadecylstearyl-lysine
<221> NAME/KEY: MOD_RES
<222> LOCATION: (18)
<223> OTHER INFORMATION: AMIDATION

<400> SEQUENCE: 12

Lys Leu Ala Leu Lys Leu Ala Leu Lys Ala Leu Lys Ala Ala Leu Lys
 1               5                  10                  15

Leu Ala

<210> SEQ ID NO 13
<211> LENGTH: 5
<212> TYPE: PRT
<213> ORGANISM: Artificial Sequence
<220> FEATURE:
<221> NAME/KEY: MOD_RES
<222> LOCATION: (1)
<223> OTHER INFORMATION: Dipalmitoyl-lysine
<221> NAME/KEY: MOD_RES
<222> LOCATION: (4)
<223> OTHER INFORMATION: Acp
<223> OTHER INFORMATION: Description of Artificial Sequence:Thiol
      functionalised lipid molecule

<400> SEQUENCE: 13

Lys Lys Lys Xaa Cys
 1               5

<210> SEQ ID NO 14
<211> LENGTH: 4
<212> TYPE: PRT
<213> ORGANISM: Artificial Sequence
<220> FEATURE:
<221> NAME/KEY: MOD_RES
<222> LOCATION: (1)
<223> OTHER INFORMATION: Dipalmitoyl-lysine
<221> NAME/KEY: MOD_RES
<222> LOCATION: (4)
<223> OTHER INFORMATION: Amide-linked via side chain to captopril
<221> NAME/KEY: MOD_RES
<222> LOCATION: (4)
<223> OTHER INFORMATION: AMIDATION
<223> OTHER INFORMATION: Description of Artificial Sequence:Synthetic
      lipopeptide functionalised with captopril

<400> SEQUENCE: 14
```

```
Lys Lys Lys Lys
  1

<210> SEQ ID NO 15
<211> LENGTH: 13
<212> TYPE: PRT
<213> ORGANISM: Artificial Sequence
<220> FEATURE:
<223> OTHER INFORMATION: Description of Artificial Sequence:Synthetic
      lipopeptide with affinity for endothelial cells
<221> NAME/KEY: MOD_RES
<222> LOCATION: (1)
<223> OTHER INFORMATION: Dipalmitoyl-lysine
<221> NAME/KEY: MOD_RES
<222> LOCATION: (4)
<223> OTHER INFORMATION: Acp
<221> NAME/KEY: MOD_RES
<222> LOCATION: (13)
<223> OTHER INFORMATION: AMIDATION

<400> SEQUENCE: 15

Lys Lys Lys Xaa Ile Arg Arg Val Ala Arg Pro Pro Leu
  1               5                  10

<210> SEQ ID NO 16
<211> LENGTH: 14
<212> TYPE: PRT
<213> ORGANISM: Artificial Sequence
<220> FEATURE:
<223> OTHER INFORMATION: Description of Artificial Sequence:Lipopeptide
      comprising an interleukin 1 receptor binding
      peptide
<221> NAME/KEY: MOD_RES
<222> LOCATION: (1)
<223> OTHER INFORMATION: Dipalmitoyl-lysine

<400> SEQUENCE: 16

Lys Gly Asp Trp Asp Gln Phe Gly Leu Trp Arg Gly Ala Ala
  1               5                  10

<210> SEQ ID NO 17
<211> LENGTH: 12
<212> TYPE: PRT
<213> ORGANISM: Artificial Sequence
<220> FEATURE:
<223> OTHER INFORMATION: Description of Artificial Sequence:Core peptide
      comprising dabsylated-atherosclerotic plaque
      binding sequence and RGDS
<221> NAME/KEY: MOD_RES
<222> LOCATION: (1)
<223> OTHER INFORMATION: Dabsylated-tyrosine
<221> NAME/KEY: MOD_RES
<222> LOCATION: (10)
<223> OTHER INFORMATION: Arg-Gly-Asp-Ser chain linked via NH2 group of
      lysine

<400> SEQUENCE: 17

Tyr Arg Ala Leu Val Asp Thr Leu Lys Lys Gly Cys
  1               5                  10

<210> SEQ ID NO 18
<211> LENGTH: 15
<212> TYPE: PRT
<213> ORGANISM: Artificial Sequence
<220> FEATURE:
<223> OTHER INFORMATION: Description of Artificial Sequence:Lipopeptide
      with an affinity for thrombi
<221> NAME/KEY: MOD_RES
<222> LOCATION: (1)
<223> OTHER INFORMATION: Dipalmitoyl-lysine
<221> NAME/KEY: MOD_RES
<222> LOCATION: (15)
```

```
<223> OTHER INFORMATION: AMIDATION

<400> SEQUENCE: 18

Lys Asn Asp Gly Asp Phe Glu Glu Ile Pro Glu Glu Tyr Leu Gln
 1               5                  10                  15

<210> SEQ ID NO 19
<211> LENGTH: 4
<212> TYPE: PRT
<213> ORGANISM: Artificial Sequence
<220> FEATURE:
<223> OTHER INFORMATION: Description of Artificial Sequence:Lipopeptide
      functionalised with atenolol
<221> NAME/KEY: MOD_RES
<222> LOCATION: (1)
<223> OTHER INFORMATION: Dipalmitoyl-lysine
<221> NAME/KEY: MOD_RES
<222> LOCATION: (4)
<223> OTHER INFORMATION: Lysine with side chain linked via amide bond to
      atenolol
<221> NAME/KEY: MOD_RES
<222> LOCATION: (4)
<223> OTHER INFORMATION: AMIDATION

<400> SEQUENCE: 19

Lys Lys Lys Lys
 1

<210> SEQ ID NO 20
<211> LENGTH: 4
<212> TYPE: PRT
<213> ORGANISM: Artificial Sequence
<220> FEATURE:
<223> OTHER INFORMATION: Description of Artificial Sequence:Lipopeptide
      containing chlorambucil
<221> NAME/KEY: MOD_RES
<222> LOCATION: (1)
<223> OTHER INFORMATION: Dipalmitoyl-lysine
<221> NAME/KEY: MOD_RES
<222> LOCATION: (4)
<223> OTHER INFORMATION: Lysine with side chain linked via amide bond to
      chlorambucil
<221> NAME/KEY: MOD_RES
<222> LOCATION: (4)
<223> OTHER INFORMATION: AMIDATION

<400> SEQUENCE: 20

Lys Lys Lys Lys
 1

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence:Synthetic
      RGDS sequence

<400> SEQUENCE: 21

Arg Gly Asp Ser
 1

<210> SEQ ID NO 22
<211> LENGTH: 9
<212> TYPE: PRT
<213> ORGANISM: Artificial Sequence
<220> FEATURE:
<223> OTHER INFORMATION: Description of Artificial Sequence:
      Atherosclerotic plaque-binding peptide

<400> SEQUENCE: 22
```

```
Tyr Arg Ala Leu Val Asp Thr Leu Lys
  1               5
```

<210> SEQ ID NO 23
<211> LENGTH: 16
<212> TYPE: PRT
<213> ORGANISM: Artificial Sequence
<220> FEATURE:
<223> OTHER INFORMATION: Description of Artificial Sequence:
      Atherosclerotic plaque-binding peptide

<400> SEQUENCE: 23

```
Tyr Ala Lys Phe Arg Glu Thr Leu Glu Asp Thr Arg Asp Arg Met Tyr
  1               5                  10                  15
```

<210> SEQ ID NO 24
<211> LENGTH: 17
<212> TYPE: PRT
<213> ORGANISM: Artificial Sequence
<220> FEATURE:
<223> OTHER INFORMATION: Description of Artificial Sequence:
      Atherosclerotic plaque-binding peptide

<400> SEQUENCE: 24

```
Arg Ala Leu Val Asp Thr Glu Phe Lys Val Lys Gln Glu Ala Gly Ala
  1               5                  10                  15

Lys
```

<210> SEQ ID NO 25
<211> LENGTH: 14
<212> TYPE: PRT
<213> ORGANISM: Artificial Sequence
<220> FEATURE:
<223> OTHER INFORMATION: Description of Artificial Sequence:Thrombus
      binding peptide

<400> SEQUENCE: 25

```
Asn Asp Gly Asp Phe Glu Glu Ile Pro Glu Glu Tyr Leu Gln
  1               5                  10
```

<210> SEQ ID NO 26
<211> LENGTH: 4
<212> TYPE: PRT
<213> ORGANISM: Artificial Sequence
<220> FEATURE:
<223> OTHER INFORMATION: Description of Artificial Sequence:Thrombus
      binding peptide

<400> SEQUENCE: 26

```
Gly Pro Arg Gly
  1
```

<210> SEQ ID NO 27
<211> LENGTH: 13
<212> TYPE: PRT
<213> ORGANISM: Artificial Sequence
<220> FEATURE:
<223> OTHER INFORMATION: Description of Artificial Sequence:Platelet
      binding peptide

<400> SEQUENCE: 27

```
Pro Leu Tyr Lys Lys Ile Ile Lys Lys Leu Leu Glu Ser
  1               5                  10
```